US009375164B2

(12) United States Patent
Tolkowsky et al.

(10) Patent No.: US 9,375,164 B2
(45) Date of Patent: *Jun. 28, 2016

(54) CO-USE OF ENDOLUMINAL DATA AND EXTRALUMINAL IMAGING

(71) Applicant: SYNC-RX, LTD., Netanya (IL)

(72) Inventors: David Tolkowsky, Tel Aviv (IL); Ran Cohen, Petah Tikva (IL); Eldad Klaiman, Herzlia (IL); Zohar Barzelay, Zichron Yaakov (IL)

(73) Assignee: SYNC-RX, LTD., Netanya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,996

(22) Filed: Jun. 18, 2015

(65) Prior Publication Data

US 2015/0282737 A1 Oct. 8, 2015

Related U.S. Application Data

(63) Continuation of application No. 13/228,229, filed on Sep. 8, 2011, which is a continuation of application No. PCT/IL2011/000612, filed on Jul. 28, 2011.

(60) Provisional application No. 61/344,464, filed on Jul.

(Continued)

(51) Int. Cl.
*A61B 5/05* (2006.01)
*A61B 5/06* (2006.01)
(Continued)

(52) U.S. Cl.
CPC . *A61B 5/066* (2013.01); *A61B 8/12* (2013.01); *A61B 19/5244* (2013.01);
(Continued)

(58) Field of Classification Search
CPC ........ A61B 8/12; A61B 5/066; A61B 5/0066; A61B 5/0073; A61B 5/0075; A61B 5/0086; A61B 5/0084
See application file for complete search history.

(56) References Cited

U.S. PATENT DOCUMENTS 3,871,360 A 3/1975 Van Horn et al.
3,954,098 A 5/1976 Dick et al.
(Continued)

FOREIGN PATENT DOCUMENTS

EP 2 570 079 A1 3/2013
WO 94/10904 5/1994
(Continued)

OTHER PUBLICATIONS

An Official Action dated Jul. 28, 2015, which issued during the prosecution of Applicant's U.S. Appl. No. 12/075,252.
(Continued)

*Primary Examiner* — Joel Lamprecht
(74) *Attorney, Agent, or Firm* — Sughrue Mion, PLLC

(57) ABSTRACT

Apparatus and methods are described for use with an endoluminal data-acquisition device having a radiopaque portion coupled thereto, including, while the endoluminal data-acquisition device is being moved through the lumen, acquiring a plurality of endoluminal data points of the lumen using the endoluminal data-acquisition device. A combined extraluminal image of the lumen is generated that contains images of the radiopaque portion at first and second locations within the lumen, by co-registering first and second extraluminal images with each other. At least one location on the combined extraluminal image is identified as corresponding to a location within the lumen at which a given one of the endoluminal data points was acquired, by identifying the first and second locations of the radiopaque portion within the combined extraluminal image. An output is generated, in response thereto. Other applications are also described.

22 Claims, 11 Drawing Sheets

Related U.S. Application Data 29, 2010, provisional application No. 61/344,875, filed on Nov. 1, 2010, provisional application No. 61/457,339, filed on Mar. 3, 2011, provisional application No. 61/457,455, filed on Apr. 1, 2011, provisional application No. 61/457,780, filed on Jun. 2, 2011, provisional application No. 61/457,951, filed on Jul. 15, 2011.

(51) Int. Cl.
   *A61B 8/12* (2006.01)
   *A61B 19/00* (2006.01)
   *A61B 5/00* (2006.01)

(52) U.S. Cl.
   CPC .............. *A61B 19/54* (2013.01); *A61B 5/0066* (2013.01); *A61B 5/0073* (2013.01); *A61B 5/0075* (2013.01); *A61B 5/0084* (2013.01); *A61B 5/0086* (2013.01); *A61B 2019/5238* (2013.01); *A61B 2019/5278* (2013.01); *A61B 2019/5466* (2013.01); *A61B 2576/00* (2013.01)

(56) References Cited

U.S. PATENT DOCUMENTS

| | | |
|---|---|---|
| 4,016,871 A | 4/1977 | Schiff |
| 4,031,884 A | 6/1977 | Henzel |
| 4,245,647 A | 1/1981 | Randall |
| 4,270,143 A | 5/1981 | Morris |
| 4,316,218 A | 2/1982 | Gay |
| 4,382,184 A | 5/1983 | Wernikoff |
| 4,545,390 A | 10/1985 | Leary |
| 4,709,385 A | 11/1987 | Pfeiler |
| 4,712,560 A | 12/1987 | Schaefer et al. |
| 4,723,938 A | 2/1988 | Goodin et al. |
| 4,741,328 A | 5/1988 | Gabbay |
| 4,758,223 A | 7/1988 | Rydell |
| 4,770,184 A | 9/1988 | Greene, Jr. et al. |
| 4,849,906 A | 7/1989 | Chodos et al. |
| 4,865,043 A | 9/1989 | Shimoni |
| 4,878,115 A | 10/1989 | Elion |
| 4,920,413 A | 4/1990 | Nakamura |
| 4,991,589 A | 2/1991 | Hongo et al. |
| 4,994,965 A | 2/1991 | Crawford et al. |
| 5,020,516 A | 6/1991 | Biondi |
| 5,054,045 A | 10/1991 | Whiting et al. |
| 5,054,492 A | 10/1991 | Scribner |
| 5,056,524 A | 10/1991 | Oe |
| 5,062,056 A | 10/1991 | Lo et al. |
| 5,150,292 A | 9/1992 | Hoffmann et al. |
| 5,176,619 A | 1/1993 | Segalowitz |
| 5,177,796 A | 1/1993 | Feig et al. |
| 5,293,574 A | 3/1994 | Roehm et al. |
| 5,295,486 A | 3/1994 | Wollschlager et al. |
| 5,330,496 A | 7/1994 | Alferness |
| 5,357,550 A | 10/1994 | Asahina et al. |
| 5,429,144 A | 7/1995 | Wilk |
| 5,457,728 A | 10/1995 | Whiting et al. |
| 5,457,754 A | 10/1995 | Han et al. |
| 5,486,192 A | 1/1996 | Walinsky et al. |
| 5,537,490 A | 7/1996 | Yukawa |
| 5,538,494 A | 7/1996 | Matsuda |
| 5,577,502 A | 11/1996 | Darrow et al. |
| 5,586,201 A | 12/1996 | Whiting et al. |
| 5,596,990 A | 1/1997 | Yock |
| 5,613,492 A | 3/1997 | Feinberg |
| 5,619,995 A | 4/1997 | Lobodzinski |
| 5,630,414 A | 5/1997 | Horbaschek |
| 5,674,217 A | 10/1997 | Wahlstrom et al. |
| 5,724,977 A | 3/1998 | Yock |
| 5,764,723 A | 6/1998 | Weinberger |
| 5,766,208 A | 6/1998 | McEwan |
| 5,792,157 A | 8/1998 | Mische et al. |
| 5,807,327 A | 9/1998 | Green et al. |
| 5,809,105 A | 9/1998 | Roehm et al. |
| 5,822,391 A | 10/1998 | Whiting et al. |
| 5,830,222 A | 11/1998 | Makower |
| 5,879,305 A | 3/1999 | Yock |
| 5,885,218 A | 3/1999 | Teo |
| 5,885,244 A | 3/1999 | Leone et al. |
| 5,916,194 A | 6/1999 | Jacobsen et al. |
| 5,921,934 A | 7/1999 | Teo |
| 5,971,976 A | 10/1999 | Wang et al. |
| 6,088,488 A | 7/2000 | Hardy et al. |
| 6,095,976 A | 8/2000 | Nachtomy |
| 6,120,455 A | 9/2000 | Teo |
| 6,120,523 A | 9/2000 | Crocker et al. |
| 6,126,608 A | 10/2000 | Kemme et al. |
| 6,148,095 A | 11/2000 | Prause et al. |
| 6,152,878 A | 11/2000 | Nachtomy |
| 6,195,445 B1 | 2/2001 | Dubuisson-Jolly et al. |
| 6,233,478 B1 | 5/2001 | Liu |
| 6,246,898 B1 | 6/2001 | Vesely et al. |
| 6,254,541 B1 | 7/2001 | Teo |
| 6,267,727 B1 | 7/2001 | Teo |
| 6,278,767 B1 | 8/2001 | Hsieh |
| 6,331,181 B1 | 12/2001 | Tierney et al. |
| 6,370,417 B1 | 4/2002 | Horbaschek et al. |
| 6,377,011 B1 | 4/2002 | Ben-Ur |
| 6,442,415 B1 | 8/2002 | Bis et al. |
| 6,454,715 B2 | 9/2002 | Teo |
| 6,454,776 B1 | 9/2002 | Tajima et al. |
| 6,473,635 B1 | 10/2002 | Rasche |
| 6,491,636 B2 | 12/2002 | Chenal |
| 6,493,575 B1 | 12/2002 | Kesten et al. |
| 6,496,716 B1 | 12/2002 | Langer et al. |
| 6,532,380 B1 | 3/2003 | Close et al. |
| 6,538,634 B1 | 3/2003 | Chui et al. |
| 6,546,271 B1 | 4/2003 | Reisfeld |
| 6,576,007 B2 | 6/2003 | Dehdashtian |
| 6,589,176 B2 | 7/2003 | Jago |
| 6,616,596 B1 | 9/2003 | Milbocker |
| 6,643,533 B2 | 11/2003 | Knoplioch |
| 6,659,953 B1 | 12/2003 | Sumanaweera et al. |
| 6,666,863 B2 | 12/2003 | Wentzel et al. |
| 6,704,593 B2 | 3/2004 | Stainsby |
| 6,708,052 B1 | 3/2004 | Mao et al. |
| 6,711,436 B1 | 3/2004 | Duhaylongsod |
| 6,718,055 B1 | 4/2004 | Suri |
| 6,726,675 B1 | 4/2004 | Beyar |
| 6,728,566 B1 | 4/2004 | Subramanyan |
| 6,731,973 B2 | 5/2004 | Voith |
| 6,786,896 B1 | 9/2004 | Madhani et al. |
| 6,788,827 B1 | 9/2004 | Makram-Ebeid |
| 6,796,972 B1 | 9/2004 | Sinofsky et al. |
| 6,835,177 B2 | 12/2004 | Fritz et al. |
| 6,858,003 B2 | 2/2005 | Evans et al. |
| 6,912,471 B2 | 6/2005 | Heigl |
| 6,937,696 B1 | 8/2005 | Mostafavi |
| 6,959,266 B1 | 10/2005 | Mostafavi |
| 6,973,202 B2 | 12/2005 | Mostafavi |
| 6,980,675 B2 | 12/2005 | Evron et al. |
| 6,996,430 B1 | 2/2006 | Gilboa et al. |
| 6,999,852 B2 | 2/2006 | Green |
| 7,031,504 B1 | 4/2006 | Argiro et al. |
| 7,070,555 B2 | 7/2006 | Siess |
| 7,085,342 B2 | 8/2006 | Younis et al. |
| 7,134,994 B2 | 11/2006 | Alpert |
| 7,155,046 B2 | 12/2006 | Aben et al. |
| 7,155,315 B2 | 12/2006 | Niemeyer et al. |
| 7,180,976 B2 | 2/2007 | Wink et al. |
| 7,191,100 B2 | 3/2007 | Mostafavi |
| 7,209,779 B2 | 4/2007 | Kaufman |
| 7,215,802 B2 | 5/2007 | Klingensmith |
| 7,221,973 B2 | 5/2007 | Nitz |
| 7,269,457 B2 | 9/2007 | Shafer |
| 7,289,652 B2 | 10/2007 | Florent et al. |
| 7,321,677 B2 | 1/2008 | Evron et al. |
| 7,339,585 B2 | 3/2008 | Verstraelen et al. |
| 7,343,032 B2 | 3/2008 | Oakley et al. |
| 7,343,195 B2 | 3/2008 | Strommer et al. |
| 7,359,554 B2 | 4/2008 | Klingensmith |
| 7,369,691 B2 | 5/2008 | Kondo et al. |

(56) References Cited

U.S. PATENT DOCUMENTS

| | | |
|---|---|---|
| 7,397,935 B2 | 7/2008 | Kimmel |
| 7,398,116 B2 | 7/2008 | Edwards |
| 7,517,318 B2 | 4/2009 | Altmann |
| 7,546,154 B2 | 6/2009 | Hornegger et al. |
| 7,587,074 B2 | 9/2009 | Zarkh et al. |
| 7,599,730 B2 | 10/2009 | Hunter |
| 7,604,601 B2 | 10/2009 | Altmann |
| 7,650,179 B2 | 1/2010 | Redel et al. |
| 7,653,426 B2 | 1/2010 | Yatsuo et al. |
| 7,668,362 B2 | 2/2010 | Olson et al. |
| 7,693,349 B2 | 4/2010 | Gering |
| 7,697,974 B2 | 4/2010 | Jenkins |
| 7,713,210 B2 | 5/2010 | Byrd |
| 7,729,743 B2 | 6/2010 | Sabczynski et al. |
| 7,729,746 B2 | 6/2010 | Redel et al. |
| 7,740,584 B2 | 6/2010 | Donaldson |
| 7,742,629 B2 | 6/2010 | Zarkh et al. |
| 7,773,787 B2 | 8/2010 | Tek et al. |
| 7,773,792 B2 | 8/2010 | Kimmel |
| 7,778,488 B2 | 8/2010 | Nord |
| 7,778,688 B2 | 8/2010 | Strommer |
| 7,822,291 B2 | 10/2010 | Guetter |
| 7,831,076 B2 | 11/2010 | Altmann |
| 7,844,126 B2 | 11/2010 | Mory et al. |
| 7,848,553 B2 | 12/2010 | Hertel |
| 7,877,132 B2 | 1/2011 | Rongen |
| 7,889,905 B2 | 2/2011 | Higgins et al. |
| 7,892,177 B2 | 2/2011 | Rold et al. |
| 7,914,442 B1 | 3/2011 | Gazdzinski |
| 7,916,912 B2 | 3/2011 | Abramov et al. |
| 7,925,064 B2 | 4/2011 | Cloutier et al. |
| 7,925,069 B2 | 4/2011 | Ortyn et al. |
| 7,925,327 B2 | 4/2011 | Weese |
| 7,927,275 B2 | 4/2011 | Kuban |
| 7,930,014 B2 | 4/2011 | Huennekens et al. |
| 7,935,055 B2 | 5/2011 | Burckhardt |
| 7,961,926 B2 | 6/2011 | Viswanathan |
| 7,965,905 B2 | 6/2011 | Allon et al. |
| 7,970,187 B2 | 6/2011 | Puts |
| 7,978,916 B2 | 7/2011 | Klingensmith |
| 7,992,100 B2 | 8/2011 | Lundstrom |
| 8,025,622 B2 | 9/2011 | Rold et al. |
| 8,029,447 B2 | 10/2011 | Kanz |
| 8,052,605 B2 | 11/2011 | Muller |
| 8,055,327 B2 | 11/2011 | Strommer et al. |
| 8,077,939 B2 | 12/2011 | Le Bezet et al. |
| 8,080,474 B2 | 12/2011 | Chen |
| 8,086,000 B2 | 12/2011 | Weijers |
| 8,126,241 B2 | 2/2012 | Zarkh et al. |
| 8,155,411 B2 | 4/2012 | Hof |
| 8,157,742 B2 | 4/2012 | Taylor |
| 8,165,361 B2 | 4/2012 | Li |
| 8,172,763 B2 | 5/2012 | Nelson |
| 8,189,886 B2 | 5/2012 | Huo et al. |
| 8,199,981 B2 | 6/2012 | Koptenko et al. |
| 8,200,040 B2 | 6/2012 | Pfister |
| 8,208,995 B2 * | 6/2012 | Tearney ............... A61B 5/0062 600/476 |
| 8,213,676 B2 | 7/2012 | Bendall |
| 8,233,718 B2 | 7/2012 | Klingensmith |
| 8,260,395 B2 | 9/2012 | Markowitz et al. |
| 8,271,068 B2 | 9/2012 | Khamene |
| 8,275,201 B2 | 9/2012 | Rangawala et al. |
| 8,289,284 B2 | 10/2012 | Glynn |
| 8,295,577 B2 | 10/2012 | Zarkh et al. |
| 8,298,147 B2 * | 10/2012 | Huennekens .......... A61B 6/504 382/128 |
| 8,303,503 B2 | 11/2012 | Nair |
| 8,364,242 B2 | 1/2013 | Li |
| 8,396,276 B2 | 3/2013 | Gatta |
| 8,396,533 B2 | 3/2013 | Barbu et al. |
| 8,409,098 B2 | 4/2013 | Olson |
| 8,411,927 B2 | 4/2013 | Chang et al. |
| 8,428,318 B2 | 4/2013 | Zhuo |
| 8,428,691 B2 | 4/2013 | Byrd |
| 8,433,115 B2 | 4/2013 | Chen |
| 8,457,374 B2 | 6/2013 | Lendl |
| 8,478,387 B2 | 7/2013 | Xu |
| 8,483,488 B2 | 7/2013 | Richter |
| 8,515,146 B2 | 8/2013 | Zhu et al. |
| 8,565,859 B2 | 10/2013 | Wang et al. |
| 8,605,976 B2 | 12/2013 | Diamant et al. |
| 8,625,865 B2 | 1/2014 | Zarkh et al. |
| 8,700,128 B2 | 4/2014 | Assis et al. |
| 8,731,642 B2 | 5/2014 | Zarkh et al. |
| 8,861,830 B2 | 10/2014 | Brada et al. |
| 2001/0031919 A1 | 10/2001 | Strommer et al. |
| 2001/0055418 A1 | 12/2001 | Nakamura |
| 2002/0049375 A1 | 4/2002 | Strommer et al. |
| 2002/0058869 A1 | 5/2002 | Axelsson et al. |
| 2002/0090119 A1 | 7/2002 | Saito et al. |
| 2002/0114497 A1 | 8/2002 | Wetzel et al. |
| 2002/0188307 A1 | 12/2002 | Pintor et al. |
| 2002/0193686 A1 | 12/2002 | Gilboa |
| 2003/0014100 A1 | 1/2003 | Maria Meens et al. |
| 2003/0018251 A1 | 1/2003 | Solomon |
| 2003/0021381 A1 | 1/2003 | Koppe et al. |
| 2003/0023141 A1 | 1/2003 | Stelzer et al. |
| 2003/0069499 A1 | 4/2003 | Lienard et al. |
| 2003/0088179 A1 | 5/2003 | Seeley et al. |
| 2003/0095710 A1 | 5/2003 | Tessadro |
| 2003/0139772 A1 | 7/2003 | Fisher et al. |
| 2003/0157073 A1 | 8/2003 | Peritt |
| 2004/0034380 A1 | 2/2004 | Woolfson et al. |
| 2004/0077941 A1 | 4/2004 | Reddy et al. |
| 2004/0097805 A1 | 5/2004 | Verard et al. |
| 2004/0133129 A1 | 7/2004 | Harari et al. |
| 2004/0165756 A1 | 8/2004 | Mielekamp |
| 2004/0176681 A1 | 9/2004 | Mao et al. |
| 2004/0215235 A1 | 10/2004 | Jackson et al. |
| 2004/0249270 A1 | 12/2004 | Kondo et al. |
| 2004/0254570 A1 | 12/2004 | Hadjicostis et al. |
| 2004/0267113 A1 | 12/2004 | Thomson |
| 2005/0004503 A1 | 1/2005 | Samson et al. |
| 2005/0008210 A1 | 1/2005 | Evron et al. |
| 2005/0015009 A1 | 1/2005 | Mourad et al. |
| 2005/0031176 A1 | 2/2005 | Hertel |
| 2005/0033199 A1 | 2/2005 | van der Steen |
| 2005/0043614 A1 | 2/2005 | Huizenga et al. |
| 2005/0054916 A1 | 3/2005 | Mostafavi |
| 2005/0067568 A1 | 3/2005 | Harding et al. |
| 2005/0080336 A1 | 4/2005 | Byrd et al. |
| 2005/0090737 A1 | 4/2005 | Burrel et al. |
| 2005/0096589 A1 | 5/2005 | Shachar |
| 2005/0107688 A1 | 5/2005 | Strommer |
| 2005/0107808 A1 | 5/2005 | Evans et al. |
| 2005/0111719 A1 | 5/2005 | Pescatore et al. |
| 2005/0113685 A1 | 5/2005 | Maschke et al. |
| 2005/0137661 A1 | 6/2005 | Sra |
| 2005/0141766 A1 | 6/2005 | Nagahashi et al. |
| 2005/0143777 A1 | 6/2005 | Sra |
| 2005/0154281 A1 | 7/2005 | Xue et al. |
| 2005/0182295 A1 | 8/2005 | Soper et al. |
| 2005/0197557 A1 | 9/2005 | Strommer et al. |
| 2005/0197559 A1 | 9/2005 | Boese et al. |
| 2005/0197566 A1 | 9/2005 | Strommer et al. |
| 2005/0201510 A1 | 9/2005 | Mostafavi |
| 2005/0228359 A1 | 10/2005 | Doyle |
| 2005/0234331 A1 | 10/2005 | Sendai |
| 2005/0273050 A1 | 12/2005 | Yokoyama et al. |
| 2005/0288577 A1 | 12/2005 | Weese |
| 2006/0007188 A1 | 1/2006 | Reiner |
| 2006/0058647 A1 | 3/2006 | Strommer et al. |
| 2006/0074285 A1 | 4/2006 | Zarkh et al. |
| 2006/0106318 A1 | 5/2006 | Davidson |
| 2006/0120581 A1 | 6/2006 | Eck et al. |
| 2006/0129142 A1 | 6/2006 | Reynolds |
| 2006/0147897 A1 | 7/2006 | Grinvald |
| 2006/0149134 A1 | 7/2006 | Soper et al. |
| 2006/0155327 A1 | 7/2006 | Briganti et al. |
| 2006/0159318 A1 | 7/2006 | Alyassin et al. |
| 2006/0165270 A1 | 7/2006 | Borgert et al. |
| 2006/0173287 A1 | 8/2006 | Sabszynski et al. |
| 2006/0184016 A1 | 8/2006 | Glossop |

(56) References Cited

U.S. PATENT DOCUMENTS

| | | |
|---|---|---|
| 2006/0188135 A1 | 8/2006 | Zarkh et al. |
| 2006/0193505 A1 | 8/2006 | Glukhovsky et al. |
| 2006/0224188 A1 | 10/2006 | Libbus et al. |
| 2006/0224232 A1 | 10/2006 | Chobotov |
| 2006/0241369 A1 | 10/2006 | Lienard et al. |
| 2006/0241445 A1 | 10/2006 | Altmann |
| 2006/0241465 A1 | 10/2006 | Huennekens et al. |
| 2006/0241478 A1 | 10/2006 | Lewis |
| 2006/0253024 A1 | 11/2006 | Altmann |
| 2006/0253029 A1 | 11/2006 | Altmann |
| 2006/0253031 A1 | 11/2006 | Altmann |
| 2006/0257006 A1 | 11/2006 | Bredno et al. |
| 2006/0259137 A1 | 11/2006 | Artof et al. |
| 2006/0269108 A1 | 11/2006 | Viswanathan |
| 2006/0287595 A1 | 12/2006 | Maschke |
| 2007/0021816 A1 | 1/2007 | Rudin |
| 2007/0038061 A1 | 2/2007 | Huennekens et al. |
| 2007/0038081 A1 | 2/2007 | Eck et al. |
| 2007/0043292 A1 | 2/2007 | Camus |
| 2007/0053558 A1 | 3/2007 | Puts et al. |
| 2007/0055128 A1 | 3/2007 | Glossop |
| 2007/0060798 A1 | 3/2007 | Krupnik et al. |
| 2007/0088431 A1 | 4/2007 | Bourang et al. |
| 2007/0106146 A1 | 5/2007 | Altmann et al. |
| 2007/0116342 A1 | 5/2007 | Zarkh et al. |
| 2007/0123771 A1 | 5/2007 | Redel et al. |
| 2007/0142907 A1 | 6/2007 | Moaddeb et al. |
| 2007/0147706 A1 | 6/2007 | Sasaki et al. |
| 2007/0165916 A1 | 7/2007 | Cloutier et al. |
| 2007/0173861 A1 | 7/2007 | Strommer |
| 2007/0208388 A1 | 9/2007 | Jahns |
| 2007/0219630 A1 | 9/2007 | Chu |
| 2007/0232896 A1 | 10/2007 | Gilboa et al. |
| 2007/0248253 A1 | 10/2007 | Manzke et al. |
| 2007/0255139 A1 | 11/2007 | Deschinger |
| 2007/0269135 A1 | 11/2007 | Ono |
| 2007/0276216 A1 | 11/2007 | Beyar et al. |
| 2008/0008366 A1 | 1/2008 | Desh |
| 2008/0015677 A1 | 1/2008 | Glossop et al. |
| 2008/0021331 A1 | 1/2008 | Grinvald |
| 2008/0082049 A1 | 4/2008 | Evans et al. |
| 2008/0089566 A1 | 4/2008 | Node-Langlois |
| 2008/0114238 A1 | 5/2008 | Lloyd |
| 2008/0118117 A1 | 5/2008 | Gauldie et al. |
| 2008/0119922 A1 | 5/2008 | Alkhatib |
| 2008/0137923 A1 | 6/2008 | Spahn |
| 2008/0137935 A1 | 6/2008 | Spahn |
| 2008/0146923 A1 | 6/2008 | Mejia |
| 2008/0146942 A1 | 6/2008 | Dala-Krishna |
| 2008/0177183 A1 | 7/2008 | Courtney |
| 2008/0188739 A1 | 8/2008 | Rongen et al. |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2008/0247621 A1 | 10/2008 | Zarkh et al. |
| 2008/0253686 A1 | 10/2008 | Bayer |
| 2008/0262346 A1 | 10/2008 | Assis et al. |
| 2008/0267475 A1 | 10/2008 | Lendl |
| 2008/0283771 A1 | 11/2008 | Li |
| 2008/0300487 A1 | 12/2008 | Govari |
| 2009/0016587 A1 | 1/2009 | Strobel et al. |
| 2009/0074284 A1 | 3/2009 | Zeineh et al. |
| 2009/0093676 A1 | 4/2009 | Davidson |
| 2009/0103682 A1 | 4/2009 | Chen et al. |
| 2009/0105579 A1 | 4/2009 | Garibaldi |
| 2009/0116715 A1 | 5/2009 | Bredno et al. |
| 2009/0171201 A1 | 7/2009 | Olson |
| 2009/0177444 A1 | 7/2009 | Wiemker et al. |
| 2009/0216112 A1 | 8/2009 | Assis et al. |
| 2009/0245601 A1 | 10/2009 | Cohen et al. |
| 2009/0257631 A1 | 10/2009 | Baumgart |
| 2009/0264752 A1 | 10/2009 | Markowitz et al. |
| 2009/0264753 A1 | 10/2009 | Von Schulthes |
| 2009/0275831 A1 | 11/2009 | Hall |
| 2009/0281418 A1 | 11/2009 | Ruijters et al. |
| 2009/0299195 A1 | 12/2009 | Muller et al. |
| 2009/0304593 A1 | 12/2009 | Frinking et al. |
| 2009/0306547 A1 | 12/2009 | Iddan et al. |
| 2010/0041949 A1 | 2/2010 | Tolkowsky |
| 2010/0049034 A1 | 2/2010 | Eck et al. |
| 2010/0054573 A1 | 3/2010 | Shekhara |
| 2010/0067768 A1 | 3/2010 | Ionasec et al. |
| 2010/0094124 A1 | 4/2010 | Schoonenberg et al. |
| 2010/0094127 A1 | 4/2010 | Xu |
| 2010/0099979 A1 | 4/2010 | Schoonenberg et al. |
| 2010/0111396 A1 | 5/2010 | Boucheron |
| 2010/0114289 A1 | 5/2010 | Camus |
| 2010/0123715 A1 | 5/2010 | Hansegard |
| 2010/0134517 A1 | 6/2010 | Saikaly et al. |
| 2010/0135546 A1 | 6/2010 | Cziria |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161022 A1 | 6/2010 | Tolkowsky |
| 2010/0161023 A1 | 6/2010 | Cohen et al. |
| 2010/0171819 A1 | 7/2010 | Tolkowsky et al. |
| 2010/0172556 A1 | 7/2010 | Cohen et al. |
| 2010/0174192 A1 | 7/2010 | Azuma |
| 2010/0191102 A1 | 7/2010 | Steinberg et al. |
| 2010/0198063 A1 | 8/2010 | Huber |
| 2010/0220917 A1 | 9/2010 | Steinberg et al. |
| 2010/0222671 A1 | 9/2010 | Cohen et al. |
| 2010/0228076 A1 | 9/2010 | Blank et al. |
| 2010/0246910 A1 | 9/2010 | Wiemker |
| 2010/0272340 A1 | 10/2010 | Bar-Aviv et al. |
| 2010/0290693 A1 | 11/2010 | Cohen et al. |
| 2010/0310140 A1 | 12/2010 | Schneider |
| 2010/0312100 A1 | 12/2010 | Zarkh et al. |
| 2010/0318115 A1 | 12/2010 | Chanduszko et al. |
| 2010/0331670 A1 | 12/2010 | Strommer et al. |
| 2011/0015520 A1 | 1/2011 | Meetz et al. |
| 2011/0026786 A1 | 2/2011 | Mohamed |
| 2011/0033094 A1 | 2/2011 | Zarkh |
| 2011/0034801 A1 | 2/2011 | Baumgart |
| 2011/0052030 A1 | 3/2011 | Bruder et al. |
| 2011/0071404 A1 | 3/2011 | Schmidtt et al. |
| 2011/0075912 A1 | 3/2011 | Rieber et al. |
| 2011/0087104 A1 | 4/2011 | Moore |
| 2011/0112398 A1 | 5/2011 | Zarkh et al. |
| 2011/0118825 A1 | 5/2011 | Hunter et al. |
| 2011/0157154 A1 | 6/2011 | Bernard et al. |
| 2011/0228992 A1 | 9/2011 | Wels et al. |
| 2011/0230758 A1 | 9/2011 | Eichler |
| 2011/0235889 A1 | 9/2011 | Spahn |
| 2011/0286627 A1 | 11/2011 | Takacs et al. |
| 2011/0293163 A1 | 12/2011 | Kargar et al. |
| 2011/0319752 A1 | 12/2011 | Steinberg et al. |
| 2012/0004529 A1 | 1/2012 | Tolkowsky et al. |
| 2012/0004533 A1 | 1/2012 | Peng |
| 2012/0004537 A1* | 1/2012 | Tolkowsky ............ A61B 8/12 600/424 |
| 2012/0014574 A1 | 1/2012 | Ferschel et al. |
| 2012/0029339 A1 | 2/2012 | Cohen et al. |
| 2012/0051606 A1 | 3/2012 | Saikia |
| 2012/0059220 A1 | 3/2012 | Holsing |
| 2012/0059253 A1 | 3/2012 | Wang et al. |
| 2012/0065507 A1 | 3/2012 | Brunke |
| 2012/0069167 A1 | 3/2012 | Liu et al. |
| 2012/0072190 A1 | 3/2012 | Sharma et al. |
| 2012/0083696 A1 | 4/2012 | Kitamura |
| 2012/0093379 A1 | 4/2012 | Florent et al. |
| 2012/0123238 A1 | 5/2012 | Vaillant et al. |
| 2012/0130242 A1 | 5/2012 | Burgess |
| 2012/0140998 A1 | 6/2012 | Zhu |
| 2012/0207367 A1 | 8/2012 | Kneepkens |
| 2012/0215093 A1 | 8/2012 | Ji |
| 2012/0224751 A1 | 9/2012 | Kemp |
| 2012/0230565 A1 | 9/2012 | Steinberg et al. |
| 2012/0245460 A1 | 9/2012 | Slomka |
| 2012/0250974 A1 | 10/2012 | Miyamoto |
| 2012/0294498 A1 | 11/2012 | Popovic |
| 2012/0300981 A1 | 11/2012 | Yeh et al. |
| 2012/0310081 A1 | 12/2012 | Adler et al. |
| 2013/0004044 A1 | 1/2013 | Ross |

(56) References Cited

U.S. PATENT DOCUMENTS

| | | |
|---|---|---|
| 2013/0030295 A1 | 1/2013 | Huennekens |
| 2013/0046167 A1 | 2/2013 | Shah |
| 2013/0053664 A1 | 2/2013 | Jian et al. |
| 2013/0109958 A1 | 5/2013 | Baumgart |
| 2013/0109959 A1 | 5/2013 | Baumgart |
| 2013/0116739 A1 | 5/2013 | Brada et al. |
| 2013/0120296 A1 | 5/2013 | Merritt |
| 2013/0120297 A1 | 5/2013 | Merritt |
| 2013/0123616 A1 | 5/2013 | Merritt |
| 2013/0308844 A1 | 11/2013 | Florent et al. |
| 2013/0329030 A1 | 12/2013 | Tolkowsky et al. |
| 2013/0329977 A1 | 12/2013 | Tolkowsky et al. |
| 2014/0094660 A1 | 4/2014 | Tolkowsky et al. |
| 2014/0094689 A1 | 4/2014 | Cohen et al. |
| 2014/0094690 A1 | 4/2014 | Tolkowsky et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0100451 A1 | 4/2014 | Tolkowsky et al. |
| 2014/0107479 A1 | 4/2014 | Klaiman et al. |
| 2014/0111541 A1 | 4/2014 | Tolkowsky et al. |
| 2014/0112566 A1 | 4/2014 | Steinberg et al. |
| 2014/0114184 A1 | 4/2014 | Klaiman et al. |
| 2014/0114185 A1 | 4/2014 | Tolkowsky et al. |
| 2014/0114308 A1 | 4/2014 | Tolkowsky et al. |
| 2014/0114333 A1 | 4/2014 | Tolkowsky et al. |
| 2014/0121513 A1 | 5/2014 | Tolkowsky et al. |
| 2014/0161331 A1 | 6/2014 | Cohen et al. |
| 2015/0282737 A1 | 10/2015 | Tolkowsky et al. |
| 2015/0282889 A1 | 10/2015 | Cohen et al. |
| 2015/0282890 A1 | 10/2015 | Cohen et al. |
| 2015/0283319 A1 | 10/2015 | Tolkowsky et al. |

FOREIGN PATENT DOCUMENTS

| | | |
|---|---|---|
| WO | 99/07354 A2 | 2/1999 |
| WO | 00/33755 A1 | 6/2000 |
| WO | 01/10313 A1 | 2/2001 |
| WO | 01/43642 | 6/2001 |
| WO | 03/043516 A2 | 5/2003 |
| WO | 03/096894 | 11/2003 |
| WO | 2005/026891 | 3/2005 |
| WO | 2005/051452 A2 | 6/2005 |
| WO | 2005/124689 | 12/2005 |
| WO | 2006/027781 A2 | 3/2006 |
| WO | 2006/066122 | 6/2006 |
| WO | 2006/066124 | 6/2006 |
| WO | 2006/076409 A2 | 7/2006 |
| WO | 2006/114721 A2 | 11/2006 |
| WO | 2006/121984 | 11/2006 |
| WO | 2007/002685 A2 | 1/2007 |
| WO | 2007/014028 A1 | 2/2007 |
| WO | 2007/015199 A2 | 2/2007 |
| WO | 2008/007350 A1 | 1/2008 |
| WO | 2008/062358 A1 | 5/2008 |
| WO | 2008/107905 | 9/2008 |
| WO | 2009/153794 | 12/2009 |
| WO | 2010/058398 A2 | 5/2010 |
| WO | 2011/046903 A2 | 4/2011 |
| WO | 2011/046904 A1 | 4/2011 |
| WO | 2011128797 A1 | 10/2011 |
| WO | 2011/145094 A2 | 11/2011 |
| WO | 2012/014212 A1 | 2/2012 |
| WO | 2012/028190 A1 | 3/2012 |
| WO | 2012095755 A1 | 7/2012 |
| WO | 2012107857 A1 | 8/2012 |
| WO | 2012/138872 A2 | 10/2012 |
| WO | 2012/138874 A2 | 10/2012 |
| WO | 2012/176191 A1 | 12/2012 |
| WO | 2013/025602 A1 | 2/2013 |
| WO | 2013061225 A1 | 5/2013 |
| WO | 2013/084345 A1 | 6/2013 |
| WO | 2013/128233 A1 | 9/2013 |
| WO | 2013/169814 A1 | 11/2013 |
| WO | 2013/175472 A2 | 11/2013 |
| WO | 2014/002095 A2 | 1/2014 |
| WO | 2015/155770 A1 | 10/2015 |

OTHER PUBLICATIONS

An Official Action dated Jul. 6, 2015, which issued during the prosecution of Applicant's U.S. Appl. No. 12/649,955.

An Official Action dated May 19, 2015 which issued during the prosecution of Applicant's U.S. Appl. No. 13/228,229.

An Official Action dated May 21, 2015, which issued during the prosecution of Applicant's U.S. Appl. No. 14/098,140.

An Official Action dated Aug. 4, 2015, which issued during the prosecution of Applicant's U.S. Appl. No. 14/128,243.

An Official Action dated May 21, 2015, which issued during the prosecution of Applicant's Canadian Application No. 2,874,415.

An Official Action dated Jul. 2, 2015, which issued during the prosecution of Applicant's Canadian Application No. 2,875,346.

An English-translation of an Official Action dated Jun. 23, 2015, which issued during the prosecution of Applicant's JP Application No. 2014-164417.

Communication dated Aug. 29, 2014 from the USPTO in U.S. Appl. No. 14/098,140.

Boyle et al., entitled "Assessment of a Novel Angiographic Image Stabilization System for Percutaneous Coronary Intervention" (Journal of Interventional Cardiology, vol. 20 No. 2, 2007.

Communication dated Mar. 25, 2015 from the United States Patent and Trademark Office in counterpart U.S. Appl. No. 12/075,252.

Communication dated Apr. 13, 2015 from the United States Patent and Trademark Office in counterpart U.S. Appl. No. 12/649,944.

Communication dated Apr. 22, 2015 from the United States Patent and Trademark Office in counterpart U.S. Appl. No. 14/142,082.

Communication dated Apr. 10, 2015 from the United States Patent and Trademark Office in counterpart U.S. Appl. No. 12/648,913.

Communication dated Apr. 10, 2015 from the United States Patent and Trademark Office in counterpart U.S. Appl. No. 12/650,152.

Communication dated Mar. 16, 2015 from the United States Patent and Trademark Office in counterpart U.S. Appl. No. 13/228,211.

Communication dated Mar. 23, 2015 from the United States Patent and Trademark Office in counterpart U.S. Appl. No. 14/097,922.

Communication dated Mar. 16, 2015 from the United States Patent and Trademark Office in counterpart U.S. Appl. No. 13/228,185.

Communication dated Feb. 23, 2015 from the United States Patent and Trademark Office in counterpart U.S. Appl. No. 14/143,184.

Communication dated May 6, 2015 from the United States Patent and Trademark Office in counterpart U.S. Appl. No. 12/781,260.

Communication dated May 11, 2015 from the United States Patent and Trademark Office in counterpart U.S. Appl. No. 12/650,605.

Communication dated May 12, 2015 from the Japanese Patent Office in counterpart application No. 521284/2013.

Communication dated Dec. 11, 2014, issued by the United States Patent and Trademark Office in corresponding U.S. Appl. No. 12/648,913.

Communication dated Feb. 4, 2015, issued by the United States Patent and Trademark Office in corresponding U.S. Appl. No. 12/649,955.

Communication dated Nov. 24, 2014, issued by the United States Patent and Trademark Office in corresponding U.S. Appl. No. 12/781,260.

Communication dated Jan. 6, 2015, issued by the United States Patent and Trademark Office in corresponding U.S. Appl. No. 12/650,605.

Communication dated Feb. 6, 2015, issued by the United States Patent and Trademark Office in corresponding U.S. Appl. No. 12/650,121.

Communication dated Nov. 24, 2014, issued by the United States Patent and Trademark Office in corresponding U.S. Appl. No. 12/649,944.

Communication dated Feb. 6, 2015, issued by the United States Patent and Trademark Office in corresponding U.S. Appl. No. 12/781,366.

(56) References Cited

OTHER PUBLICATIONS

Communication dated Jan. 16, 2015, issued by the United States Patent and Trademark Office in corresponding U.S. Appl. No. 13/228,229.
Communication dated Jan. 6, 2015, issued by the United States Patent and Trademark Office in corresponding U.S. Appl. No. 13/228,335.
Communication dated Nov. 28, 2014, issued by the United States Patent and Trademark Office in corresponding U.S. Appl. No. 14/097,922.
Communication dated Dec. 4, 2014, issued by the United States Patent and Trademark Office in corresponding U.S. Appl. No. 14/098,114.
Communication dated Nov. 24, 2014, issued by the United States Patent and Trademark Office in corresponding U.S. Appl. No. 12/650,156.
Communication dated Dec. 19, 2014, issued by the United States Patent and Trademark Office in corresponding U.S. Appl. No. 14/143,430.
Communication dated Jan. 12, 2015, issued by the United States Patent and Trademark Office in corresponding U.S. Appl. No. 14/143,289.
Communication dated Jan. 23, 2015, issued by the European Patent Office in counterpart Application No. 12802046.8.
Communication dated Sep. 5, 2014 from the USPTO in U.S. Appl. No. 14/143,289.
Communication dated Oct. 24, 2014 from the USPTO in U.S. Appl. No. 12/650,121.
Communication dated Aug. 29, 2014 from the USPTO in U.S. Appl. No. 14/098,14.
Communication dated Nov. 7, 2014 from the USPTO in U.S. Appl. No. 14/096,968.
Communication dated Sep. 5, 2014 from the USPTO in U.S. Appl. No. 14/143,430.
Communication dated Sep. 11, 2014 from the USPTO in U.S. Appl. No. 12/650,152.
Communication dated Oct. 15, 2014 from the USPTO in U.S. Appl. No. 12/781,366.
Communication dated Oct. 8, 2014 from the USPTO in U.S. Appl. No. 14/098,093.
Communication dated Oct. 14, 2014 from the USPTO in U.S. Appl. No. 12/075,252.
Official Action dated Oct. 31, 2012, which issued during the prosecution U.S. Appl. No. 12/075,244.
Official Action dated Sep. 20, 2012, which issued during the prosecution of U.S. Appl. No. 12/649,955.
U.S. Appl. No. 61/359,431.
W. Goodman et al., "Coronary-Artery Calcification in Young Adults With End-Stage Renal Disease Who Are Undergoing Dialysis," The New England Journal of Medicine, vol. 342 No. 20.
W. Leung et al., "Coronary Artery Quantitation and Data Management System for Paired Cineangiograms," Catheterization and Cardiovascular Diagnosis 24:121-134 (1991).
A search report dated Nov. 23, 2012, which issued during the prosecution of Applicant's EP Application 09 827264.4-1265/2358269.
An examination report dated Dec. 5, 2012, which issued during the prosecution of Applicant's EP Application 09766329.8.
An Official Action dated Dec. 10, 2012, which issued during the prosecution of Applicant's U.S. Appl. No. 12/650,156.
An Official Action dated Dec. 11, 2012, which issued during the prosecution of Applicant's U.S. Appl. No. 12/650,152.
An Official Action dated Jan. 22, 2013, which issued during the prosecution of Applicant's U.S. Appl. No. 12/650,121.
An Official Action dated Jan. 28, 2013, which issued during the prosecution of Applicant's U.S. Appl. No. 12/781,366.
An Official Action dated Feb. 4, 2013, which issued during the prosecution of Applicant's U.S. Appl. No. 13/228,185.
Peng Wang et al.: "Image-Based Device Tracking for the Co-registration of Angiography and Intravascular Ultrasound Images", MICCAI 2011, Part I, LINCS 6891, pp. 161-168, 2011.

An Official Action dated Jul. 2, 2013, which issued during the prosecution of Applicant's U.S. Appl. No. 12/075,244.
An Official Action dated Jun. 19, 2013, which issued during the prosecution of Applicant's U.S. Appl. No. 12/075,214.
An Official Action dated May 31, 2013, which issued during the prosecution of Applicant's U.S. Appl. No. 12/075,252.
An Official Action dated May 6, 2013, which issued during the prosecution of Applicant's U.S. Appl. No. 12/487,315.
A Notice of Allowance dated Jun. 4, 2013, which issued in Applicant's U.S. Appl. No. 12/649,960.
An Official Action dated Sep. 6, 2013, which issued during the prosecution of Applicant's U.S. Appl. No. 12/650,605.
An Official Action dated Aug. 30, 2013, which issued during the prosecution of Applicant's U.S. Appl. No. 12/650,121.
An Official Action dated Sep. 12, 2013, which issued during the prosecution of Applicant's U.S. Appl. No. 12/781,260.
A Notice of Allowance in Applicant's U.S. Appl. No. 12/781,414.
An Official Action dated Aug. 3, 2012, which issued during the prosecution of Applicant's U.S. Appl. No. 12/781,294.
An Official Action dated Jun. 19, 2012, which issued during the prosecution of Applicant's U.S. Appl. No. 12/075,252.
An Official Action dated Jun. 18, 2012, which issued during the prosecution of Applicant's U.S. Appl. No. 12/781,366.
An Official Action dated Jun. 7, 2012, which issued during the prosecution of Applicant's U.S. Appl. No. 12/650,156.
An Official Action dated May 29, 2012, which issued during the prosecution of Applicant's U.S. Appl. No. 12/650,121.
Buddy D. Ratner, "Biomaterials Science: An Introduction to Materials in Medicine", Elsevier, chapter 7, 1996.
Gerald E. Miller, "Fundamentals of Biomedical Transport Processes, Morgan & Claypool Publishers", chapter 2, 2010.
Gerhard Albert ten Brinke, "Automated coronary flow reserve assessment using planar x-ray angiography", PhD dissertation, Universiteit Twente, 2011.
Jerry T. Wong et al., "Quantification of fractional flow reserve based on angiographic image data", Int J Cardiovasc Imaging 28:13-22, Jan. 7, 2011.
Kassab, G. S. et al., "Cross-sectional area and volume compliance of porcine left coronary arteries," Am. J. Physiol. Heart Circ. Physiol. 281, H623-H628, Aug. 2011.
Molloi S. et al., "Absolute volumetric coronary blood flow measurement with digital subtraction angiography". Int J Card Imaging 14:137-145, 1998.
Molloi, S. et al., "Estimation of coronary artery hyperemic blood flow based on arterial lumen volume using angiographic images," The International Journal of Cardiovascular Imaging, vol. 28, No. 1, 1-11, Jan. 7, 2011.
A Notice of Allowance dated Jun. 24, 2014, issued in Applicant's U.S. Appl. No. 14/097,603.
An Official Action dated Jul. 3, 2014, which issued during the prosecution of Applicant's U.S. Appl. No. 12/648,913.
An Official Action dated Jul. 30, 2014, which issued during the prosecution of Applicant's U.S. Appl. No. 12/075,214.
An Official Action dated Jul. 31, 2014, which issued during the prosecution of Applicant's U.S. Appl. No. 12/649,944.
An Official Action dated Jun. 18, 2014, which issued during the prosecution of Applicant's U.S. Appl. No. 12/075,244.
An Official Action dated May 21, 2014, which issued during the prosecution of Applicant's U.S. Appl. No. 12/650,156.
An Official Action dated May 29, 2014, which issued during the prosecution of Applicant's U.S. Appl. No. 14/097,922.
An Official Action dated May 30, 2014, which issued during the prosecution of Applicant's U.S. Appl. No. 13/228,335.
An Official Action dated Jun. 3, 2014, which issued during the prosecution of Applicant's U.S. Appl. No. 12/781,260.
An Official Action dated Feb. 20, 2014, which issued during the prosecution of Applicant's U.S. Appl. No. 12/075,214.
An Official Action dated May 6, 2014, which issued during the prosecution of Applicant's U.S. Appl. No. 12/075,252.
A Notice of Allowance issued in Applicant's U.S. Appl. No. 12/666,879.
An Official Action dated Mar. 21, 2014, which issued during the prosecution of Applicant's U.S. Appl. No. 12/648,913.

(56) References Cited

OTHER PUBLICATIONS

An Official Action dated Apr. 3, 2014, which issued during the prosecution of Applicant's U.S. Appl. No. 12/649,955.
An Official Action dated Mar. 14, 2014, which issued during the prosecution of Applicant's U.S. Appl. No. 12/650,605.
An Official Action dated Apr. 25, 2014, which issued during the prosecution of Applicant's U.S. Appl. No. 12/650,121.
An Official Action dated Apr. 24, 2014, which issued during the prosecution of Applicant's U.S. Appl. No. 12/781,366.
An Official Action dated Apr. 17, 2014, which issued during the prosecution of Applicant's U.S. Appl. No. 13/228,211.
An Official Action dated Apr. 28, 2014, which issued during the prosecution of Applicant's U.S. Appl. No. 13/228,185.
An Official Action dated May 5, 2014, which issued during the prosecution of Applicant's U.S. Appl. No. 14/096,968.
An Official Action dated Feb. 14, 2014, which issued during the prosecution of Applicant's U.S. Appl. No. 14/098,140.
Pyxaras et al., "Quantitative angiography optical coherence tomography for the functional assessment of nonobstructive coronary stenoses" (Medscape), Oct. 2013, 11 pages total.
Tu et al., "In vivo comparison of arterial lumen dimensions assessed by co-registered 3D quantitative coronary angiography intravascular ultrasound and optical coherence tomography.", Int J Cardiovasc Imaging (2012) 28:1315-1327, Jan. 20, 2012, DOI 10.1007/s10554-012-0016-6, 13 pages total.
Tu et al, "Fusion of 3D QCA and IVUS/OCT", Int J Cardiovasc Imaging (2011) 27:197-207, Jan. 25, 2011, DOI 10.1007/s10554-011-9809-2, 11 pages total.
Boyle et al., entitled "Assessment of a Novel Angiographic Image Stabilization System for Percutaneous Coronary Intervention" (Journal of Interventional Cardiology, vol. 20 No. 2, 2007.
Timinger et al., entitled "Motion compensated coronary interventional navigation by means of diaphragm tracking and elastic motion models" (Phys Med Biol. Feb. 7, 2005;50(3):491-503.
Timinger et al., entitled "Motion compensation for interventional navigation on 3D static roadmaps based on an affine model and gating" (Phys Med Biol. Mar. 7, 2004;49(5):719-32.
Turski et al., entitled "Digital Subtraction Angiography 'Road Map'" (American Journal of Roentgenology, 1982.
Iddan et al., entitled "3D imaging in the studio and elsewhere" (SPIE Proceedings vol. 4298, 2001.
"Catheter Insertion Simulation with Combined Visual and Haptic Feedback," by Zorcolo et al. (Center for Advanced Studies, Research and Development in Sardinia).
"4D-CT imaging of a volume influenced by respiratory motion on multi-slice CT Tinsu Pan," by Lee et al., (Medical Physics, Feb. 2004, vol. 31, Issue 2, pp. 333-340)—an abstract.
"New 4-D imaging for real-time intraoperative MRI: adaptive 4-D scan," by Tokuda et al. (Med Image Comput Assist Intent Int Conf. 2006;9(Pt 1):454-61) an abstract.
"Real-time interactive viewing of 4D kinematic MR joint studies," by Schulz et al. (Med Image Comput Assist Intent Int Conf. 2005;8(Pt 1):467-73.)—an abstract.
"4D smoothing of gated SPECT images using a left-ventricle shape model and a deformable mesh," by Brankov et al., (Nuclear Science Symposium Conference Record, 2004 IEEE, Oct. 2004, vol. 5, 2845-2848).
"Prospective motion correction of X-ray images for coronary interventions," by Shechter et al. (IEEE Trans Med Imaging. Apr. 2005;24(4):441-50).
"Cardiac Imaging: We Got the Beat!" by Elizabeth Morgan (Medical Imaging, Mar. 2005).
"Noninvasive Coronary Angiography by Retrospectively ECG-Gated Multislice Spiral CT," by Achenbach et al., (Circulation. Dec. 5, 2000;102(23):2823-8).
"Spatially-adaptive temporal smoothing for reconstruction of dynamic and gated image sequences," by Brankov et al., (Nuclear Science Symposium Conference Record, 2000 IEEE, 2000, vol. 2, 15/146-15/150)—an abstract.

"Full-scale clinical implementation of a video based respiratory gating system," by Ramsey et al., (Engineering in Medicine and Biology Society, 2000. Proceedings of the 22nd Annual International Conference of the IEEE, 2000, vol. 3, 2141-2144)—an abstract.
"Three-Dimensional Respiratory-Gated MR Angiography of the Coronary Arteries: Comparison with Conventional Coronary Angiography," by Post et al., (AJR, 1996; 166: 1399-1404).
Soffie Mansson, et al., "Dosimetric verification of breathing adapted radiotherapy using polymer gel", Journal of Physics: Conference series 56 (200) 300-303.
"From 2D to 4D" AXIOM Innovations—Mar. 2008, www.siemens.com/healthcare-magazine.
A Brochure: Impella® 2.5, Percutaneous Circulatory Support System, ABIOMED™, 2007.
Frangi et al., entitled "Multiscale vessel enhancement filtering" (Medical Image Computing and Computer Assisted Intervention—MICCAI 1998—Lecture Notes in Computer Science, vol. 1496, Springer Verlag, Berlin, Germany, pp. 130-137).
Dijkstra, entitled "A Note on Two Problems in Connexion with Graphs" (Numerische Mathematik I, 269-271, 1959).
Zarkh et al., entitled "Guide wire navigation and therapeutic device localization for catheterization procedure" (International Congress Series 1281 (2005) 311-316.
Brochure: At the Transvascular Cardiovascular Therapeutics (TCT) conference held in Washington DC, USA in Oct. 2008, Paieon Inc. demonstrated the CardiOp-THV system for real-time navigation and positioning of a trans-catheter heart valve.
Brochure: At the TCT conference held in San Francisco, USA in Sep. 2009, Paieon Inc. demonstrated the IC-PRO Comprehensive Imaging Workstation for providing assistance in cardiac catheterization procedures.
An International Search Report dated Sep. 8, 2009, which issued during the prosecution of Applicant's PCT/IL09/00610.
An International Search Report dated Jan. 15, 2009, issued during the prosecution of Applicant's PCT Patent Application No. PCT/IL08/000316.
An International Search Report dated May 19, 2010 issued during the prosecution of Applicant's PCT Patent Application No. PCT/IL2009/001089.
"A new point matching algorithm for non-rigid registration," by Chui (Computer Vision and Image Understanding 89 (2003) 114-141).
"Advanced and Challenges in Super-Resolution," by Farsiu (International Journal of Imaging Systems and Technology, vol. 14, No. 2, pp. 47-57, Special issue on high-resolution image reconstruction, Aug. 2004).
"Image Registration by Minimization of Residual Complexity," by Myronenko (CVPR 2009).
"Image inpainting," by Bertalmio (ACM Siggraph 2000, New Orleans, Louisiana, USA, Jul. 2000).
"Nonrigid registration using free-form deformations: application to breast MR images," by Rueckert, (IEEE Trans. Med. Img, vol. 18, No. 8, 1999).
"Unwarping of unidirectionally distorted EPI images," by Kybic (IEEE Trans. Med. Img., vol. 19, No. 2, 2000).
"Geometrically Correct 3-D Reconstruction of Intravascular Ultrasound Images by Fusion with Biplane Angiography—Methods and Validation," Andreas Wahle, IEEE Transactions on Medical Imaging, Final Manuscript #187/98, Jun. 30, 1999.
An International Search Report dated Jan. 6, 2012, which issued during the prosecution of Applicant's PCT Application No. PCT/IL11/00391.
An Official Action dated Nov. 28, 2011, which issued during the prosecution of Applicant's U.S. Appl. No. 12/075,252.
An Official Action dated Dec. 8, 2011, which issued during the prosecution of Applicant's U.S. Appl. No. 12/075,244.
U.S. Appl. No. 60/845,347 to Strommer et al., filed Sep. 2006.
International Search Report dated Mar. 2, 2012, issued in PCT/IL11/00612.
Office Action dated Mar. 14, 2012, issued in U.S. Appl. No. 12/075,214.
Office Action dated Mar. 15, 2012, issued in U.S. Appl. No. 12/649,944.

(56) References Cited

OTHER PUBLICATIONS

Office Action dated Mar. 15, 2012, issued in U.S. Appl. No. 12/650,152.
Office Action dated May 22, 2012, issued in U.S. Appl. No. 12/075,244.
Umeda, H. et al., "Promising efficacy of primary gradual and prolonged balloon angioplasty in small coronary arteries: A randomized comparison with cutting balloon angioplasty and conventional balloon angioplasty", 2004.
W. Santamore et al., "A microcomputer based automated quantative coronary angiographic analysis system," Annals of Biomedical Engineering, vol. 16, pp. 367-377, 1988.
V. Duddalwar, "Multislice CT angiography: a practical guide to CT angiography in vascular imaging and intervention," The British Journal of Radiology, 77 (2004), S27-S38.
Official Action dated Oct. 23, 2012, which issued during the prosecution of JP Application No. 2009-552328.
Official Action dated Nov. 23, 2012, which issued during the prosecution of U.S. Appl. No. 12/649,944.
Official Action dated Aug. 27, 2012, which issued during the prosecution U.S. Appl. No. 12/075,214.
International Search Report dated Oct. 10, 2012, which issued during the prosecution of PCT/IL2012/000246.
Communication dated Sep. 5, 2012, which issued during the prosecution of EP Application 09 766 329.8-1526.
Communication dated Oct. 29, 2012, which issued during the prosecution of EP Application 08 719941.0-1265/2129284.
Computer translation of JP 2010-253017 to Takeshi.
G. Mancini et al., "Automated quantitative coronary arteriography: morphologic and physiologic validation in vivo of a rapid digital angiographic method," Circulation 1987;75:452-460.
I. Kompatsiaris et al., "Deformable Boundary Detection of Stents in Angiographic Images," IEEE Transactions on Medical Imaging, vol. 19, No. 6, Jun. 2000.
L. Yaneza et al., "Atherosclerotic Plaque Can Be Quantified Using Multifractal and Wavelet Decomposition Techniques," Abstracts—Angiography & Interventional Cardiology, JACC Mar. 3, 2004.
Molloi, S. et al., "Quantification of coronary artery lumen volume by digital angiography: in vivo validation," Circulation 104, 2351-2357, Nov. 6, 2001.
Molloi, S. et al., "Quantification of volumetric coronary blood flow with dual-energy digital subtraction angiography," Circulation 93, 1919-1927, May 15, 1996.
Molloi, S. et al., "Regional volumetric coronary blood flow measurement by digital angiography: in vivo validation," Acad. Radiol. 11, 7, 757-766, Jul. 2004.
Sian Sen et al., "Development and Validation of a New, Adenosine-Independent Index of Stenosis Severity From Coronary Wave—Intensity Analysis". Journal of the American College of Cardiology, vol. 59, Apr. 10, 2012.
Yunlong Huo et al., "A validated predictive model of coronary fractional flow reserve," J. R. Soc. Interface, Nov. 23, 2011.
A Notice of Allowance issued in Applicant's U.S. Appl. No. 13/965,893.
An Official Action dated Nov. 13, 2013, which issued during the prosecution of Applicant's U.S. Appl. No. 12/666,879.
An Official Action dated Oct. 2, 2013, which issued during the prosecution of Applicant's U.S. Appl. No. 13/228,211.
An Official Action dated Oct. 21, 2013, which issued during the prosecution of Applicant's U.S. Appl. No. 12/075,214.
An Official Action dated Oct. 23, 2013, which issued during the prosecution of Applicant's U.S. Appl. No. 12/648,913.
An Official Action dated Oct. 25, 2013, which issued during the prosecution of Applicant's U.S. Appl. No. 12/781,366.
An Official Action dated Oct. 3, 2013, which issued during the prosecution of Applicant's U.S. Appl. No. 13/228,185.
An Official Action dated Oct. 30, 2013, which issued during the prosecution of Applicant's U.S. Appl. No. 13/228,335.
An Official Action dated Oct. 4, 2013, which issued during the prosecution of Applicant's U.S. Appl. No. 12/649,955.
Correspondence from the International Searching Authority in Applicant's PCT/IL13/50549.
Correspondence from the International Searching Authority in Applicant's PCT/IL2013/050438.
International Search Report and Written Opinion for International Patent Application PCT/IL2013/050438 mailed Dec. 2, 2013.
Office Action, dated Jan. 7, 2014, issued by the United States Patent and Trademark Office, in counterpart U.S. Appl. No. 12/075,244.
Office Action, dated Feb. 12, 2014, issued by the United States Patent and Trademark Office, in counterpart U.S. Appl. No. 12/781,260.
Office Action, dated Dec. 31, 2013, issued by the United States Patent and Trademark Office, in counterpart U.S. Appl. No. 12/075,252.
Notice of Allowance, dated Jan. 3, 2014, issued by the United States Patent and Trademark Office, in counterpart U.S. Appl. No. 13/965,872.
Search Report, dated Jan. 22, 2014, issued by the International Searching Authority, in counterpart Application No. PCT/IL13/50549.
Written Opinion, dated Jan. 22, 2014, issued by the International Searching Authority, in counterpart Application No. PCT/IL13/50549.
An Official Action dated Aug. 17, 2015, which issued during the prosecution of Applicant's U.S. Appl. No. 12/648,913.
An Official Action dated Aug. 27, 2015, which issued during the prosecution of Applicant's U.S. Appl. No. 12/650,121.
An Official Action dated Oct. 22, 2015, which issued during the prosecution of Applicant's U.S. Appl. No. 12/649,944.
An Official Action dated Sep. 11, 2015, which issued during the prosecution of Applicant's U.S. Appl. No. 12/781,260.
An Official Action dated Sep. 21, 2015, which issued during the prosecution of Applicant's U.S. Appl. No. 13/228,229.
An Official Action dated Sep. 3, 2015, which issued during the prosecution of Applicant's U.S. Appl. No. 13/228,211.
An Official Action dated Oct. 7, 2015, which issued during the prosecution of Applicant's U.S. Appl. No. 13/228,185.
An Official Action dated Aug. 11, 2015, which issued during the prosecution of Applicant's U.S. Appl. No. 13/228,335.
An Official Action dated Aug. 12, 2015, which issued during the prosecution of Applicant's U.S. Appl. No. 14/097,922.
An Official Action dated Oct. 7, 2015, which issued during the prosecution of Applicant's U.S. Appl. No. 14/142,082.
An Official Action dated Aug. 25, 2015, which issued during the prosecution of Applicant's U.S. Appl. No. 14/143,184.
A European Patent report dated Sep. 8, 2015, which issued during the prosecution of Applicant's European Patent Application No. 08719941.0.
An Official Action dated Sep. 4, 2015, which issued during the prosecution of Applicant's Canadian Application No. 2,874,415.
An International Search Report and Written Opinion dated Aug. 25, 2015, which issued during prosecution of Applicant's PCT/IL2015/050372.

\* cited by examiner

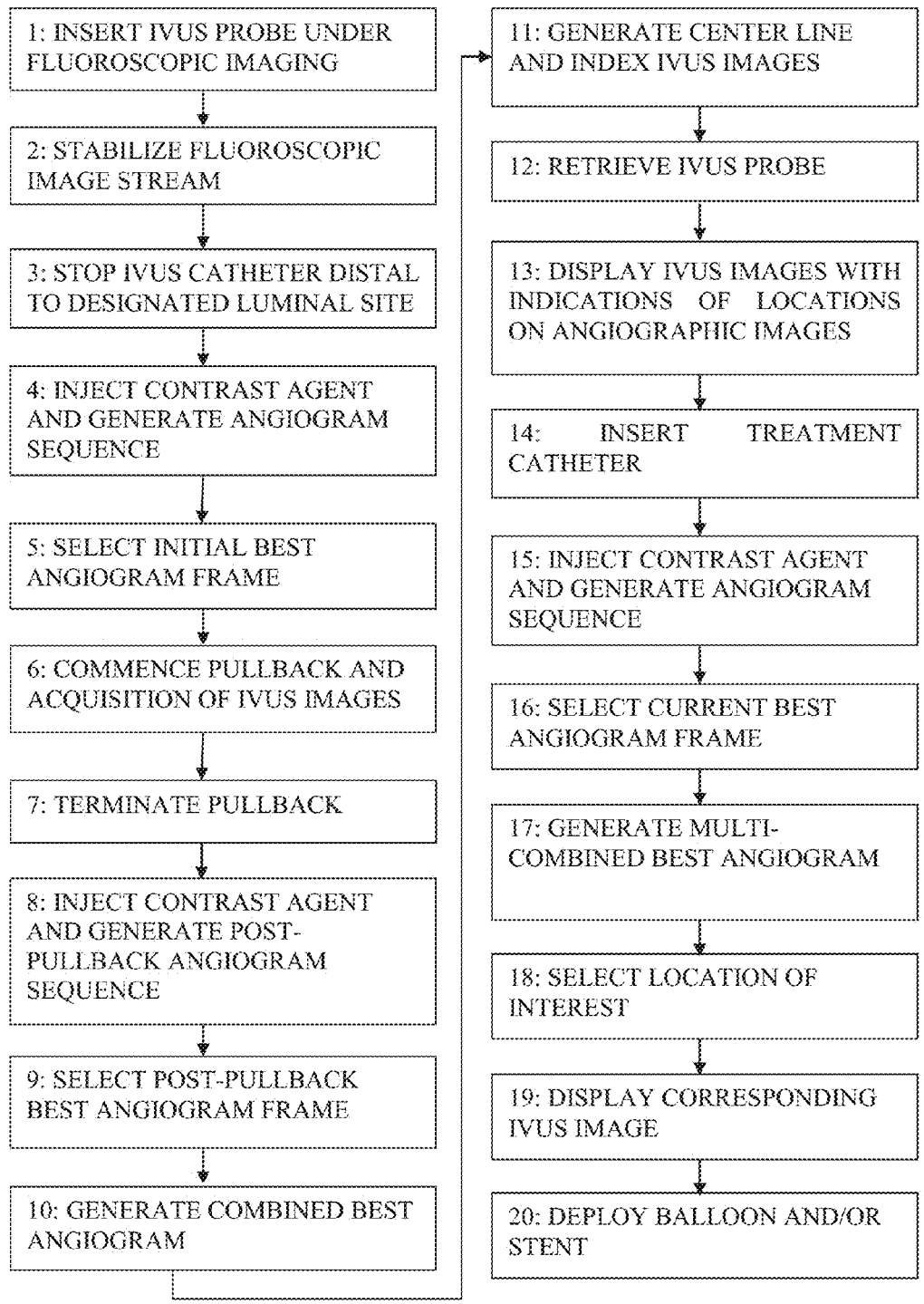

CO-USE OF ENDOLUMINAL DATA AND EXTRALUMINAL IMAGING

CROSS REFERENCES TO RELATED APPLICATIONS

The present application is a continuation of U.S. Ser. No. 13/228,229 to Tolkowsky (published as US 2012/0004537), filed Sep. 8, 2011, which is a continuation of International Application No. PCT/IL2011/000612 to Tolkowsky (published as WO 12/014212), entitled "Co-use of endoluminal data and extraluminal imaging," filed 28 Jul., 2011, which claims the benefit of:

U.S. Provisional Patent Application 61/344,464, entitled "Co-use of endoluminal data and extraluminal imaging," filed 29 Jul. 2010;

U.S. Provisional Patent Application 61/344,875, entitled "Co-use of endoluminal data and extraluminal imaging," filed 1 Nov. 2010;

U.S. Provisional Patent Application 61/457,339, entitled "Co-use of endoluminal data and extraluminal imaging," filed 3 Mar. 2011;

U.S. Provisional Patent Application 61/457,455, entitled "Co-use of endoluminal data and extraluminal imaging," filed 1 Apr. 2011;

U.S. Provisional Patent Application 61/457,780, entitled "Co-use of endoluminal data and extraluminal imaging," filed 2 Jun., 2011; and U.S. Provisional Patent Application 61/457,951, entitled "Co-use of endoluminal data and extraluminal imaging," filed 15 Jul., 2011.

The present application is related to the following patent applications:

U.S. patent application Ser. No. 12/650,605 to Cohen (published as US 2010/0172556), filed Dec. 31, 2009, which:

(i) is a continuation of U.S. patent application Ser. No. 12/666,879 to Steinberg (issued as U.S. Pat. No. 8,781,193), which is the US national phase of PCT Application No. PCT/IL2009/001089 to Cohen (published as WO 10/058398), filed Nov. 18, 2009, which claims priority from the following patent applications:

U.S. Provisional Patent Application 61/193,329, entitled "Apparatuses and methods for the automatic generation of a road map from angiographic images of a cyclically-moving organ," to Steinberg, filed Nov. 18, 2008

U.S. Provisional Patent Application 61/193,915, entitled "Image processing and tool actuation for medical procedures," to Steinberg, filed Jan. 8, 2009

U.S. Provisional Patent Application 61/202,181, entitled "Image processing and tool actuation for medical procedures," to Steinberg, filed Feb. 4, 2009

U.S. Provisional Patent Application 61/202,451, entitled "Image processing and tool actuation for medical procedures," to Steinberg, filed Mar. 2, 2009

U.S. Provisional Patent Application 61/213,216, entitled "Image processing and tool actuation for medical procedures," to Steinberg, filed May 18, 2009

U.S. Provisional Patent Application 61/213,534, entitled "Image Processing and Tool Actuation for Medical Procedures," to Steinberg, filed Jun. 17, 2009

U.S. Provisional Patent Application 61/272,210, entitled "Image processing and tool actuation for medical procedures," to Steinberg, filed Sep. 1, 2009 and U.S. Provisional Patent Application 61/272,356, entitled "Image Processing and Tool Actuation for Medical Procedures" to Steinberg, filed Sep. 16, 2009; and (ii) is a continuation-in-part of U.S. patent application Ser. No. 12/075,244 to Tolkowsky (published as US 2008/0221442, now abandoned), filed Mar. 10, 2008, entitled "Imaging for use with moving organs," which claims the benefit of U.S. Provisional Patent Application Nos.:

60/906,091 filed on Mar. 8, 2007,
60/924,609 filed on May 22, 2007,
60/929,165 filed on Jun. 15, 2007,
60/935,914 filed on Sep. 6 2007, and
60/996,746 filed on Dec. 4, 2007,
all entitled "Apparatuses and methods for performing medical procedures on cyclically-moving body organs."

The present application is related to the following patent applications:

U.S. patent application Ser. No. 12/075,214 to Iddan (published as 2008/0221439, now abandoned), filed Mar. 10, 2008, entitled "Tools for use with moving organs."

U.S. patent application Ser. No. 12/075,252 to Iddan (published as US 2008/0221440), filed Mar. 10, 2008, entitled "Imaging and tools for use with moving organs."

U.S. patent application Ser. No. 12/781,260 to Blank (published as US 2010/0228076), filed May 17, 2010, entitled "Controlled actuation and deployment of a medical device."

U.S. patent application Ser. No. 12/487,315 to Iddan (issued as U.S. Pat. No. 8,700,130), filed Jun. 18, 2009, entitled "Stepwise advancement of a medical tool," which claims the benefit of U.S. Provisional Patent Application No. 61/129,331 to Iddan, filed on Jun. 19, 2008, entitled "Stepwise advancement of a medical tool."

FIELD OF EMBODIMENTS OF THE INVENTION

Some applications of the present invention generally relate to medical imaging. Specifically, some applications of the present invention relate to the co-use of endoluminal data and extraluminal imaging.

BACKGROUND

Vascular catheterizations, such as coronary catheterizations, are frequently-performed medical interventions. Such interventions are typically performed in order to diagnose the blood vessels for potential disease, and/or to treat diseased blood vessels. Typically, in order to facilitate diagnosis of blood vessels, the catheterization is performed under extraluminal imaging. For some procedures, an endoluminal data-acquisition device is used to perform endoluminal imaging and/or measurements. If appropriate based on the diagnosis, a treatment is applied to the blood vessel. For some procedures, treatment of the blood vessel includes the application of a treatment to the blood vessel by a therapeutic device that is placed endoluminally. For example, a therapeutic device (e.g., a balloon) is placed in the blood vessel temporarily and retrieved subsequent to the treatment having been applied. Alternatively, a therapeutic device (e.g., a stent) may remain implanted inside the blood vessel in order to treat the blood vessel.

SUMMARY OF EMBODIMENTS

Some applications of the present invention are applied to medical procedures performed, in whole or in part, on or within luminal structures. For some applications, apparatus and methods are provided for facilitating the co-use of extraluminal imaging and endoluminal data (i.e., data that are acquired using an endoluminal data-acquisition device), in performing medical procedures. Endoluminal data may include imaging data (e.g., imaging data acquired using an endoluminal imaging probe), data derived from measurements (e.g., measurements performed using an endoluminal sensor or measuring device), other data, and any combination thereof.

In accordance with some applications of the present invention, during insertion and deployment of an endoluminal device, e.g., an endoluminal therapeutic device, into a lumen, real-time extraluminal images of the device inside the lumen are displayed together with endoluminal data that were acquired previously and that correspond to the current location of the endoluminal therapeutic device. The cumulative effect of showing the extraluminal images and the endoluminal data is as if the endoluminal therapeutic tool is being inserted and deployed under both extraluminal imaging and endoluminal data acquisition. For some applications, the aforementioned techniques are applied since it is difficult or impossible to acquire the endoluminal data during insertion and deployment of the therapeutic device, because the lumen is too narrow to accommodate both the endoluminal therapeutic device and the endoluminal data-acquisition device. Alternatively, although it may be possible for the lumen to accommodate both the endoluminal therapeutic device and the endoluminal data-acquisition device, the aforementioned techniques may be used to prevent the endoluminal data-acquisition device from interfering with the endoluminal therapeutic device, during insertion and/or deployment of the therapeutic device.

There is therefore provided, in accordance with some applications of the present invention, apparatus for use with an endoluminal data-acquisition device that is configured to acquire a set of endoluminal data-points with respect to a lumen of a body of a subject at respective locations inside the lumen, a second endoluminal device, and a display configured to display images of the lumen, the apparatus including:
at least one processor, including:
location-association functionality configured to associate a given endoluminal data point acquired by the endoluminal data-acquisition device with a given location within the lumen;
location-determination functionality configured, in an extraluminal image of the second endoluminal device, to determine by means of image processing, a current location of at least a portion of the second endoluminal device inside the lumen;
display-driving functionality configured, in response to determining that the portion of the second endoluminal device is currently at the given location, to drive the display to display an indication of the endoluminal data point associated with the given location.

For some applications, the second endoluminal device includes a second endoluminal data-acquisition device configured to acquire a second set of endoluminal data-points with respect to the lumen at respective locations inside the lumen, and the display-driving functionality is configured, in response to determining that the portion of the second endoluminal data-acquisition device is currently at the given location, to drive the display to display:
an endoluminal image acquired by the first endoluminal data-acquisition device that corresponds to the given location, and
an endoluminal image acquired by the second endoluminal data-acquisition device that corresponds to the given location.

For some applications, the second endoluminal device includes a second endoluminal data-acquisition device configured to acquire a second set of endoluminal data-points with respect to the lumen at respective locations inside the lumen, and the display-driving functionality is configured, in response to determining that the portion of the second endoluminal data-acquisition device is currently at the given location, to drive the display to display:
an endoluminal image acquired by the second endoluminal data-acquisition device that corresponds to the given location, and
an indication of the given location with respect to an endoluminal image stack of the lumen generated using the endoluminal data points acquired by the first endoluminal data-acquisition device.

For some applications, the endoluminal data-acquisition device includes an endoluminal imaging probe configured to acquire endoluminal images of the lumen at respective locations inside the lumen, and the location-association functionality is configured to associate a given endoluminal image acquired by the endoluminal imaging probe with a given location within the lumen.

For some applications, the display-driving functionality is configured, in response to determining that the portion of the second endoluminal device is currently at the given location, to drive the display to display an endoluminal image that corresponds to the given location.

For some applications, the display-driving functionality is configured, in response to determining that the portion of the second endoluminal device is currently at the given location, to drive the display to display an indication of the given location with respect to an endoluminal image stack of the lumen.

For some applications, the display-driving functionality is configured, in response to determining that the portion of the second endoluminal device is currently at the given location, to drive the display to display an indication of the given location with respect to the extraluminal image of the lumen.

For some applications, the second endoluminal device includes a second endoluminal data-acquisition device configured to acquire a second set of endoluminal data-points with respect to the lumen at respective locations inside the lumen, and the display-driving functionality is further configured, in response to determining that the portion of the second endoluminal data-acquisition device is currently at the given location, to drive the display to display:
an endoluminal image acquired by the first endoluminal data-acquisition device that corresponds to the given location, and
an endoluminal image acquired by the second endoluminal data-acquisition device that corresponds to the given location.

For some applications, the second endoluminal device includes a second endoluminal data-acquisition device configured to acquire a second set of endoluminal data-points with respect to the lumen at respective locations inside the lumen, and the display-driving functionality is further configured, in response to determining that the portion of the second endoluminal data-acquisition device is currently at the given location, to drive the display to display:
an endoluminal image acquired by the second endoluminal data-acquisition device that corresponds to the given location, and
an indication of the given location with respect to an endoluminal image stack of the lumen generated using the endoluminal data points acquired by the first endoluminal data-acquisition device.

For some applications,
the endoluminal data-acquisition device includes a portion that is visible in extraluminal images of the data-acquisition device inside the lumen, and
the location-association functionality is configured to associate the endoluminal data point with the given location inside the lumen by determining, by means of image-processing, in an extraluminal image of the data-acquisition device inside the lumen, a location of at least the visible portion of the data-acquisition device inside the lumen, at the acquisition of the endoluminal data point.

For some applications,
the endoluminal data-acquisition device includes an image-acquiring portion, and
the location-association functionality is configured to associate the endoluminal data point with the given location inside the lumen by accounting for an offset between the portion of the endoluminal data-acquisition device that is visible in the extraluminal image, and the image-acquiring portion of the endoluminal data-acquisition device.

For some applications, the second endoluminal device includes an endoluminal therapeutic device configured to apply a therapy to the lumen, and the location-determination functionality is configured, in an extraluminal image of the endoluminal therapeutic device, to determine by means of image processing, a current location of at least a portion of the endoluminal therapeutic device inside the lumen.

For some applications, the endoluminal therapeutic device includes a guidewire configured to penetrate an occlusion of the lumen and the endoluminal data-acquisition device includes a forward-looking endoluminal imaging probe, and the location-association functionality configured to associate the given endoluminal data point with the given location by associating an endoluminal image of a portion of the lumen that is distal to the given location with the given location.

There is further provided, in accordance with some applications of the present invention, a method, including:
acquiring a set of endoluminal data point of a lumen of a subject's body;
determining that one of the endoluminal data points of the set corresponds to a given location inside the lumen; and subsequently,
while a second endoluminal device is inside the lumen:
acquiring an extraluminal image of the second endoluminal device inside the lumen;
by means of image processing, determining, based upon the extraluminal image, a current location of at least a portion of the second endoluminal device inside the lumen; and
in response to determining that the portion of the second endoluminal device is currently at the given location, displaying an indication of the endoluminal data point that corresponds to the given location.

For some applications, the second endoluminal device includes an endoluminal therapeutic device configured to apply a therapy to the lumen, and acquiring the extraluminal image of the second endoluminal device inside the lumen includes acquiring an extraluminal image of the endoluminal therapeutic device inside the lumen.

For some applications, the endoluminal therapeutic device includes a guidewire, and the method further includes penetrating an occlusion of the lumen with the guidewire.

For some applications, acquiring the at least one endoluminal data point includes, while a forward-looking endoluminal imaging probe is at the given location, acquiring an endoluminal image of a portion of the lumen that is distal to the given location.

There is additionally provided, in accordance with some applications of the present invention, a method for use with an endoluminal data-acquisition device configured to be moved through a lumen of a subject's body, the endoluminal data-acquisition device having a radiopaque marker coupled thereto, including:
while the endoluminal data-acquisition device is being moved through the lumen, acquiring a plurality of endoluminal data points of the lumen using the endoluminal data-acquisition device;
determining that a first endoluminal data point corresponds to a first location within the lumen, by:
acquiring a first angiographic image of the lumen, at a time associated with an acquisition of the first endoluminal data point by the endoluminal data-acquisition device, and
determining a location of the radiopaque marker within the first angiographic image of the lumen, by performing image processing on the first angiographic image, the location of the radiopaque marker within the first angiographic image of the lumen corresponding to the first endoluminal data point;
determining that a second endoluminal data point corresponds to a second given location within the lumen, by:
acquiring a second angiographic image of the lumen, at a time associated with an acquisition of the second endoluminal data point by the endoluminal data-acquisition device, and
determining a location of the radiopaque marker within the second angiographic image of the lumen by performing image processing on the second angiographic image, the location of the radiopaque marker within the second angiographic image of the lumen corresponding to the second endoluminal data point;
generating a combined angiographic image of the lumen that includes representations of the first and second marker locations thereon, by co-registering the first and second angiographic images; and
determining that at least one location on the combined angiographic image that is intermediate to the first and second locations of the radiopaque marker corresponds to an endoluminal data point acquired between the acquisitions of the first and second data points, by interpolating between the first and second locations of the radiopaque marker on the combined angiographic image; and
generating an output in response thereto.

For some applications, acquiring the plurality of endoluminal data points of the lumen using the endoluminal data-acquisition device while the endoluminal data-acquisition device is being moved through the lumen includes acquiring the plurality of endoluminal data points of the lumen using the endoluminal data-acquisition device while the endoluminal data-acquisition device is being pulled-back through the lumen.

There is further provided, in accordance with some applications of the present invention, apparatus for use with:
an endoluminal data-acquisition device configured to acquire a plurality of endoluminal data points of a lumen of a body of a subject at respective locations inside the lumen, while the endoluminal data-acquisition device is moved through the lumen, the endoluminal data-acquisition device having a radiopaque marker coupled thereto,
an angiographic imaging device configured to (a) acquire a first angiographic image of the lumen, at a time associated with an acquisition of a first endoluminal data point by the endoluminal data-acquisition device, and (b) acquire a second angiographic image of the lumen, at a time associated with an acquisition of a second endoluminal data point by the endoluminal data-acquisition device, and
a display,
the apparatus including:
at least one processor, including:
location-determination functionality configured to:
determine that the first endoluminal data point corresponds to a first location within the lumen, by determining a location of the radiopaque marker within the first angiographic image of the lumen, by performing image processing on the first angiographic image, the location of the radiopaque marker within the first angiographic image of the lumen corresponding to the first endoluminal data point, and
determine that a second endoluminal data point corresponds to a second given location within the lumen by determining a location of the radiopaque marker within the second angiographic image of the lumen by performing image processing on the second angiographic image, the location of the radiopaque marker within the second angiographic image of the lumen corresponding to the second endoluminal data point;
image-co-registration functionality configured to generate a combined angiographic image of the lumen that includes representations of the first and second marker locations thereon, by co-registering the first and second angiographic images;
location-association functionality configured to determine that at least one location on the combined angiographic image that is intermediate to the first and second locations of the radiopaque marker corresponds to an endoluminal data point acquired between the acquisitions of the first and second data points, by interpolating between the first and second locations of the radiopaque marker on the combined angiographic image;
display-driving functionality configured to drive the display to display an output, in response to determining that the intermediate location corresponds to the endoluminal data point acquired between the acquisitions of the first and second data points.

For some applications, the location-determination functionality is configured to:
determine that the first endoluminal data point corresponds to the first location within the lumen by determining that the first endoluminal data point corresponds to a location in a vicinity of a first end of a luminal segment of interest, and
determine that the second endoluminal data point corresponds to the second location within the lumen by determining that the second endoluminal data point corresponds to a location in a vicinity of a second end of the luminal segment of interest.

For some applications,
the location-determination functionality is configured to:
determine that the first endoluminal data point corresponds to the first location within the lumen by determining that the first endoluminal data point corresponds to a location in a vicinity of a first end of a luminal segment of interest, and
determine that the second endoluminal data point corresponds to the second location within the lumen by determining that the second endoluminal data point corresponds to a location between the first end and a second end of the luminal segment of interest, and
the angiographic imaging device includes an angiographic imaging device that is further configured to acquire a third angiographic image of the lumen, at a time associated with an acquisition of a third endoluminal data point by the endoluminal data-acquisition device,
the location-determination functionality is further configured to determine that third endoluminal data point corresponds to a location in a vicinity of the second end of the luminal segment of interest, by determining a location of the radiopaque marker within the third angiographic image of the lumen by performing image processing on the third angiographic image, the location of the radiopaque marker within the third angiographic image of the lumen corresponding to the third endoluminal data point;
the image-co-registration functionality is further configured to generate a representation of the third marker location on the combined angiographic image, by co-registering the first, second, and third angiographic images; and
the location-association functionality is further configured to determine that at least one location on the combined angiographic image that is intermediate to the second and third locations of the radiopaque marker corresponds to an endoluminal data point acquired between the acquisitions of the second and third data points, by interpolating between the second and third locations of the radiopaque marker on the combined angiographic image; and
the display-driving functionality is further configured to drive the display to display an output, in response to determining that the intermediate location corresponds to the endoluminal data point acquired between the acquisitions of the second and third data points.

For some applications, the location-association functionality is configured to interpolate between the first and second locations of the radiopaque marker on the combined angiographic image by assuming that, between acquiring respective successive pairs of endoluminal data points between the acquisitions of the first and second data points, the endoluminal data acquisition device travelled equal distances.

For some applications, the location-association functionality is configured to interpolate between the first and second locations of the radiopaque marker on the combined angiographic image by assuming that a rate of the movement of the endoluminal data acquisition device was linear between the acquisitions of the first and second data points.

There is additionally provided, in accordance with some applications of the present invention, a method for use with an endoluminal data-acquisition device configured to be moved through a lumen of a subject's body, the endoluminal data-acquisition device having a radiopaque marker coupled thereto, including:
while the endoluminal data-acquisition device is being moved through the lumen:
acquiring a plurality of endoluminal data points of the lumen using the endoluminal data-acquisition device;
continuously injecting contrast agent into the lumen; and
acquiring a plurality of angiographic images of the data-acquisition device;
determining that endoluminal data points correspond to respective locations within the lumen, by determining locations of the radiopaque marker within the angiographic images of the lumen, by performing image processing on the angiographic images, the locations of the radiopaque marker within the angiographic images of the lumen corresponding to respective endoluminal data points; and
generating an output in response thereto.

For some applications, continuously injecting the contrast agent into the lumen includes continuously injecting the contrast agent into the lumen for a period of at least two seconds.

For some applications, acquiring the plurality of endoluminal data points of the lumen using the endoluminal data-acquisition device includes acquiring the plurality of endoluminal data points of the lumen using the endoluminal data-acquisition device while the data-acquisition device is being pulled back through the lumen.

For some applications, continuously injecting the contrast agent into the lumen includes continuously injecting the contrast agent over at least 50% of a duration of a period over which the endoluminal data-acquisition device acquires the endoluminal data points.

For some applications, continuously injecting the contrast agent into the lumen includes continuously injecting the contrast agent over at least 80% of a duration of a period over which the endoluminal data-acquisition device acquires the endoluminal data points.

There is further provided, in accordance with some applications of the present invention, apparatus for use with:

an endoluminal data-acquisition device configured to acquire a plurality of endoluminal data points of a lumen of a body of a subject at respective locations inside the lumen, while the endoluminal data-acquisition device is being moved through the lumen, the endoluminal data-acquisition device having a radiopaque marker coupled thereto, contrast agent configured to be continuously injected into the lumen, during the movement of the endoluminal data-acquisition device, an angiographic imaging device configured to acquire a plurality of angiographic images of the endoluminal data-acquisition device inside the lumen, during the movement of the endoluminal data-acquisition device, and a display configured to display images of the lumen,
the apparatus including:
at least one processor, including:
location-association functionality configured to determine that endoluminal data points correspond to respective locations within the lumen, by determining locations of the radiopaque marker within the angiographic images of the lumen, by performing image processing on the angiographic images, the locations of the radiopaque marker within the angiographic images of the lumen corresponding to respective endoluminal data points;
display-driving functionality configured to drive the display to display an output, in response to determining that the endoluminal data points correspond to respective locations within the lumen.

For some applications, the endoluminal data-acquisition device includes an endoluminal imaging probe configured to acquire a plurality of endoluminal images at a first frame rate, the angiographic imaging device includes an angiographic imaging device that is configured to acquire the plurality of angiographic images at a second frame rate that is different from the first frame rate, and the location-association functionality is configured to determine that endoluminal data points correspond to respective locations within the lumen by indexing the endoluminal images with respect to the angiographic images.

There is additionally provided, in accordance with some applications of the present invention, a method for use with an endoluminal data-acquisition device configured to be moved through a lumen of a subject's body, the endoluminal data-acquisition device having a radiopaque marker coupled thereto, including:

while the endoluminal data-acquisition device is being moved through the lumen, acquiring a plurality of endoluminal data points of the lumen using the endoluminal data-acquisition device;

determining that respective endoluminal data points correspond to respective locations within the lumen, by acquiring at least first and second angiographic images of the lumen, and determining first and second locations of the marker respectively within the first and second angiographic images;

generating a combined angiographic image of the lumen that includes representations thereon of the first and second marker locations within the lumen, by co-registering the first and second angiographic images to one another, by:
designating one of the angiographic images as a baseline image, a shape of the lumen in the baseline image being designated as a baseline shape of the lumen;
determining whether a shape of the lumen in the angiographic image that is not the baseline image is the same as the baseline shape of the lumen; and
in response to determining that the shape of the lumen in the angiographic image that is not the baseline image is not the same as the baseline shape of the lumen:
designating the image that is not the baseline image as a non-baseline image, and
deforming the shape of the lumen in the non-baseline image, such that the shape of the lumen becomes more similar to the baseline shape of the portion than when the lumen in the non-baseline image is not deformed;
based upon the deformation of the non-baseline image, determining a location upon the baseline image at which the marker from within the non-baseline image should be located; and
generating an indication of the marker from within the non-baseline image at the determined location on the baseline image.

For some applications, acquiring the plurality of endoluminal data points of the lumen using the endoluminal data-acquisition device while the endoluminal data-acquisition device is being moved through the lumen includes acquiring the plurality of endoluminal data points of the lumen using the endoluminal data-acquisition device while the endoluminal data-acquisition device is being pulled-back through the lumen.

There is additionally provided, in accordance with some applications of the present invention, apparatus for use with:

an endoluminal data-acquisition device configured to acquire a plurality of endoluminal data points of a lumen of a body of a subject at respective locations inside the lumen, while the endoluminal data-acquisition device is moved through the lumen, the endoluminal data-acquisition device having a radiopaque marker coupled thereto, an angiographic imaging device configured to acquire respective angiographic image of the lumen, at times associated with acquisitions of respective endoluminal data point by the endoluminal data-acquisition device, and a display,
the apparatus including:
at least one processor, including:
location-determination functionality configured to determine first and second locations of the radiopaque marker respectively within first and second angiographic images of the lumen;
image-co-registration functionality configured to generate a combined angiographic image of the lumen that includes representations of the first and second marker locations thereon, by co-registering the first and second angiographic images to one another, by:
designating one of the angiographic images as a baseline image, a shape of the lumen in the baseline image being designated as a baseline shape of the lumen;
determining whether a shape of the lumen in the angiographic image that is not the baseline image is the same as the baseline shape of the lumen; and in response to determining that the shape of the lumen in the angiographic image that is not the baseline image is not the same as the baseline shape of the lumen:

designating the image that is not the baseline image as a non-baseline image, and deforming the shape of the lumen in the non-baseline image, such that the shape of the lumen becomes more similar to the baseline shape of the portion than when the lumen in the non-baseline image is not deformed;

based upon the deformation of the non-baseline image, determining a location upon the baseline image at which the marker from within the non-baseline image should be located; and generating an indication of the marker from within the non-baseline image at the determined location on the baseline image; and display-driving functionality configured to drive the display to display an output, in response to generating the combined angiographic image of the lumen.

For some applications, the location-determination functionality is configured to:

determine that a first endoluminal data point corresponds to a first location within the lumen, by determining a location of the radiopaque marker within the first angiographic image of the lumen, by performing image processing on the angiographic image, the location of the first radiopaque marker within the first angiographic image of the lumen corresponding to the first endoluminal data point, and determine that a second endoluminal data point corresponds to a second given location within the lumen by determining a location of the radiopaque marker within the second angiographic image of the lumen by performing image processing on the second angiographic image, the location of the radiopaque marker within the second angiographic image of the lumen corresponding to the second endoluminal data point.

For some applications, the location-determination functionality is configured to:

determine that the first endoluminal data point corresponds to the first location within the lumen by determining that the first endoluminal data point corresponds to a location in a vicinity of a first end of a luminal segment of interest, and determine that the second endoluminal data point corresponds to the second location within the lumen by determining that the second endoluminal data point corresponds to a location in a vicinity of a second end of the luminal segment of interest.

For some applications, the at least one processor further includes location-association functionality configured to determine that at least one location on the combined angiographic image that is intermediate to the first and second locations of the radiopaque marker corresponds to an endoluminal data point acquired between the acquisitions of the first and second data points, by interpolating between the first and second locations of the radiopaque marker on the combined angiographic image.

There is further provided, in accordance with some applications of the present invention, a method for imaging a tool inside a portion of a body of a subject that undergoes motion, the tool having contours, the method including:

acquiring a plurality of image frames of the portion of the subject's body; and generating at least one image frame in which the tool is enhanced, by:

identifying radiopaque markers in the image frames;

identifying edge lines in a vicinity of the markers within the image frames, the edge lines corresponding to contours of the tool;

in response to the identifying of the edge lines, selecting a subset of the image frames that are based upon the acquired image frames, based upon a level of similarity between the edge lines in the selected image frames to one another;

aligning the contours in a plurality of the selected image frames, and averaging the plurality of aligned frames to generate an averaged image frame; and displaying the averaged image frame.

There is further provided, in accordance with some applications of the present invention, apparatus for use with a tool configured to be placed inside a portion of a body of a subject that undergoes motion, the tool having contours, an image-acquisition device configured to acquire a plurality of image frames of the portion of the subject's body, and a display, the apparatus including:

at least one processor configured to generate at least one image frame in which the tool is enhanced, the processor including:

image-receiving functionality configured to receive the plurality of image frames into the processor, marker-identifying functionality configured to automatically identify radiopaque markers in the image frames, edge-line-identifying functionality configured to automatically identify edge lines in a vicinity of the radiopaque markers in the image frames, image-selection functionality configured, in response to the identifying of the edge lines, to select a subset of the image frames that are based upon the acquired image frames, based upon a level of similarity between the edge lines in the selected image frames to one another, image-alignment functionality configured to align the edge lines in a plurality of the selected image frames, and image-averaging functionality configured to generate an averaged image frame by averaging the plurality of aligned image frames; and display-driving functionality configured to drive the display to display the averaged image frame.

For some applications, the image-selection functionality is configured to select the subset of image frames based upon a level of similarity between shapes of the edge lines in the image frames.

For some applications, the image-selection functionality is configured to select the subset of image frames based upon a level of alignment between the edge lines and the radiopaque markers in the image frames.

For some applications, the image-selection functionality is configured to select the subset of image frames by rejecting from being included in the subset, at least one image frame in which edge lines corresponding to the contours of the tool appear.

For some applications, the image-alignment functionality is configured to align the edge lines in the selected image frames by translating at least one image frame with respect to at least one other image frame of the selected image frames.

For some applications, the processor is configured to generate a plurality of image frames in which the tool is enhanced, and the display-driving functionality is configured to drive the display to display, as an image stream, the plurality of image frames in which the tool is enhanced.

For some applications, the tool includes a stent that is inserted into the lumen while disposed on a device, and the marker-identifying functionality is configured to identify the radiopaque markers by identifying radiopaque markers that are coupled to the device, and the edge-line-identifying functionality is configured to identify the edge lines by identifying curved edge lines, corresponding to contours of the stent.

For some applications, the image-selection functionality is configured to select the subset of image frames based upon a level of similarity between shapes of the curved edge lines in the image frames.

For some applications, the marker-identifying functionality is configured to identify first and second radiopaque markers that are coupled to the device, and the image-selection functionality is configured to select the subset of image frames based upon a level of alignment between the edge lines and an imaginary line running from the first marker to the second marker in the image frames.

There is further provided, in accordance with some applications of the present invention, a method for use with an endoluminal data-acquisition device configured to acquire endoluminal data points while moving through a lumen of a subject's body generally in a first direction with respect to the lumen, including:

while the endoluminal data-acquisition device is being moved through the lumen, acquiring a plurality of endoluminal data points of the lumen using the endoluminal data-acquisition device;

determining that, at at least one location, two or more endoluminal data points were acquired;

generating an output using a portion of the plurality of endoluminal data points of the lumen acquired using the endoluminal data-acquisition device, by using only a single endoluminal data point corresponding to the location.

There is further provided, in accordance with some applications of the present invention, apparatus for use with an endoluminal data-acquisition device that acquires a plurality of endoluminal data points of a lumen of a body of a subject while being moved through the lumen generally in a first direction with respect to the lumen, and a display, the apparatus including:

at least one processor including:
 duplicate-data-point-identification functionality configured to determine that, at at least one location, two or more endoluminal data points were acquired by the endoluminal data-acquisition device;
 data-point-selection functionality configured to generate an output using a portion of the plurality of endoluminal data points of the lumen acquired using the endoluminal data-acquisition device, by using only a single data point corresponding to the location; and
 display-driving functionality configured to drive the display to display the output.

For some applications, the data-point-selection functionality is configured to use only the single data point corresponding to the location by using a single one of the two or more endoluminal data points that were acquired at the at least one location, and rejecting another one of the two or more endoluminal data points from being used in the output For some applications, the data-point-selection functionality is configured to generate the output selecting for use as the single data point a data point that was acquired at the given location at an earliest time with respect to the data points that were acquired at the given location.

For some applications, the data-point-selection functionality is configured to generate the output by rejecting from being used in the output an endoluminal data point that was acquired while the device was moving in a second direction with respect to the lumen that is opposite to the first direction.

For some applications, the data-point-selection functionality is configured:
 to generate the output by generating an indication that one of the two or more endoluminal data points is associated with the location by co-registering the portion of the plurality of endoluminal data points of the lumen with the extraluminal image, and
 to reject the other one of the two or more endoluminal data points from being used in the output by rejecting one of the two or more endoluminal images from being indicated to be associated with the location.

For some applications,
 the endoluminal data-acquisition device includes an endoluminal imaging probe configured to acquire a plurality of endoluminal image frames of the lumen, and
 the data-point-selection functionality is configured:
  to generate the output by generating an endoluminal image stack using some of the plurality of endoluminal image frames of the lumen, and
  to reject the other one of the two or more endoluminal data points from being used in the output by rejecting the other one of the two or more endoluminal image frames from being displayed in the image stack.

For some applications, the duplicate-data-point-identification functionality is configured to determine that, at at least one location, two or more endoluminal data points were acquired by determining that the endoluminal data-acquisition device moved past the location in a second direction with respect to the lumen that is opposite to the first direction, and the data-point-selection functionality is configured to generate the output by placing image frames in order within the image stack based on determining that the endoluminal data-acquisition device moved past the location, in the second direction with respect to the lumen.

For some applications, the duplicate-data-point-identification functionality is configured to determine that, at at least one location, two or more endoluminal data points were acquired by:
 sensing a signal that is indicative of the subject's cardiac cycle, while the endoluminal data-acquisition device acquires the plurality of data points,
 determining that a given data point was acquired at a given phase of the subject's cardiac cycle, and
 in response thereto, identifying the given data point as having been acquired at a location at which another data point was acquired.

For some applications, the duplicate-data-point-identification functionality configured to determine that the given data point was acquired at the given phase of the subject's cardiac cycle by determining that the given data point was acquired during at least a portion of systole.

For some applications, the duplicate-data-point-identification functionality is configured to determine that, at at least one location, two or more endoluminal data points were acquired by determining that the endoluminal data-acquisition device moved past the location in a second direction with respect to the lumen that is opposite to the first direction.

For some applications, the duplicate-data-point-identification functionality configured to determine that the endoluminal data-acquisition device moved past the location in the second direction with respect to the lumen by performing image processing on extraluminal images of the device moving through the lumen generally in the first direction.

For some applications, the apparatus further includes a sensor configured to detect movement of a portion of the endoluminal data-acquisition device, and the duplicate-data-point-identification functionality is configured to determine that the endoluminal data-acquisition device moved past the location in the second direction with respect to the lumen, in response to a signal from the sensor.

There is further provided, in accordance with some applications of the present invention, a method for use with an endoluminal data-acquisition device configured to acquire endoluminal data points while moving through a lumen of a subject's body generally in a first direction with respect to the lumen, including:

while the endoluminal data-acquisition device is being moved through the lumen, acquiring a plurality of endoluminal data points of the lumen using the endoluminal data-acquisition device;

determining that, while acquiring at least one of the endoluminal data points, the endoluminal data-acquisition device was moving in a second direction that is opposite to the first direction; and in response to the determining, generating an output using at least some of the plurality of endoluminal data points of the lumen acquired using the endoluminal data-acquisition device.

There is additionally provided, in accordance with some applications of the present invention, apparatus for use with an endoluminal data-acquisition device that acquires a plurality of endoluminal data points of a lumen of a body of a subject while being moved through the lumen generally in a first direction with respect to the lumen and a display, the apparatus including:

at least one processor including:
  direction-determination functionality configured to determine that, while acquiring at least one of the endoluminal data points, the endoluminal data-acquisition device was moving in a second direction that is opposite to the first direction;
  output-generation functionality configured, in response to the determining, to generate an output using at least some of the plurality of endoluminal data points of the lumen acquired using the endoluminal data-acquisition device; and
  display-driving functionality configured to drive the display to display the output.

For some applications, the direction-determination functionality is configured to determine that, while acquiring at least one of the endoluminal data points, the endoluminal data-acquisition device was moving in a second direction that is opposite to the first direction by performing image processing on extraluminal images of the device moving through the lumen generally in the first direction.

For some applications, the apparatus further includes a sensor configured to detect movement of a portion of the endoluminal data-acquisition device, and the direction-determination functionality configured to determine that, while acquiring at least one of the endoluminal data points, the endoluminal data-acquisition device was moving in a second direction that is opposite to the first direction, in response to a signal from the sensor.

For some applications,
the endoluminal data-acquisition device includes an endoluminal imaging probe configured to acquire a plurality of endoluminal image frames of the lumen, and
the output-generation functionality is configured to generate the output by generating an endoluminal image stack using at least some of the plurality of endoluminal image frames of the lumen.

For some applications, the output-generation functionality is configured to generate the output by placing image frames in order within the image stack based on determining that, while acquiring at least one of the endoluminal data points, the endoluminal data-acquisition device was moving in the second direction.

For some applications, the output-generation functionality is configured to generate the output by generating an indication on the endoluminal image stack of at least a portion of the endoluminal image stack that was acquired by the data-acquisition device while the data-acquisition device was moving in the second direction.

For some applications, the direction-determination functionality is configured to determine that, while acquiring at least one of the endoluminal data points, the endoluminal data-acquisition device was moving in a second direction that is opposite to the first direction by:

sensing a signal that is indicative of the subject's cardiac cycle, while the endoluminal data-acquisition device acquires the plurality of data points,
determining that a given data point was acquired at a given phase of the subject's cardiac cycle, and
in response thereto, identifying the given data point as having been acquired while the endoluminal data-acquisition device was moving in the second direction.

For some applications, the direction-determination functionality is configured to determine that the given data point was acquired at the given phase of the subject's cardiac cycle by determining that the given data point was acquired during at least a portion of systole.

The present invention will be more fully understood from the following detailed description of embodiments thereof, taken together with the drawings, in which:

BRIEF DESCRIPTION OF THE DRAWINGS

FIG. 3 is a flow chart, at least some of the steps of which are used in procedures that utilize co-use of endoluminal data and extraluminal imaging, in accordance with some applications of the present invention;

DETAILED DESCRIPTION OF EMBODIMENTS

Figure 1:
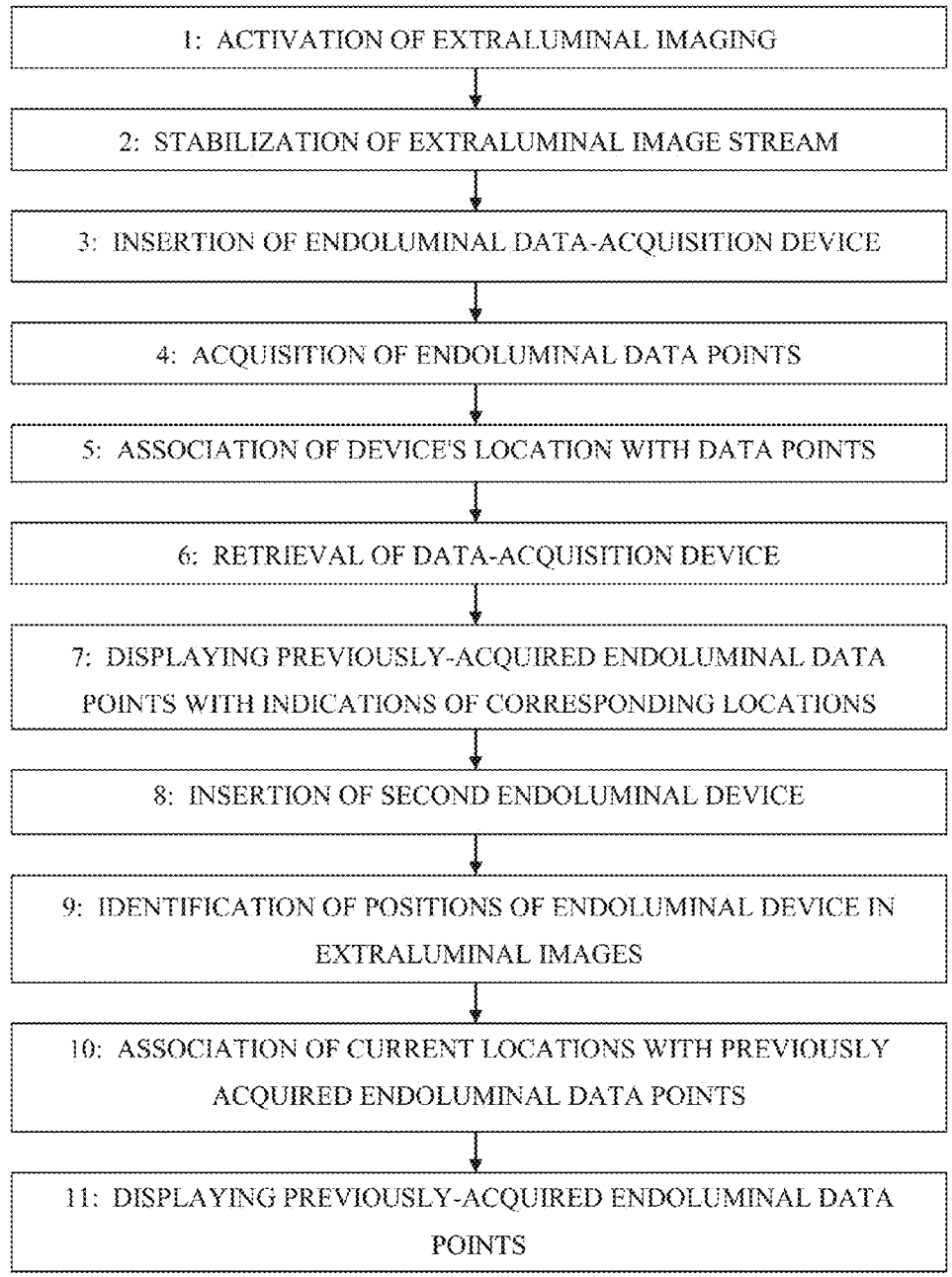
FIG. 1 is a flow chart, at least some of the steps of which are used in procedures that utilize co-use of endoluminal data and extraluminal imaging, in accordance with some applications of the present invention.

The terms "medical tool," "tool", "device," and "probe" refer to any type of a diagnostic or therapeutic or other functional tool including, but not limited to, a cardiovascular catheter, a stent delivery and/or placement and/or retrieval tool, a balloon delivery and/or placement and/or retrieval tool, a valve delivery and/or repair and/or placement and/or retrieval tool, a graft delivery and/or placement and/or retrieval tool, a tool for the delivery and/or placement and/or retrieval of an implantable device or of parts of such device, an implantable device or parts thereof, a tool for closing a gap, a tool for closing a septal defect, a guide wire, a marker wire, a suturing tool, a clipping tool (such as a valve-leaflet-clipping tool), a biopsy tool, an aspiration tool, a navigational tool, a localization tool, a probe comprising one or more location sensors, a tissue characterization probe, a probe for the analysis of fluid, a measurement probe, an electrophysiological probe, a stimulation probe, an ablation tool, a tool for penetrating or opening partial or total occlusions in blood vessels, a drug or substance delivery tool, a chemotherapy tool, a photodynamic therapy tool, a brachytherapy tool, a local irradiation tool, a laser device, a tool for delivering energy, a tool for delivering markers or biomarkers, a tool for delivering biological glue, an irrigation device, a suction device, a ventilation device, a device for delivering and/or placing and/or retrieving a lead of an electrophysiological device, a lead of an electrophysiological device, a pacing device, a coronary sinus device, an imaging device, a sensing probe, a probe comprising an optical fiber, a robotic tool, a tool that is controlled remotely, an excision tool, a plaque excision tool (such as a plaque excision catheter) or any combination thereof.

The terms "image" and "imaging" refer to any type of medical imaging, typically presented as a sequence of images and including, but not limited to, imaging using ionizing radiation, imaging using non-ionizing radiation, video, fluoroscopy, angiography, ultrasound, CT, MR, PET, PET-CT, CT angiography, SPECT, Gamma camera imaging, Optical Coherence Tomography (OCT), Near-Infra-Red Spectroscopy (NIRS), Vibration Response Imaging (VRI), Optical Imaging, infrared imaging, electrical mapping imaging, other forms of Functional Imaging, or any combination or fusion thereof. Examples of ultrasound imaging include Endo-Bronchial Ultrasound (EBUS), Trans-Thoracic Echo (TTE), Trans-Esophageal Echo (TEE), Intra-Vascular Ultrasound (IVUS), Intra-Cardiac Ultrasound (ICE), or any combination thereof.

The term "contrast agent," when used in reference to its application in conjunction with imaging, refers to any substance that is used to highlight, and/or enhance in another manner, the anatomical structure, functioning, and/or composition of a bodily organ while the organ is being imaged.

The term "stabilized," when used in the context of displayed images, means a display of a series of images in a manner such that periodic, cyclical, and/or other motion of the body organ(s) being imaged, and/or of a medical tool being observed, is partially or fully reduced, with respect to the entire image frame, or at least a portion thereof.

The term "automatic," when used for describing the generation and utilization of the road map, means "without necessitating user intervention or interaction." (Such interaction or intervention may still however be optional in some cases.)

The term "real time" means without a noticeable delay.

The term "near real time" means with a short noticeable delay (such as approximately one or two motion cycles of the applicable organ, and, in the case of procedures relating to organs or vessels the motion of which are primarily as a result of the cardiac cycle, less than two seconds).

The term "on-line," when used in reference to image processing, or to measurements being made on images, means that the image processing is performed, and/or the measurements are made, intra-procedurally, in real time or near real time.

Applications of the present invention are typically used during medical procedures that are performed, in whole or in part, on or within luminal structures. For some applications, apparatus and methods provided herein facilitate the co-use of extraluminal imaging and endoluminal data in performing such medical procedures. Endoluminal data may include imaging data, data derived from measurements, other data, or any combination thereof.

For some applications, the co-use of the endoluminal data and the extraluminal images is performed in the following manner. Endoluminal data are acquired by positioning an endoluminal data-acquisition device along a luminal segment of interest that includes a designated luminal site. Subsequently, while observing extraluminal images of the luminal segment, one or more locations along that segment are indicated by a user input device. In response to the indication of the one or more locations by the user input device, the corresponding, previously-acquired endoluminal images are displayed.

Typically, the designated luminal site includes a site being diagnosed, and at which, subject to the outcome of the diagnosis, a therapeutic device will be positioned and deployed, e.g., the site of an anatomical feature, the implantation site of a previously-implanted device, and/or a site at a defined location with respect to the implantation site. For example, the designated luminal site may include a portion of the lumen that is narrow with respect to surrounding portions of the lumen, and/or the site of a lesion.

For some applications, the co-use of the endoluminal data and the extraluminal images is performed in the following manner. Endoluminal data are acquired by positioning an endoluminal data-acquisition device at a designated luminal site. Subsequently, an endoluminal therapeutic device is positioned and deployed at the designated luminal site under extraluminal imaging, while concurrently viewing on-line the endoluminal data that were previously acquired by the endoluminal data-acquisition device at the current location of the therapeutic device. Typically, endoluminal data are acquired at respective endoluminal sites in the vicinity of the designated endoluminal site. Subsequently, when the endoluminal therapeutic device is placed inside the lumen, previously-acquired endoluminal data are displayed and updated, typically automatically and typically on-line, to correspond to the current location of the therapeutic device (or of a portion thereof), the location of the therapeutic device typically changing during the positioning of the therapeutic device.

For some applications, extraluminal imaging and the previously-acquired endoluminal data are co-used such that it is as if the therapeutic device is being positioned and deployed under both real-time extraluminal imaging and real-time endoluminal data acquisition. This is because (a) the extraluminal imaging is performed in real-time, and (b), although the endoluminal data are not acquired in real-time, endoluminal data are displayed that correspond to the current location of the therapeutic device.

In accordance with some applications of the present invention, when the therapeutic device is disposed inside the lumen, the location of the device within the lumen is determined by performing image processing on the extraluminal image of the device inside the lumen.

For some applications, the image processing includes tracking of one or more visible portions of a moving therapy-applying portion of the device in the extraluminal images. Typically, the tracking is performed in real time, and, typically, in accordance with techniques described in US 2010/0228076 to Blank, which is incorporated herein by reference.

For some applications, the image processing includes stabilization of an image stream produced by the extraluminal imaging. Typically, the stabilization is performed in real time, and typically in accordance with techniques described in US 2008/0221442 to Tolkowsky, or US 2010/0228076 to Blank, both of which applications are incorporated herein by reference. Typically, the stabilization facilitates the co-use of the endoluminal data with the extraluminal images (particularly in cases of intense organ motion). This is because it is typically easier to determine the luminal location of the therapeutic device based upon a stabilized image stream than to determine the luminal location of the therapeutic device on a native, non-stabilized image stream.

For some applications, the stabilized image stream is also enhanced, typically in real time, typically in accordance with techniques described in US 2010/0228076 to Blank.

For some applications, during the acquisition of the endoluminal data by the endoluminal data-acquisition device, the location of the endoluminal data-acquisition device is determined by advancing the endoluminal data-acquisition device under extraluminal imaging and image processing the extraluminal images to determine the location of a moving data-acquiring portion of the endoluminal data-acquisition device. For some applications, during this stage, the extraluminal image stream is stabilized and/or enhanced, as described hereinabove, to facilitate the determination of the location of the endoluminal data-acquisition device, based upon the extraluminal images. Alternatively, other techniques are used for determining the location of the endoluminal data-acquisition device, as described hereinbelow.

For some applications, the luminal structure to which the apparatus and methods described herein are applied includes a lumen in the vascular system, the respiratory tract, the digestive tract, the urinary tract, or any other luminal structure within a patient's body.

For some applications, the endoluminal data-acquisition device is an imaging probe. For some applications, the imaging probe is an IVUS probe, an EBUS probe, another ultrasound probe, an OCT probe, an NIRS probe, an MR probe, or any combination thereof.

For some applications, the endoluminal data-acquisition device performs additional functions. For example, the endoluminal data-acquisition device may comprise a probe, such as the VIBE™ RX Vascular Imaging Balloon Catheter, marketed by Volcano Corporation (San Diego, USA), that includes both IVUS and coronary balloon functionalities.

For some applications, the endoluminal data-acquisition device acquires data in a form other than images. For example, the data may include data related to pressure, flow, temperature, electrical activity, or any combination thereof. For some applications, and typically when data are acquired with respect to a coronary vessel, the endoluminal data-acquisition device is a Fractional Flow Reserve (FFR) probe.

For some applications, the extraluminal imaging is fluoroscopy, CT, MR, PET, SPECT, ultrasound, or any combination thereof.

For some applications, the apparatus and methods described herein are used with a therapeutic device that is positioned and/or deployed at an anatomical feature that requires or potentially requires treatment, such as a partial or total occlusion, a native valve, an aneurism, a dissection, a malformation, a septal defect, a mass suspected of being malignant, a mass suspected of being inflammatory, etc. The endoluminal data are typically determined at, and/or in the vicinity of, the anatomical feature.

For some applications, apparatus and methods described herein are used with a therapeutic device that is positioned and/or deployed at an implantation site of a previously-implanted device such as a stent, a graft or a replacement valve. The endoluminal data are determined at, and/or in the vicinity of, the implantation site. For example, the techniques described herein may be used during the placement of a new prosthetic aortic valve at the site of (e.g., inside) a previously implanted prosthetic aortic valve that is no longer functioning.

For some applications, apparatus and methods described herein are used with a therapeutic device that is positioned and/or deployed at a defined location relative to a previously-implanted device such as a stent, a graft or a replacement valve. The endoluminal data are determined at and in the vicinity of the defined location. For example, the techniques described herein may be used during the placement of a coronary stent such that the new stent overlaps with or is adjacent to a previously-implanted stent, in order to treat a long lesion and/or a lesion that has diffused along a coronary artery.

Reference is now made to FIG. 1, which is a flow chart, at least some of the steps of which are used in the course of co-use of endoluminal data and extraluminal imaging, in accordance with some applications of the current invention. It is noted that, for some applications, some of the steps shown in FIG. 1 may be practiced, without all of the steps shown in FIG. 1 necessarily being practiced in combination.

In phase 1, extraluminal imaging is activated. Typically the extraluminal imaging is activated at this stage, in order to facilitate determination of the location of a moving data-acquiring portion the endoluminal data-acquisition device by performing image processing on the extraluminal images, and/or in order to facilitate the insertion of the endoluminal data-acquisition device. For some applications, methods other than extraluminal imaging are used for determining the location of the endoluminal data-acquisition device, for example, as described hereinbelow. For some applications (e.g., during insertion of the data-acquisition device into an endobronchial lumen, which may be performed without the guidance of extraluminal imaging), the extraluminal imaging is not activated at this stage.

In phase 2, the extraluminal image stream is typically stabilized, and optionally enhanced, typically in accordance with techniques previously disclosed in US 2008/0221442 to Tolkowsky, and/or US 2010/0228076 to Blank, both of which applications are incorporated herein by reference. For some applications, the extraluminal image stream is stabilized with respect to radiopaque markers on the endoluminal data-acquisition device.

In phase 3, the endoluminal data-acquisition device is inserted towards the designated site. The designated site is typically a site being diagnosed, and at which, subject to the outcome of such diagnosis, the therapeutic device will be positioned and deployed, e.g., the site of an anatomical feature, the implantation site of a previously-implanted device, and/or a site at a defined location with respect to the implantation site, as described hereinabove. The endoluminal data-acquisition device is typically imaged by extraluminal imaging.

In phase 4, endoluminal data, typically images, are acquired by the endoluminal data-acquisition device. Typically, data are acquired at and/or in the vicinity of the designated site. Typically, a plurality of data points (e.g., images) are acquired at respective locations along the lumen. It is noted that, for some applications, data are acquired subsequent to the initial insertion of the data-acquisition device into the lumen. For example, when data are acquired from blood vessels, the data-acquisition device is typically inserted into the blood vessel to beyond the site of interest under extraluminal imaging (e.g., fluoroscopy). Data acquisition is typically performed during (manual or automated) pullback of the data-acquisition device through the blood vessel. In alternative applications, e.g., when data are acquired from an endobronchial airway, data are typically acquired by the data-acquisition device during insertion of the data-acquisition device into the airway.

For some applications, in the course of pullback of the data-acquisition device, the lumen (for example, a coronary artery) also experiences a cyclical motion (for example, due to the cardiac cycle) that causes it to pulsate and move back and forth relatively to the endoluminal data-acquisition device. For some applications, e.g., in the case of a lumen that undergoes such back-and-forth cyclical motion, data acquired by the endoluminal data-acquisition device are gated to the cyclical motion cycle of the lumen. Subsequently, endoluminal data acquired in the course of the pullback at at-least-one specific phase of the motion cycle of the lumen are co-registered with one or more extraluminal images acquired, and gated, at the corresponding at-least-one phase during the pullback, in order to facilitate co-registration of the endoluminal data with the extraluminal images, in accordance with the techniques described herein. For some applications, co-registering endoluminal data with extraluminal images that are gated to the same phase as the phase to which the endoluminal data were gated, reduces distortions in the co-registration that may be introduced due to the cyclical motion of the lumen in the absence of using the aforementioned gating techniques.

For some applications, there is a single, gated extraluminal angiogram image to which all gated endoluminal data are co-registered. For some applications, a three-dimensional model is generated from two (or more) two-dimensional gated angiograms, and the gated endoluminal data is co-registered with that three-dimensional model.

For some applications, the commencement and/or termination of pullback are identified, typically automatically and typically on-line, by means of image processing. For some applications, the image processing is performed by an image comparator which identifies a change (such as in the color of image pixels or in the geometry of image features) in the sequentially-acquired endoluminal images, and interprets the change as indicating the commencement of pullback. For some applications, the image processing is performed by an image comparator which identifies a diminishing change in the sequentially-acquired endoluminal images, and interprets the diminishing change as indicating the termination of pullback.

For some applications, the commencement and/or termination of pullback are identified by means of a signal transmitted by the pullback unit and/or by the endoluminal data acquisition system. For some applications, the commencement and/or termination of pullback are indicated by means of user input.

In phase 5, each applicable image or data point acquired in phase 4 is, typically automatically, assigned a location. The locations assigned to respective data points (e.g., images) correspond to the location of the endoluminal data-acquisition device when the respective data points are acquired. Typically, this step is performed simultaneously with phase 4, such that the system assigns locations corresponding to respective data points at the time of the acquisition of the data points.

For some applications, the location of a data-acquiring portion of the endoluminal data-acquisition device that moves during pullback, and a portion of which is visible in the extraluminal imaging, is identified via image processing. For example, radiopaque markers on a moving imaging portion of the endoluminal data-acquisition device may be identified in extraluminal fluoroscopic images. For some applications, the visible portion is identified and tracked, typically on-line and typically automatically, for example, in accordance with techniques described in US 2010/0228076 to Blank.

For some applications, the location of the moving, visible portion of the endoluminal data-acquisition device is determined relative to an anatomical feature visible in the extraluminal imaging. For some applications, the feature is a bifurcation, a curve or some other unique shape, a partial or total occlusion, a native valve, an aneurism, a septal defect, or a malformation. For some applications, contrast agent is injected in order to make the feature visible (for example, in the case of vasculature that is imaged under fluoroscopy). Typically, the quantity and concentration of the contrast agent that is injected is such that, in some image frames, both the visible portion of the endoluminal data-acquisition device and the anatomical feature may be discerned concurrently in the extraluminal image.

For some applications, the location of the moving, visible portion of the endoluminal data-acquisition device is determined relative to a previously-deployed device visible in the extraluminal imaging. For some applications, the previously-deployed device is a stent, or a graft, or a replacement valve.

For some applications, the location of the moving, visible portion of the endoluminal data-acquisition device is determined relative to visible markers along a guide wire along which the endoluminal data-acquisition device is inserted.

For some applications, the location of the moving, visible portion of the endoluminal data-acquisition device is determined according to its distance along a guide wire along which the endoluminal data-acquisition device is inserted, the distance typically being measured relative to the distal tip of a guiding catheter through which the guide wire was previously inserted (or relative to any other of the aforementioned visible features). For some applications, the endoluminal data-acquisition device includes a portion that substantially does not move with respect to the lumen during pullback, such as an insertion sheath. The location of moving, visible portion of the data-acquisition device is determined, via image processing, with reference to the portion of the device that substantially does not move with respect to the lumen during pullback.

For some applications, the location of the moving visible portion of the endoluminal data-acquisition device is determined by means of display coordinates. Typically, for such applications, when an endoluminal therapeutic device is subsequently inserted into the lumen in order to treat the designated site, the same viewing angle of the extraluminal imaging device relative to the lumen, and the same zoom level of the extraluminal imaging are used as were used to image the endoluminal data-acquisition device inside the lumen. For such applications, the position of the subject typically remains substantially unchanged between the insertion of the data-acquisition device and the insertion of the therapeutic device. Thus, the location of the endoluminal data-acquisition device within the lumen may be matched with the location of the therapeutic device that is subsequently inserted into the lumen.

For some applications, the location of the moving, visible portion of the endoluminal data-acquisition device is determined by determining a distance travelled by the device along the lumen, from a known starting location. For some applications, the distance is measured by a pullback unit to which the device is connected. For some applications, the distance is measured by a longitudinal position/movement sensor coupled to apparatus through which the endoluminal data-acquisition device is inserted, e.g., as described hereinbelow with reference to FIG. 2. For some applications, the apparatus is a guiding catheter. Typically, the sensor measures the extent of longitudinal movement (e.g., insertion, pullback) of a proximal portion of the device. For some applications, the sensor is optical (e.g., laser-based), or mechanical, or electric, or magnetic, or any combination thereof. For some applications, in response to measuring the extent of the longitudinal motion of the proximal portion of the device, the system estimates a distance by which the moving, data-acquiring portion has moved along the lumen (typically, along a center line of the lumen), typically automatically and typically on-line. The center line is determined, typically automatically, in accordance with techniques described in US 2010/0228076 to Blank, which is incorporated herein by reference.

For some applications, the location of the moving portion of the endoluminal data-acquisition device is determined according to techniques described in US Patent Application 2006/0241465 and US Patent Application 2007/0038061, both to Huennekens, and both of which applications are incorporated herein by reference. For some applications, techniques as described in U.S. Pat. No. 5,357,550 to Asahina, US 2011/0034801 to Baumgart, and/or U.S. Pat. No. 7,729,746 to Redel are applied, in order to determine the location of the moving portion of the endoluminal data-acquisition device. All of the aforementioned references are incorporated herein by reference.

For some applications, the location of the endoluminal data-acquisition device is determined even in the absence of simultaneous extraluminal imaging. For example, it may be determined that the device is at an anatomical feature such as a bifurcation, based upon the images or data acquired by the device. Subsequently, the device may be pulled back at a known speed, by a pullback unit to which the device is connected. Alternatively, the distance by which the device has been pulled back at the acquisition of respective data points may be measured. Thus, it may be determined, at the time of acquisition of a given image or a given data point, what is the location of the device relative to the anatomical feature. Separately (before or after acquisition of the endoluminal data), the anatomical feature is identified in an extraluminal image of the lumen. Based upon the location of the anatomical feature in the extraluminal image, endoluminal data points (e.g., images) are assigned to respective locations within the extraluminal image.

For some applications, other techniques are applied, e.g., techniques described hereinbelow with reference to FIG. 3 are applied, in order to determine the location of the endoluminal data-acquisition device when the respective data points (e.g., images) are acquired.

In phase 6, the endoluminal data-acquisition device is typically retrieved from the designated site (and, further typically, withdrawn from the lumen), in order to accommodate the insertion of an endoluminal device (e.g., an endoluminal therapeutic device) into the lumen.

In phase 7, while observing extraluminal images of the luminal segment comprising the designated location, one or more locations along that section are indicated by a user input device. In response thereto, the previously-acquired endoluminal images corresponding to the one or more locations are displayed. For some applications, the user input device is used to select the one or more locations. Typically, the user designates a location using the user input device, and, in response thereto, typically automatically and on-line, the system identifies a location along the lumen (e.g., along the luminal center line) as corresponding to the designated location, and retrieves and displays a corresponding endoluminal image. For some applications, the center line is generated in accordance with techniques described in US 2010/0220917 to Steinberg, which is incorporated herein by reference.

Alternatively or additionally, by observing an angiogram frame side by side with endoluminal image frames of the luminal segment comprising the designated location, one or more locations along the section are indicated by a user input device with respect to endoluminal imaging data. For some applications, the user indication is made upon the endoluminal image stack. For some applications, the user indication is made by browsing through the endoluminal images. In response to receiving the user indication, the location along the lumen (e.g., along the luminal center line) within the angiogram corresponding to the location indicated with respect to an endoluminal image or the endoluminal image stack is determined and indicated.

Typically, a clinical diagnosis is facilitated by an operator viewing previously-acquired endoluminal images corresponding to the one or more locations selected on extraluminal images of the luminal segment, or by the operator viewing indications of locations on an extraluminal image that correspond to one or more locations selected with respect to endoluminal images or an endoluminal image stack, as described with reference to phases 7. Alternatively, a clinical diagnosis is made by the operator reviewing the extraluminal images and/or the endoluminal data (and/or by reviewing other data), without performing phases 7. Typically, a therapeutic process, such as the one described in phase 8 and beyond, is performed based upon the clinical diagnosis made by the operator.

In phases 8, an endoluminal therapeutic device is inserted to the designated location under extraluminal imaging. Typically, stabilization (and optionally also enhancement) is applied, typically on-line and typically automatically, to the extraluminal image stream, in a generally similar manner to that described with reference to phases 2. At least a portion of a therapy-applying portion of the endoluminal therapeutic device, or a probe used for the insertion of the therapeutic device (i.e., an insertion probe) that moves with respect to the lumen, is typically visible in the extraluminal images. For example, the therapy-applying portion may include radiopaque markers, for applications in which the extraluminal imaging is performed via fluoroscopy.

In phases 9, the current location of the moving, visible portion of the endoluminal therapeutic device or the insertion probe is determined, typically on-line and typically automatically. Typically, the current location of the device is determined while the device is at or in the vicinity of the designated site. Typically, phase 9 is performed simultaneously with phases 8, i.e., while the endoluminal therapeutic device is at respective current locations, the current location of the device is determined by the system.

For some applications, the location of the portion of the endoluminal therapeutic device or of the insertion probe that is visible in the extraluminal imaging is identified via image processing. For example, radiopaque markers on the endoluminal therapeutic device may be identified in extraluminal fluoroscopic images. For some applications, the visible portion is identified and tracked, typically on-line and typically automatically, for example, in accordance with techniques described in US 2010/0228076 to Blank.

For some applications, the location of the moving, visible portion of the endoluminal therapeutic device or the insertion probe is determined relative to an anatomical feature visible in the extraluminal imaging. For some applications, the feature is a bifurcation, a curve or some other unique shape, a partial or total occlusion, a native valve, an aneurism, a septal defect, or a malformation. For some applications, contrast agent is injected, in order to make the feature visible (for example, in the case of vasculature that is imaged under fluoroscopy). Typically, the quantity and concentration of the contrast agent that is injected is such that, in some image frames, both the visible portion of the endoluminal data-acquisition device and the anatomical feature may be discerned concurrently in the extraluminal image.

For some applications, the location of the moving, visible portion of the endoluminal therapeutic device or the insertion probe is determined relative to a previously-deployed device visible in the extraluminal imaging. For some applications, the device is a stent, or a graft, or a replacement valve.

For some applications, the location of the moving, visible portion of the endoluminal therapeutic device or the insertion probe is determined relative to visible markers along a guide wire along which the device is inserted.

For some applications, the location of the moving, visible portion of the endoluminal therapeutic device or the insertion probe is determined according to its distance along a guide wire along which the device and/or the probe is inserted, the distance typically being measured relative to the distal tip of a guiding catheter through which the guide wire was previously inserted. For some applications, the endoluminal therapeutic device includes a portion that substantially does not move with respect to the lumen during a stage of the advancement of the therapy-applying portion of the device, such as an insertion sheath. The location of moving, visible portion of the endoluminal therapeutic device is determined, via image processing, with reference to the portion of the device that substantially does not move with respect to the lumen.

For some applications, the location of the moving, visible portion of the endoluminal therapeutic device or the insertion probe is determined by determining a distance travelled by the device along the lumen, from a known starting location. For some applications, such a distance is measured by a pullback unit to which the device is connected. For some applications, the distance is measured by a longitudinal position/movement sensor coupled to an apparatus through which the endoluminal data-acquisition device is inserted, e.g., as described hereinbelow with reference to FIG. 2. For some applications, the apparatus is a guiding catheter. Typically, the sensor measures the extent of longitudinal movement (e.g., insertion, pullback) of a proximal portion of the device. For some applications, the sensor is optical (e.g., laser-based), or mechanical, or electric, or magnetic, or any combination thereof. For some applications, in response to measuring the extent of the longitudinal motion of the proximal portion of the device, the system estimates a distance by which the therapy-applying portion of the device has moved along the lumen (e.g., along a center line of the lumen), typically automatically and typically on-line. The center line is determined, typically automatically, in accordance with techniques described in US 2010/0228076 to Blank.

For some applications, the location of the moving, visible portion of the therapeutic device is determined by means of display coordinates. Typically, as described hereinabove, the current location of the therapeutic device may be matched with a location of the endoluminal data-acquisition device by using the same viewing angle of the extraluminal imaging device relative to the lumen, and by using zoom level of the extraluminal imaging, as were used for the extraluminal imaging of the endoluminal data-acquisition device.

In phase 10, data points (e.g., images) that were previously acquired by the endoluminal data-acquisition device at or near the location are retrieved and associated, typically on-line and typically automatically, with the extraluminal imaging, while the device is at or near the same location.

In phase 11, data points (e.g., images) that were previously acquired by the endoluminal data-acquisition device at or near the location are displayed together with the extraluminal imaging. Typically, data points are displayed that correspond to the current location of the endoluminal therapeutic device (as determined in phases 9). Typically, phases 10 and 11 are performed in real time with respect to phases 8 and 9. Thus, while the endoluminal therapeutic device is at respective current locations inside the lumen, the location of the device is determined, and the endoluminal data points associated with the location are retrieved and displayed.

For some applications, endoluminal and extraluminal images corresponding to the same location (typically, the current location of the endoluminal therapeutic device) are displayed side by side. For some applications, endoluminal and extraluminal images corresponding to the same location (typically, the current location of the endoluminal therapeutic device) are merged, such as by means of fusion or overlay. For some applications, quantitative vessel analysis (QVA) data are displayed, the data typically corresponding to the current location of the endoluminal therapeutic device. Typically, the QVA data are generated automatically and on-line in accordance with techniques described in US 2010/0228076 to Blank, which is incorporated herein by reference. For example, the current location of one or more markers of the therapeutic device may be determined via image-processing, and QVA data corresponding to the current location of the markers may be generated and displayed, typically automatically, and typically on-line. Alternatively, in response to a location within the lumen being indicated via a user input device, QVA data corresponding to the location may be generated and displayed, typically automatically, and typically on-line.

For some applications, enhanced extraluminal images of a lumen segment comprising the location are generated, for example, in accordance with techniques described in US 2010/0228076 to Blank, which is incorporated herein by reference.

For some applications (for example, in applications in which the endoluminal data-acquisition device is an ultrasound probe), image slices corresponding to a luminal segment at or around the designated site are displayed as stacked.

Typically, the effect of co-displaying the endoluminal data with the extraluminal imaging is as if the endoluminal therapeutic device is being positioned and deployed under real-time extraluminal imaging and using real-time endoluminal data acquisition, at and in the vicinity of the designated site.

For some applications, phases 1 through 7 (or any applicable subset of those phases) are repeated subsequent to the deployment of the therapeutic device, such as in the course of performing a clinical evaluation of the outcome of the deployment of that device. For example, phases 1-7 may be repeated so as to facilitate the co-display of endoluminal images of the lumen, post-deployment of the device, with one or more extraluminal images of the lumen.

For some applications, a procedure is carried out generally in accordance with the flowchart shown in FIG. 1, in which one, some, or all of the following apply:

The luminal structure is a coronary artery.

The designated site for diagnosis and treatment is a partially-occluded segment of the artery.

The endoluminal data-acquisition device is an IVUS probe, capable of identifying coronary disease in the luminal wall.

The extraluminal imaging is performed via fluoroscopy.

The fluoroscopic image stream is, for some applications, stabilized on-line.

The endoluminal therapeutic device that is positioned and deployed at the site of the occlusion is a balloon-expandable stent.

The balloon carrying the stent comprises radio-opaque markers at its proximal and distal ends, the markers being visible under fluoroscopic imaging.

For some such applications, images generated by the IVUS probe within the coronary vessel are used in conjunction with the extraluminal fluoroscopic image stream in the following manner:

i. An IVUS catheter is inserted to the site of an occlusion under fluoroscopic imaging, to inspect endoluminal anatomy.

ii. Optionally, the fluoroscopic image stream is stabilized. For some applications, the image stream is stabilized with respect to radiopaque segments of the IVUS catheter.

iii. The image slices generated by the IVUS are recorded and stored in tandem with the visual location (such as display coordinates) of the distal tip of the IVUS catheter as seen by the image-stabilized stream of the fluoroscopy.

iv. The IVUS catheter is retrieved to make room for balloon/stent deployment.

v. A catheter with a balloon and/or stent is inserted to the site of the occlusion, under fluoroscopic imaging.

vi. The location of the distal tip of the catheter carrying the balloon and/or stent is visually recognized (such as via display coordinates).

vii. The IVUS images previously recorded at the same location are displayed, together with the fluoroscopic images. For some applications, the IVUS images are displayed in a separate window (but on the same screen as the fluoroscopic images). For some applications, the IVUS images are displayed on a separate screen. For some applications, the IVUS images being displayed are two-dimensional (also known as "slices"). For some applications, a stack comprising multiple slices is displayed. For some applications, a three-dimensional "tunnel-like" reconstruction of the IVUS images of the vessel (or a section thereof) is displayed. For some applications, the IVUS images are overlaid on the fluoroscopic images. For some applications, the IVUS images are fused with the fluoroscopic images.

viii. As a result, the balloon and/or stent may be positioned and deployed based upon an on-line combination of real-time fluoroscopic images and of IVUS images recorded earlier (for example, several minutes earlier).

For some applications, data acquired by a first endoluminal modality (e.g., IVUS) are co-registered with the fluoroscopic image stream, in accordance with the applications described hereinabove. Subsequently, data acquired by a second endoluminal modality (e.g., OCT) are co-registered with the fluoroscopic image stream, in accordance with the applications described hereinabove. Consequently, due to both data sets being co-registered with the fluoroscopic image stream, the two data sets are co-registered to one another. For some applications, the two endoluminal data sets are displayed as overlaid or otherwise merged with one another.

For some applications, generally similar steps to those described with reference to FIG. 1 are performed, except for the following differences. In phases 8, instead of a therapeutic endoluminal device being inserted into the lumen, a second endoluminal data-acquisition device is inserted into the lumen. Typically, the first and second endoluminal data-acquisition devices acquire endoluminal images using respective imaging modalities. For example, in phase 3, an IVUS probe may be inserted into the lumen, and in phase 8 an OCT probe may be inserted into the lumen, or vice versa.

In phases 9, the current location of the second endoluminal data-acquisition device is determined, for example, using any of the techniques described herein (such as, by performing image processing on extraluminal images of the second endoluminal data-acquisition device inside the lumen). In phases 10 and 11, endoluminal images which were previously acquired using the first data-acquisition device at the current location of the second endoluminal data-acquisition device are retrieved and displayed, typically on-line and typically automatically.

Typically, the endoluminal images which were acquired using the first data-acquisition device at the current location of the second endoluminal data-acquisition device are displayed together with endoluminal images that are being acquired in real time by the second endoluminal data-acquisition device, while the second endoluminal data-acquisition device is at the current location. For some applications, endoluminal images that are acquired in real time by the second endoluminal data-acquisition device, while the second endoluminal data-acquisition device is at the current location, are displayed together with an indication of the current location of the second endoluminal data-acquisition device with respect to an endoluminal image stack generated using endoluminal images that were previously acquired by the first endoluminal data-acquisition device. For some applications, using the above-described technique, data acquired by first and second endoluminal data acquisition devices are registered with respect to one another, and the co-registered data are displayed subsequent to termination of the acquisition of endoluminal images by both the first and the second endoluminal data-acquisition devices. For some applications, endoluminal images corresponding to the current location of the second endoluminal data-acquisition device that were acquired by the first endoluminal data acquisition device, and/or by the second endoluminal data acquisition device, are co-displayed with an indication of the current location of the second endoluminal data-acquisition device on an extraluminal image of the lumen, using the techniques described herein.

For some applications, techniques described herein (e.g., techniques described with reference to FIGS. 1-11) are performed by a system that includes at least one processor, for use with an endoluminal data-acquisition device that is configured to acquire a set of endoluminal data-points with respect to a lumen of a body of a subject at respective locations inside the lumen, and a second endoluminal device. The processor typically includes (a) location-association functionality configured to associate a given endoluminal data point acquired by the endoluminal data-acquisition device with a given location within the lumen, (b) location-determination functionality configured, in an extraluminal image of the second endoluminal device, to determine by means of image processing, a current location of at least a portion of the second endoluminal device inside the lumen, and (c) display-driving functionality configured, in response to determining that the second endoluminal device is currently at the given location, to drive a display to display an indication of the endoluminal data point associated with the given location.

Figure 2A:
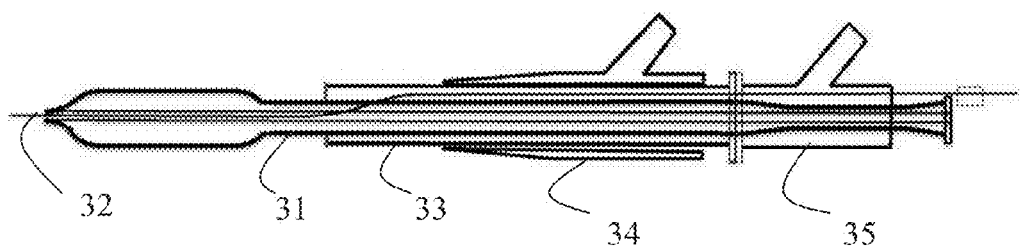
FIGS. 2A-B are schematic illustrations of an endoluminal device being inserted into a lumen, and (in FIG. 2B) a sensor for sensing the distance travelled through the lumen by the endoluminal device relative to a known starting location, in accordance with some applications of the present invention.
Figure 2B:
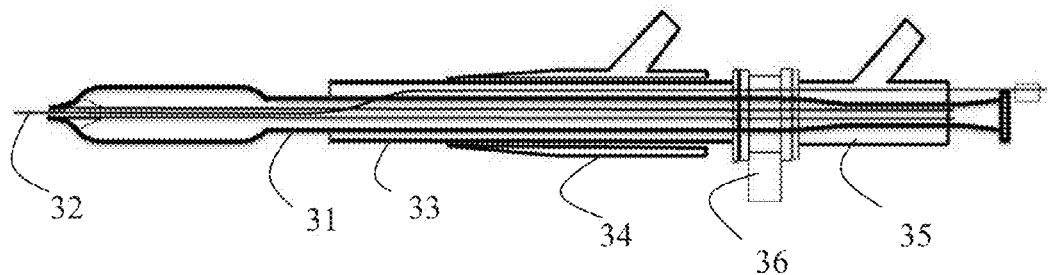

Reference is now made to FIG. 2A-B, which are schematic illustrations of an endoluminal device 31 (e.g., an IVUS probe) being inserted into a lumen, and (in FIG. 2B) a sensor 36 for sensing the distance travelled through the lumen by the endoluminal device relative to a known starting location, in accordance with some applications of the present invention. FIG. 2A shows IVUS probe 31 being inserted, along a guide wire 32, through a guiding catheter 33. Guiding catheter 33 is typically inserted through a sheath 34 and is connected to a Y connector 35. FIG. 2B shows sensor 36 disposed between guiding catheter 33 and Y connector 35. Sensor 36 measures the longitudinal motion of a proximal portion of IVUS probe 31 into (e.g., during insertion) and/or out of (e.g., during pullback/withdrawal) guiding catheter 33. For some applications, the sensor is optical (e.g., laser-based), mechanical, electric, magnetic, or any combination thereof. For some applications, in response to measuring the longitudinal motion of the proximal portion of the IVUS probe, the system estimates a distance by which the data-acquisition portion of the IVUS probe has moved along a the lumen (typically, along the center line of the lumen), typically automatically and typically on-line. The center line is determined, typically automatically, in accordance with techniques described in US 2010/0228076 to Blank, which is incorporated herein by reference.

It is noted that, for some applications, sensor 36 is used for other endoluminal applications in which a luminal roadmap is generated, and subsequently the sensor is used for determining the current location of an endoluminal tool along the roadmap. For some applications, the location of the endoluminal tool is determined while the endoluminal tool is not being imaged by extraluminal imaging. For some applications, the roadmap is generated and/or utilized in accordance with techniques described in US 2008/0221442 to Tolkowsky, which is incorporated herein by reference. For some applications, the roadmap is generated and/or utilized in accordance with techniques described in US 2010/0160764 to Steinberg, which is incorporated herein by reference.

Reference is now made to FIG. 3, which is a flow chart, at least some of the steps of which are used in the course of co-use of endoluminal data (e.g., generated by an IVUS probe) and extraluminal imaging (e.g., fluoroscopic imaging), in accordance with some applications of the current invention. It is noted that although the steps described with reference to FIG. 3 are described with reference to IVUS imaging, the scope of the present invention includes applying these steps to any other forms of endoluminal data-acquisition. It is noted that, for some applications, some of the steps shown in FIG. 3 may be practiced without all of the steps shown in FIG. 3 necessarily being practiced in combination.

In phase 1, an IVUS probe is inserted to the site of an occlusion under fluoroscopic imaging, to acquire images of the endoluminal anatomy.

In phases 2, the fluoroscopic image stream is typically stabilized. For some applications, the image stream is stabilized with respect to radiopaque segments of the IVUS probe.

In phase 3, the IVUS probe is stopped at a location that is distal to the designated luminal site (the designated site being the site of a lesion, for example, as described hereinabove).

In phase 4, contrast agent is injected and an angiogram sequence is generated, under fluoro or cine.

In phase 5, an initial best angiogram frame is selected, typically automatically and typically on-line. The initial best angiogram frame is typically selected based upon the following criteria: (a) the frame is acquired at a desired cardiac phase (typically end diastole) (b) in the image frame, contrast agent highlights the vessel, and (c) radiopaque elements (such as markers) at the distal section (i.e., in the vicinity of the imaging sensor) of the IVUS probe are visible in the image frame.

Figure 4:
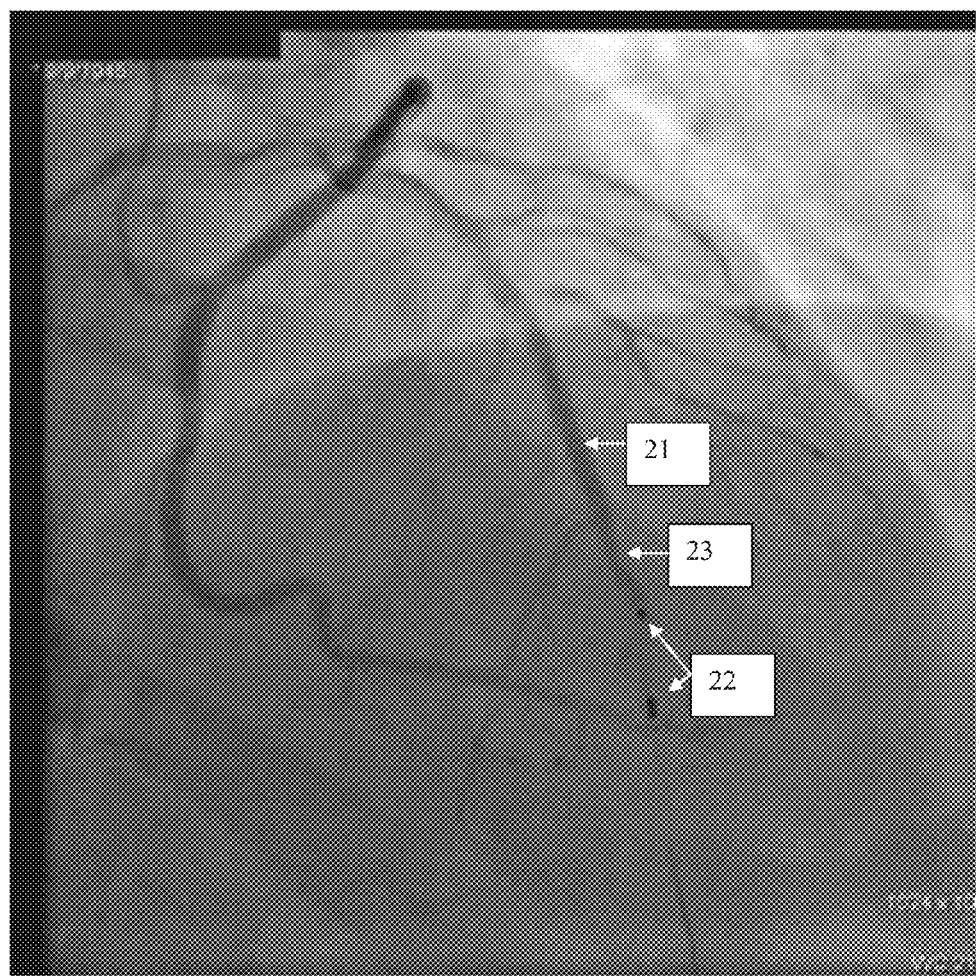
FIG. 4 shows an initial best angiogram of a luminal segment, the initial best angiogram being generated prior to the commencement of the pullback of an endoluminal imaging probe, in accordance with some applications of the present invention.

Reference is now made to FIG. 4, which shows an initial best angiogram of lumen 21, in accordance with some applications of the present invention. As shown in FIG. 4, radiopaque markers 22 of the IVUS probe are typically seen distally to lesion 23 in the initial best angiogram.

In phase 6, pullback of the IVUS probe, typically at a known and steady rate of distance per second (such as by means of automated pullback), commences. The image slices generated by the IVUS probe along the pullback are recorded and stored in an image sequence. For some applications, the pullback is performed manually.

For some applications, the image slices generated by the IVUS probe along the pullback are recorded and stored in an image sequence, and simultaneously, a longitudinal position/movement sensor attached to apparatus through which the IVUS probe is inserted measures the longitudinal location of a proximal portion of the IVUS probe relative to the starting location of the proximal portion of the probe, e.g., as described with reference to FIG. 2. The locations of the IVUS probe as determined by the sensor, when respective IVUS image slices were recorded, are stored by the system.

For some applications, in the course of pullback, the lumen also experiences cyclical motion (typically due to the cardiac cycle) that causes it to pulsate and move back and forth relatively to the IVUS probe. For some applications, e.g., in the case of a lumen that undergoes such back-and-forth cyclical motion, data acquired by the IVUS probe is gated to the cyclical motion cycle of the lumen. Subsequently, IVUS images acquired in the course of the pullback at at-least-one specific phase (for example, an end-diastolic phase) of the motion cycle of the lumen are co-registered with one or more fluoroscopic images acquired, and gated, at the corresponding at-least-one phase during the pullback, in order to facilitate the co-registration of the IVUS images to the fluoroscopic images. For some applications, co-registering IVUS images with angiographic images that are gated to the same phase as the phase to which the IVUS images were gated, reduces distortions to the co-registration that may be introduced due to the cyclical motion of the lumen in the absence of using the aforementioned gating techniques.

For some applications, as described hereinbelow, in a subsequent phase (e.g., phase 13), in response to the user indicating location on the extraluminal image, the system retrieves and displays a corresponding endoluminal image frame, typically automatically and typically on-line. For some applications, the system displays the closest gated endoluminal image frame corresponding to the location indicated by the user, even though there may be a non-gated image frame the location of which more closely corresponds to the location indicated by the user. Alternatively, the system displays the endoluminal image frame the location of which most closely corresponds to the location indicated by the user, irrespective of the phase of the cardiac cycle at which the endoluminal image frame was acquired.

For some applications, there is a single, gated extraluminal angiogram image to which all gated endoluminal data are co-registered. For some applications, a three-dimensional model is generated from two (or more) two-dimensional gated angiograms, and the gated endoluminal data is co-registered with that three-dimensional model.

For some applications, the commencement of pullback is identified, typically automatically and typically on-line, by means of image processing. For some applications, the image processing is performed by an image comparator which identifies a significant change (such as in the color of image pixels or in the geometry of image features) in the sequentially-acquired endoluminal images, and interprets the change as indicating the commencement of pullback. For some applications, the commencement of pullback is identified by means of a signal transmitted by the pullback unit and/or by the endoluminal data acquisition system. For some applications, the commencement of pullback is indicated by means of user input.

In phases 7, the pullback is stopped at a location that is proximal to the designated lesion. For some applications, the termination of pullback is identified, typically automatically and typically on-line, by means of image processing. For some applications, the image processing is performed by an image comparator which identifies a diminishing change in the sequentially-acquired endoluminal images, and interprets the diminishing change as indicating the termination of pullback. For some applications, the termination of pullback is identified by means of a signal transmitted by the pullback unit and/or by the endoluminal data acquisition system. For some applications, the termination of pullback is indicated by means of user input.

In phases 8, contrast agent is injected and an angiogram sequence, under fluoro or cine, is generated.

In phases 9, a post-pullback best angiogram frame is selected, typically automatically and typically on-line. The post-pullback best angiogram frame is typically selected based upon the following criteria: (a) the frame is acquired at a desired cardiac phase (typically end diastole) (b) in the image frame, contrast agent highlights the vessel, and (c) radiopaque elements (such as markers) at the distal section (i.e., in the vicinity of the imaging sensor) of the IVUS probe are visible in the image frame.

Figure 5:
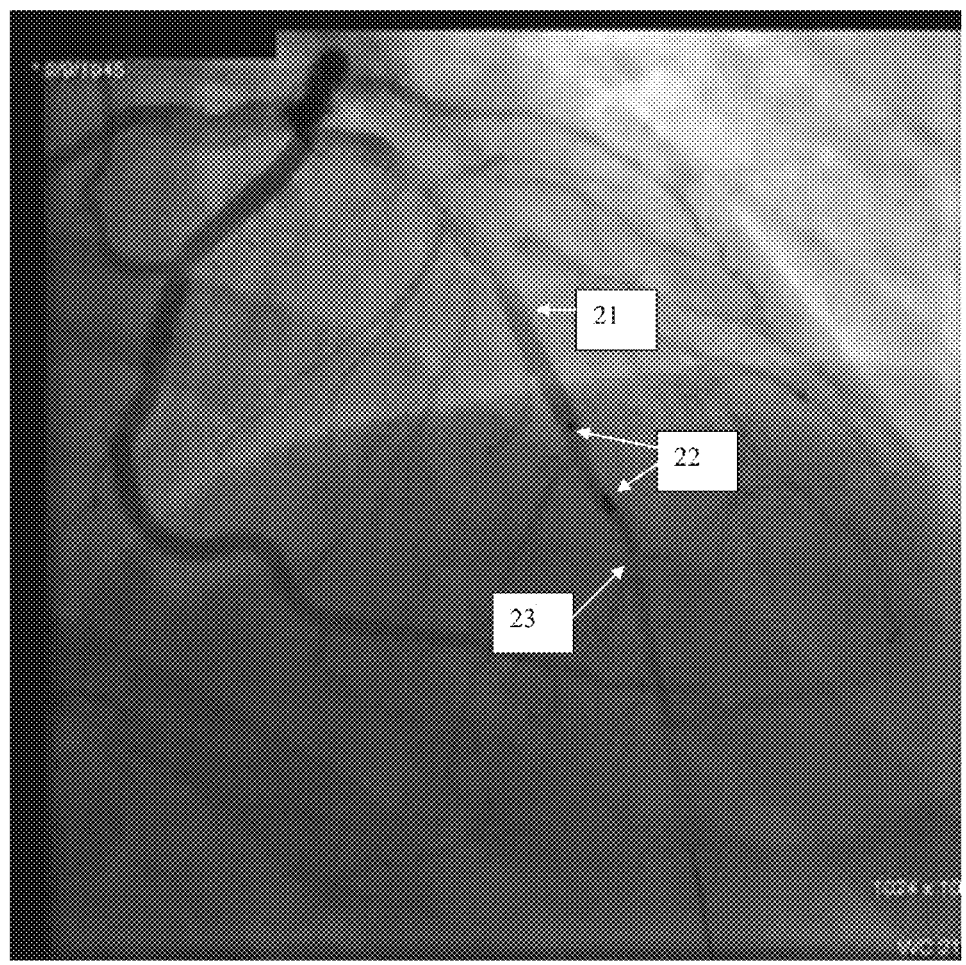
FIG. 5 shows a post-pullback best angiogram of a luminal segment, the post-pullback best angiogram being generated subsequent to the termination of the pullback of an endoluminal imaging probe, in accordance with some applications of the present invention.

Reference is now made to FIG. 5, which shows a post-pullback best angiogram of lumen 21, in accordance with some applications of the present invention. As shown in FIG. 5, radiopaque markers 22 of the IVUS probe are typically seen proximally to lesion 23, in the post-pullback best angiogram.

In phase 10, the initial best angiogram and the post-pullback best angiogram are co-registered to one another, typically automatically and typically on-line, according to techniques described in US 2010/0222671 to Cohen, which is incorporated herein by reference. A combined best angiogram is generated by co-registering the initial and post-pullback best angiograms. Typically, in the combined best angiogram, the vessel and two sets of the IVUS probe's radiopaque elements (one of the sets being from the initial best angiogram and the second set being from the post-pullback best angiogram) are visible.

Alternatively, the combined best angiogram is generated by adding the markers that are visible in the initial best angiogram onto the post-pullback best angiogram using the aforementioned registration techniques. Further alternatively, the combined best angiogram is generated by adding the markers that are visible in the post-pullback best angiogram onto the initial best angiogram using the aforementioned registration techniques.

Figure 6:
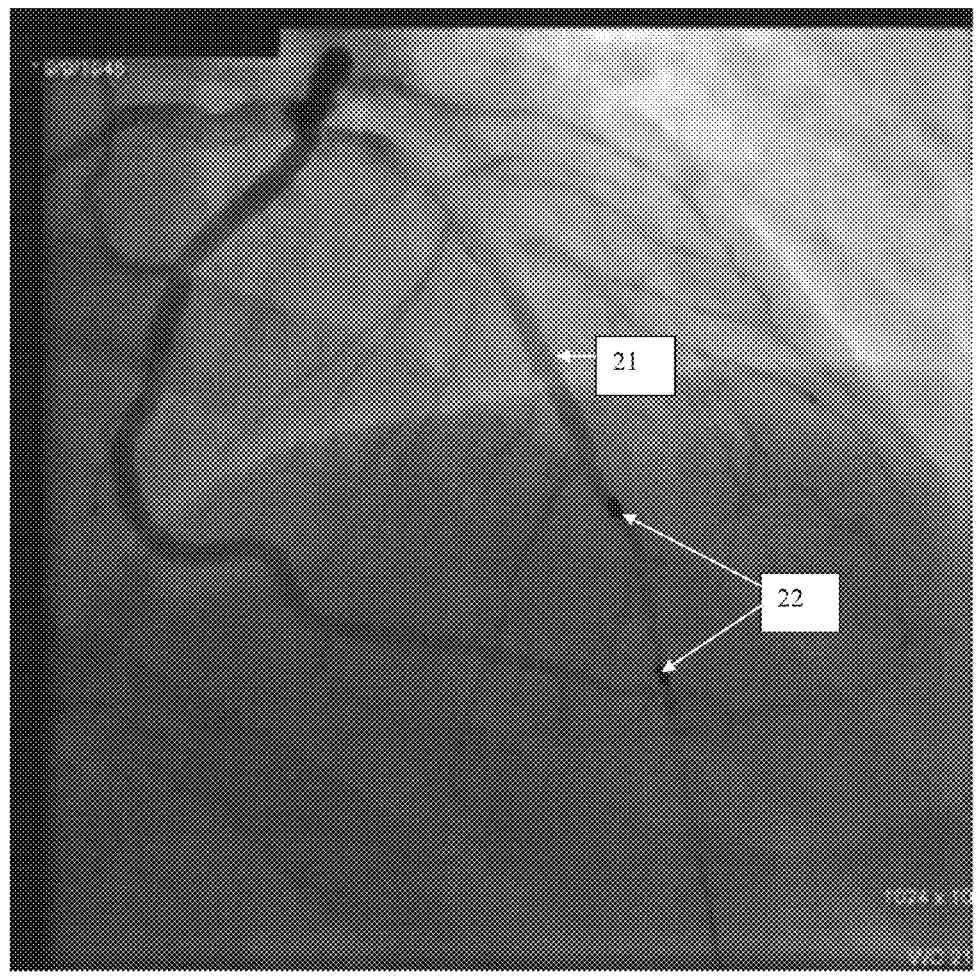
FIG. 6 shows a combined best angiogram of a luminal segment, the combined best angiogram being generated by co-registering the initial best angiogram and the post-pullback best angiogram, in accordance with some applications of the present invention.

Reference is now made to FIG. 6, which shows a combined best angiogram of lumen 21, in accordance with some applications of the invention. As shown in FIG. 6, distal radiopaque markers 22 of the IVUS probe are shown (e.g., overlaid) at their locations before and after the pullback on the combined best angiogram of the lumen.

In phase 11, a center line typically is generated on the combined best angiogram (for example, in accordance with the techniques described in US 2010/0220917 to Steinberg, which is incorporated herein by reference) from the proximal to the distal marker locations along the vessel. The system generates an index of the IVUS slices, based upon the estimated location of the IVUS probe marker (from the distal-most marker location the proximal-most marker location) along the lumen (and typically along the center-line), at the time of acquisition of respective slices.

For some applications, the system interpolates between the distal-most location of the IVUS marker along the lumen (e.g., along the center line of the lumen) and the proximal-most location of the IVUS marker along the lumen (e.g., along the center line), in order to determine the location of the IVUS marker corresponding to intermediate IVUS slices. For some applications, in indexing the IVUS slices between the proximal-most and distal-most slices, it is assumed that pullback of the IVUS probe was performed at a linear rate, and that there is therefore an equal distance between any pair of adjacent IVUS slices, and any other pair of adjacent IVUS slices (i.e., it is assumed that between acquiring respective successive pairs of slices, the probe travelled equal distances). For some applications, in indexing the IVUS slices between the proximal-most and distal-most slices, the system accounts for the IVUS probe acquiring IVUS images at varying frame rates.

In phase 12, the IVUS probe is retrieved.

In phase 13, while observing angiographic images of the luminal segment comprising the designated location, one or more locations along that section are indicated by a user input device. Typically, the user designates a location using the user input device, and the system identifies a location along the lumen (typically, along the luminal center line) as corresponding to the designated location, and retrieves the previously-acquired IVUS images corresponding to the location, based upon the indexing of the IVUS frames. The retrieved endoluminal image frames previously recorded at the selected location are displayed.

Alternatively, by observing an angiogram frame side by side with endoluminal image frames of the luminal segment comprising the designated location, one or more locations along the section are indicated by a user input device with respect to endoluminal imaging data. For some applications, the user indication is made upon the endoluminal image stack. For some applications, the user indication is made by browsing through the endoluminal images. In response to receiving the user indication, the location along the lumen (e.g., along the luminal center line) within the angiogram corresponding to the location indicated with respect to an endoluminal image or the endoluminal image stack is determined and indicated. For some applications, the corresponding location on the angiogram is determined based upon the indexing of the IVUS slices, based upon the location of the IVUS probe marker along the lumen (e.g., along the luminal center-line), at the time of acquisition of respective slices, as described hereinabove with reference to phase 11.

For some applications, the location corresponding to the location indicated with respect to the endoluminal image frames or the endoluminal image stack is displayed on the combined best angiogram. Alternatively, (in cases in which a plurality of angiograms are acquired during pullback, as described hereinbelow) the location is displayed on the angiogram that was acquired closest in time to the acquisition of the endoluminal image frame indicated by the user input device.

Figure 7:
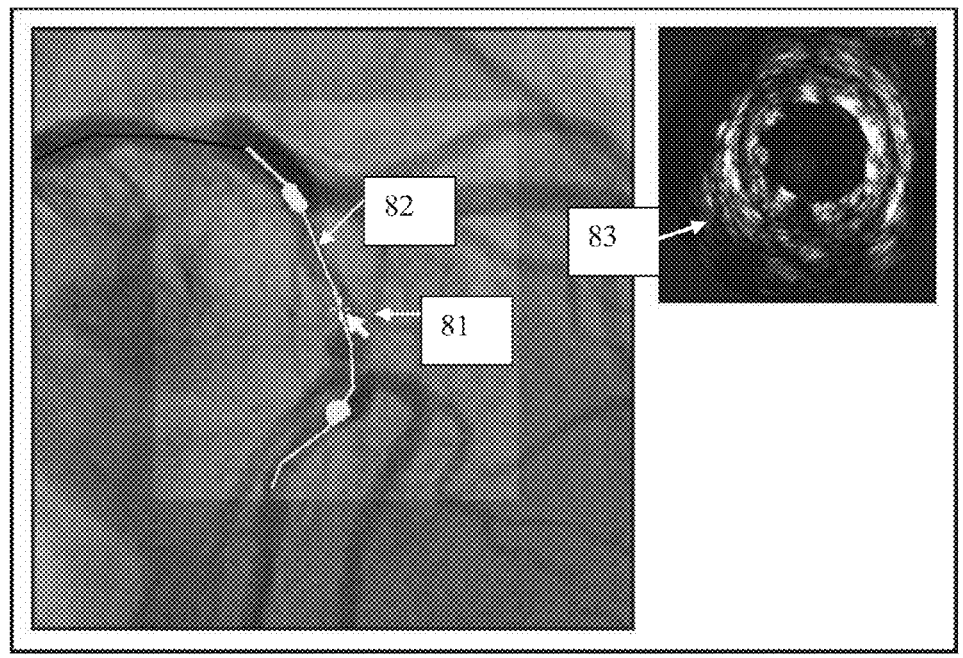
FIG. 7 shows the co-use of previously-acquired endoluminal images and an extraluminal fluoroscopic image, in accordance with some applications of the present invention.

Reference is now made to FIG. 7, which is schematic illustration of a screen on which an IVUS image 83 is displayed, in accordance with some applications of the present invention. Typically, upon receiving an indication from the user of a location along the lumen (e.g., along the luminal center line 82, for example, by the user pointing cursor 81 to a location on the screen, and the system determining a location along the center line corresponding to the location), IVUS image 83 which was previously acquired at that location is displayed. For some applications, an IVUS stack comprising data from IVUS images that were previously acquired along a section of the lumen (e.g., along a section of center line 82) of which the user-indicated location is a middle point or one of the end points, is displayed. For some applications, an IVUS stack comprising data from IVUS images that were previously acquired between two user-indicated locations along the lumen (e.g., along center line 82) is displayed.

Typically, a clinical diagnosis is facilitated by an operator viewing previously-acquired endoluminal images corresponding to the one or more locations selected on extraluminal images of the luminal segment, or by the operator viewing indications of locations on an extraluminal image that correspond to one or more locations selected on endoluminal images, as described with reference to phase 13. Alternatively, a clinical diagnosis is made by the operator reviewing the extraluminal images and/or the endoluminal data (and/or reviewing other data), without performing phases 13. Typically, a therapeutic process, such as the one described in phases 14 and beyond, is performed based upon the clinical diagnosis made by the operator.

In phases 14, a catheter with a balloon and/or stent is inserted to the area of the designated site, under fluoroscopic imaging. Typically, the fluoroscopic image stream is stabilized with respect to radiopaque markers on the catheter via which the balloon and/or the stent is inserted.

In phases 15, upon reaching a desired location within the blood vessel (such as the vicinity of the designated site), contrast agent is injected and an angiogram sequence is generated under fluoro or cine.

In phases 16, a current best angiogram frame is selected, typically automatically and typically on-line. The current best angiogram frame is typically selected based upon the following criteria: (a) the frame is acquired at a desired cardiac phase (typically end diastole) (b) in the image frame, contrast agent highlights the vessel, and (c) radiopaque elements (such as markers) at the distal section (i.e., in the vicinity of the imaging sensor) of the balloon/stent catheter are visible in the image frame.

In phase 17, the combined best angiogram and the current best angiogram are co-registered to one another, typically automatically and typically on-line, according to techniques described in 2010/0222671 to Cohen, which is incorporated herein by reference. A multi-combined best angiogram is generated by co-registering the combined and current best angiograms. Typically, in the multi-combined best angiogram, the vessel and the two sets of the IVUS probe's radiopaque elements (one of the sets being from the initial best angiogram and the second set being from the post-pullback best angiogram) and the radiopaque markers of the balloon/stent catheter are visible.

In phase 18, a user and/or the system selects a location of interest along the lumen in the multi-combined best angiogram of the lumen. For example, a user or the system may select a location of a point of interest along the balloon/stent (such as the location of one of the balloon/stent markers, or anywhere in between the markers).

In phase 19, based upon the indexing described hereinabove, with reference to phase 11, the IVUS image previously recorded at the selected location (which is typically based upon the current location of the balloon/stent catheter, as described in the previous step (step xvi)) is identified. The corresponding IVUS image is retrieved and displayed, typically automatically and typically on-line, together with the fluoroscopic images. For some applications, the IVUS images are displayed in a separate window (but on the same screen as the fluoroscopic images). For some applications, the IVUS images are displayed on a separate screen. For some applications, the IVUS images that are displayed are two-dimensional (also known as "slices"). For some applications, a stack comprising multiple IVUS slices (such as those corresponding to the longitudinal section between the current locations of the proximal and distal markers of the balloon/stent, and, optionally, beyond the aforementioned current marker locations, in each direction) is displayed.

For some applications, a three-dimensional "tunnel-like" reconstruction of the IVUS images of the vessel (or a section thereof, such as those corresponding to the longitudinal section between the current locations of the proximal and distal markers of the balloon/stent) is generated and displayed. For some applications, the IVUS images are overlaid on the fluoroscopic images. For some applications, the IVUS images are fused with the fluoroscopic images. For some applications, a combination of the aforementioned display techniques is applied. For some applications, an indication of the motion range of the balloon/stent relative to the lumen, resulting from the cardiac cycle, is displayed in conjunction with any of the aforementioned displays of the IVUS images. For some applications, such an indication is generated and/or displayed in accordance with embodiments of US 2010/0222671 to Cohen, which is incorporated herein by reference.

As an alternative or in addition to phases 18 and 19, by observing an angiogram frame (e.g., the multi-combined best angiogram) side by side with endoluminal image frames of the luminal segment comprising the designated location, one or more locations along the section are indicated by a user input device with respect to endoluminal imaging data. For some applications, the user indication is made upon the endoluminal image stack. For some applications, the user indication is made by browsing through the endoluminal images. In response to receiving the user indication, the location along the lumen (e.g., along the luminal center line) within the angiogram frame (e.g., the combined best angiogram) corresponding to the location indicated with respect to the endoluminal image or the endoluminal image stack is determined and indicated.

In phase 20, as a result of displaying the IVUS image or an image derived from the IVUS image (e.g., a fused image), the balloon and/or stent may be positioned and deployed based upon an on-line combination of real-time fluoroscopic images and of IVUS images recorded earlier (for example, more than a minute earlier).

Although phases 14-20 have been described with respect to inserting a balloon and a stent into the lumen, the scope of the present invention includes performing steps 14-20 in conjunction with a different therapeutic device being inserted into the lumen, mutatis mutandis. For example, a guide wire may be inserted into the lumen in order to penetrate an occlusion (e.g., a total occlusion) of the lumen. A radiopaque marker that is visible in extraluminal images (e.g., fluoroscopic and/or angiographic images) is disposed at the distal end of the guidewire. By applying phases 14-20 in conjunction with the insertion of the guidewire through the occlusion, the system facilitates the retrieval and display of endoluminal images (e.g., OCT and/or IVUS images) of the lumen that correspond to the current location of the radiopaque marker of the guidewire. For some applications, the system facilitates the display of the current location of the radiopaque marker of the guidewire with respect to a previously-acquired endoluminal image stack of the lumen.

Typically, in the case of a total occlusion of the lumen, it is not possible to acquire endoluminal images of the occluded segment of the lumen, since the occluded segment is closed. For some applications, in such cases, a forward-looking endoluminal imagining probe is used to acquire endoluminal images of segments of the lumen that are distal to the probe, while the probe is at respective locations within the lumen. Subsequently, when a guidewire is inserted through the lumen, in order to penetrate the occlusion, an endoluminal image of a segment of the lumen that is distal to the guidewire corresponding to the current location of the guidewire is shown, using the co-registration techniques described herein. Alternatively, when the guidewire is inserted through the lumen the current location of the tip of the guidewire is displayed with respect to an endoluminal image stack of the lumen, the stack being based upon the previously-acquired endoluminal images.

As described hereinabove with reference to FIG. 3, for some applications, initial and post-pullback angiograms are generated in order to determine the locations of the IVUS markers with respect to the lumen before and after pullback. Intermediate marker locations corresponding to intermediate endoluminal images are indexed by interpolating between distal and proximal marker locations that are determined based upon, respectively, the initial and post-pullback angiograms. Typically, in indexing the IVUS slices between the proximal-most and distal-most slices, it is assumed that pullback of the IVUS probe was performed at a linear rate and that the frame rate of the IVUS probe was constant. It is therefore assumed that there is an equal distance between any pair of adjacent IVUS slices, and any other pair of adjacent IVUS slices.

Alternatively, as described hereinabove, the system estimates the speed of the pullback of the imaging head of the IVUS probe by measuring the speed of the pullback of a proximal portion of the probe, using a sensor, e.g., as described with reference to FIG. 2. Thus, the system may determine an initial location of the IVUS markers by acquiring an initial angiogram, and may determine subsequent locations of the IVUS markers based upon the estimated speed of the pullback of the IVUS probe and the time that has elapsed between the commencement of pullback and the estimated speed of the pullback.

Further alternatively, as described hereinbelow with reference to FIG. 8, pullback of the endoluminal imaging probe is performed while the lumen is continuously flushed with contrast agent. This is applicable, for example, in the case of an endoluminal OCT probe, as described hereinbelow. For example, in such cases, the lumen may be continuously flushed with contrast agent for a time period of at least two seconds, and/or for at least 50% (e.g., at least 80%) of the duration of a time period over which the imaging probes acquires the endoluminal images during pullback. In such cases, the entire pullback procedure (or an entire portion thereof) may be performed under angiographic imaging. The endoluminal probe marker locations corresponding to given endoluminal images are determined by identifying marker locations in the angiographic images (e.g., via image processing that is typically performed automatically and on-line), co-registering the angiographic images into a combined best angiogram, and indexing the identified marker locations with respect to the endoluminal images, as described hereinbelow. Intermediate marker locations that do not appear in the combined best angiogram are estimated, as described hereinbelow, with reference to FIG. 8. The aforementioned technique may be typically used to determine marker locations even in cases in which the pullback of the endoluminal imaging probe is not performed at a constant speed, since marker locations that are known are typically relatively close to one another.

Still further alternatively, endoluminal probe marker locations corresponding to respective endoluminal images are determined, by acquiring fluoroscopic images of the probe within the lumen during the pullback (the fluoroscopic images typically being acquired without requiring the injection of contrast materials). The endoluminal probe marker locations corresponding to given endoluminal images are determined by identifying marker locations in the fluoroscopic images (e.g., via image processing) and indexing the identified marker locations with respect to the endoluminal images. Typically, the radiopaque markers of the probe are identified, typically automatically and typically on-line, and their locations are determined, typically automatically and typically on-line, according to their distances along a guide wire along which the probe is inserted. For some applications, the distances are measured relative to the distal tip of a guiding catheter through which the guide wire was previously inserted. Alternatively, the marker locations are measured relative to other portions of the apparatus that are visible in the fluoroscopic images and that are substantially stationary with respect to the lumen during pullback of the probe, as described hereinabove with reference to phase 5 of the flowchart shown in FIG. 1. The aforementioned technique may be used to determine marker locations even in cases in which the pullback of the endoluminal imaging probe is not performed at a constant speed.

For some applications, the determination of marker locations is generally as described with reference to FIG. 3. That is, initial and post-pullback angiograms are generated in order to determine the locations of the IVUS markers with respect to the lumen before and after pullback, and intermediate marker locations corresponding to intermediate endoluminal images are indexed by interpolating between known marker locations. However, as described hereinabove, in indexing the IVUS slices between the slices that were acquired at known marker locations, it is typically assumed that pullback of the IVUS probe was performed at a linear rate, and that there is therefore an equal distance between any pair of adjacent IVUS slices, and any other pair of adjacent IVUS slices. For some applications, in order to overcome errors in the estimated marker locations due to non-linear pullback of the probe (and/or for a different reason), additional intermediate marker locations are identified. Marker locations between the identified marker locations are indexed by interpolating between the two closest identified marker locations, and not just by interpolating between the distal-most and proximal-most marker locations. Typically, such a technique reduces errors in estimating the intermediate marker locations due to a non-linear pullback rate of the endoluminal imaging probe, relative to a technique in which only the distal-most and proximal-most marker locations are identified.

For some applications, the additional marker locations are determined by acquiring additional angiograms in between the acquisition of the initial angiogram and the post-pullback angiogram. For each of these angiograms, the endoluminal imaging probe marker is identified, and the best frame is selected, typically in accordance with the techniques described herein. The marker location is typically co-registered with the combined best angiogram, in accordance with the techniques described herein. Based on the marker locations that are derived from the intermediate angiograms, a plurality of known marker locations are thereby determined with respect to the combined best angiogram. The system indexes IVUS slices at any section along the lumen (e.g., along the luminal center line) within the combined best angiogram by interpolating the marker locations corresponding to respective IVUS slices with reference to the two closest known IVUS marker locations to that section.

Alternatively, intermediate marker locations are determined by identifying a feature in an endoluminal image that is also identifiable in the combined best angiogram (or in an angiogram that is co-registered to the combined best angiogram). In response thereto, the location of the endoluminal probe marker at the acquisition of the endoluminal image may be determined with respect to the combined best angiogram. For some applications, the feature is a bifurcation, a curve or some other unique shape, a partial or total occlusion, a native valve, an aneurism, a septal defect, or a malformation. For some applications, the feature is a previously-deployed device visible in the extraluminal imaging. For some applications, the previously-deployed device is a stent, or a graft, or a replacement valve.

It is noted that in applying any of the techniques described hereinabove for associating endoluminal images with respective locations along the lumen, the system typically accounts for a known offset between the location of the moving, visible portion of the endoluminal imaging probe (e.g., a radiopaque marker), and the location of the image-acquiring portion of the probe (e.g., the ultrasound transducer, in the case of an IVUS probe).

It is noted that some of the techniques described hereinabove for associating endoluminal images with respective locations along the lumen are described with reference to an endoluminal imaging probe that acquires endoluminal images during pullback of the probe. The scope of the present invention includes applying any of the techniques described hereinabove for associating endoluminal images with respective locations along the lumen to an endoluminal imaging probe that acquires endoluminal images during insertion and advancement of the probe through the lumen (e.g., when images are acquired from an endobronchial airway), mutatis mutandis.

In general, when applying the techniques described herein, in indexing endoluminal image frames at any point along the lumen (e.g., along the luminal center line) with reference to the two closest identified marker locations to the point, it is typically assumed that pullback of the endoluminal probe and the acquisition of images by the endoluminal probe were performed at linear rates, and that there is therefore an equal distance between any pair of adjacent endoluminal images, and any other pair of adjacent endoluminal images that were acquired between the two closest identified locations of the endoluminal probe. For some applications, in indexing the endoluminal images at any point along the lumen (e.g., along the luminal center line) with reference to the two closest identified marker locations to the point, the system accounts for the probe acquiring endoluminal images at varying frame rates, and/or for pullback being performed at a non-linear rate (the rate of pullback in such cases, typically being estimated, based upon measurements of a sensor, as described with reference to FIG. 2).

For some applications, techniques described herein (e.g., techniques described with reference to FIGS. 1-11) are performed by a system that includes at least one processor. The processor is typically for use with an endoluminal data-acquisition device configured to acquire a plurality of endoluminal data points of a lumen of a body of a subject at respective locations inside the lumen, while the endoluminal data-acquisition device is moved through the lumen, the endoluminal data-acquisition device having a radiopaque marker coupled thereto. The processor is typically for use with an angiographic imaging device configured to acquire respective angiographic image of the lumen, at times associated with acquisitions of respective endoluminal data point by the endoluminal data-acquisition device. For some applications, the processor includes location-association functionality configured to determine first and second locations of the radiopaque marker respectively within first and second angiographic images of the lumen. For some applications, the processor includes image-co-registration functionality configured to generate a combined angiographic image of the lumen that includes representations of the first and second marker locations thereon, by co-registering the first and second angiographic images. For some applications, the processor includes location-association functionality configured to determine that at least one location on the combined angiographic image that is intermediate to the first and second locations of the radiopaque marker corresponds to an endoluminal data point acquired between the acquisitions of first and second data points corresponding to the first and second locations of the marker, by interpolating between the first and second locations of the radiopaque marker on the combined angiographic image. Typically, the processor includes display-driving functionality configured to drive the display to display an output, in response to determining that the intermediate location corresponds to the endoluminal data point acquired between the acquisitions of the first and second data points.

For some applications, the image-co-registration functionality is configured to generate the combined angiographic image of the lumen that includes representations of the first and second marker locations thereon, by co-registering the first and second angiographic images to one another, by designating one of the angiographic images as a baseline image, a shape of the lumen in the baseline image being designated as a baseline shape of the lumen. The image-co-registration functionality typically determines whether a shape of the lumen in the angiographic image that is not the baseline image is the same as the baseline shape of the lumen, and in response to determining that the shape of the lumen in the angiographic image that is not the baseline image is not the same as the baseline shape of the lumen designates the image that is not the baseline image as a non-baseline image. The image-co-registration functionality typically deforms the shape of the lumen in the non-baseline image, such that the shape of the lumen becomes more similar to the baseline shape of the portion than when the lumen in the non-baseline image is not deformed, and based upon the deformation of the non-baseline image, determines a location upon the baseline image at which the marker from within the non-baseline image should be located. The image-co-registration functionality typically generates an indication of the marker from within the non-baseline image at the determined location on the baseline image. For some applications, the image-co-registration functionality is configured to generate the combined angiographic image of the lumen using similar techniques to those described in US Patent Application 2010/0172556 to Cohen et al., which is incorporated herein by reference.

For some applications, techniques described herein (e.g., techniques described with reference to FIG. 3) are performed by a system that includes at least one processor. The processor is typically for use with (a) an endoluminal data-acquisition device configured to acquire a plurality of endoluminal data points of a lumen of a body of a subject at respective locations inside the lumen, while the endoluminal data-acquisition device is being moved through the lumen, the endoluminal data-acquisition device having a radiopaque marker coupled thereto, (b) contrast agent configured to be continuously injected into the lumen, during the movement of the endoluminal data-acquisition device, and (c) an angiographic imaging device configured to acquire a plurality of angiographic images of the endoluminal data-acquisition device inside the lumen, during the movement of the endoluminal data-acquisition device. The processor typically includes (a) location-association functionality configured to determine that endoluminal data points correspond to respective locations within the lumen, by determining locations of the radiopaque marker within the angiographic images of the lumen, by performing image processing on the angiographic images, the locations of the radiopaque marker within the angiographic images of the lumen corresponding to respective endoluminal data points, and (b) display-driving functionality configured to drive the display to display an output, in response to determining that the endoluminal data points correspond to respective locations within the lumen.

For some applications, phases 1 through 13 (or any applicable subset of those phases) of FIG. 3, are repeated subsequent to the deployment of the therapeutic device, such as in the course of performing a clinical evaluation of the outcome of the deployment of that device. For example, phases 1-13 may be repeated so as to facilitate the co-display of endoluminal images of the lumen, post-deployment of the device, with one or more extraluminal images of the lumen.

For some applications, pullback of the endoluminal data-acquisition device is performed in the course of a continuous injection of contrast agent performed under fluoroscopic imaging. For example, the endoluminal data-acquisition device may be an OCT probe, the image acquisition of which typically requires concurrent flushing of the lumen, in order to remove blood from the lumen, the blood interfering with the OCT imaging. Furthermore, contrast agent highlights the lumen and facilitates angiographic imaging of the lumen. Still furthermore, for some applications, the presence of contrast agent in the lumen facilitates acquisition of OCT data. Therefore, typically, during endoluminal imaging with an OCT probe, contrast agent is continuously injected into the lumen. In addition, the pullback of the OCT probe is typically performed rapidly relative to the pullback of an IVUS probe, and the frame acquisition rate of the OCT probe is typically greater than that of an IVUS probe.

For endoluminal imaging techniques such as OCT techniques, in which pullback of the imaging probe is performed under constant angiographic imaging, phases 4 to 10 of the technique described with reference to the flowchart shown in FIG. 3 may be substituted or combined with the phases described below. The steps described below are typically performed in conjunction with at least some of the other phases described with reference to the flowchart shown in FIG. 3, mutatis mutandis. Although the steps below are described with reference to endoluminal imaging with an OCT probe, the scope of the present invention includes performing these steps when using a different endoluminal imaging probe (such as an IVUS probe), the pullback of which is performed under constant angiographic imaging.

Pullback of the OCT probe commences (for example, by means of manual pullback, or at a known and steady rate of distance per second, such as by means of automated pullback), in conjunction with contrast agent injection performed under fluoroscopic imaging. The image slices generated by the OCT along the pullback are recorded and stored, synchronized (such as by time or by frame number) with the corresponding stored angiographic images. In addition, the locations of the OCT markers corresponding to respective, at least some OCT image slices are stored with reference to the corresponding stored angiographic image. For some applications, the marker locations are determined by identifying the markers in the angiographic images by (typically automatically) performing image processing on the angiographic images.

The total number of OCT images and fluoroscopic images acquired during the pullback may differ (due to different image acquisition frame rates). For example, the fluoroscopy frame rate may be 25 frames per second, whereas the OCT frame rate may be 100 frames per second, in which case OCT frames 1 through 4 are indexed to fluoroscopy frame 1, OCT frames 5 through 8 are indexed to fluoroscopy frame 2, etc.

From along the contrast injection in the course of the pullback, the system selects an angiogram frame, typically according to criteria described hereinabove, and depicts upon that frame the locations of the radiopaque marker(s) of the OCT probe, in whole or in part, by means of image processing, during pullback. The selected angiogram is denoted as the combined best angiogram. For some applications, and typically pursuant to the selection of the combined best angiogram, non-rigid transformation of one or more angiogram frames from the pullback sequence to the combined best angiogram is performed, typically automatically and typically on-line. The non-rigid transformation is typically followed by the depiction of the locations of the radiopaque marker(s) of the OCT probe on the resulting combined best angiogram, typically automatically and typically on-line. In depicting the marker locations on the resulting combined best angiogram, the non-rigid transformation of angiographic image frames associated with respective marker locations is accounted for. For some applications, such non-rigid transformation and marker depiction are performed according to techniques described in 2010/0222671 to Cohen, which is incorporated herein by reference.

Figure 8:
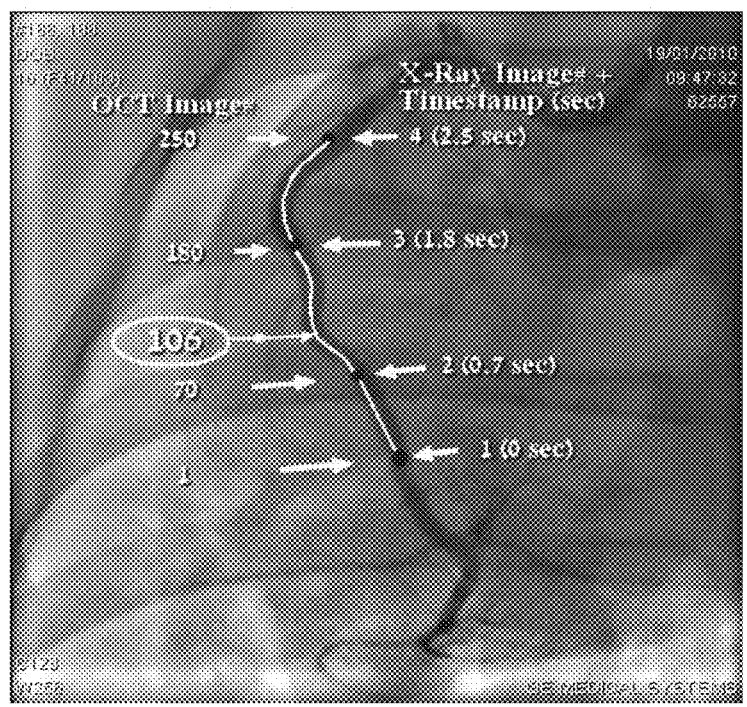
FIG. 8 shows a location on an extraluminal image of a lumen that has been selected, the index of the corresponding endoluminal image frame being derived in response thereto, in accordance with some applications of the present invention.

Reference is now made to FIG. 8 which shows a combined best angiogram, the combined best angiogram having been created in the course of a sequence for use in conjunction with an OCT endoluminal imaging probe, as described hereinabove, in accordance with some applications of the present invention. As shown, known OCT probe marker locations are shown on the combined best angiogram. Typically, even in cases in which pullback is performed under continuous angiographic imaging, not all of the marker locations are known, since the frame rate of the OCT probe is typically greater than the frame rate of the x-ray imager. The endoluminal probe marker locations corresponding to given endoluminal images that are not identifiable in the angiographic image are determined by indexing the marker locations with respect to the endoluminal images.

For example, in order to determine which is the endoluminal image corresponding to the point along the lumen in the combined best angiogram indicated by the double arrow in FIG. 8, it is determined that the OCT probe marker is a given distance between the marker locations that are identifiable in a given pair of angiograms. Based upon the times of the acquisitions of the given pair of angiograms, the rate at which the angiograms were acquired, and the rate at which the OCT frames were acquired, the OCT frame corresponding to that point may be determined.

For example, if the frame rate of the angiograms is 25 per second, the pair of angiograms were acquired, respectively at 0.7 seconds and 1.8 seconds from a given starting time, and the indicated location is one third of the distance between the marker locations known from the pair of angiograms, then it is determined that the corresponding OCT image was acquired at 1.06 seconds after the starting time, by performing the following calculation:

(0.33*(1.8−0.7)+0.7)=1.06

Thus, if the frame rate of the OCT probe is 100 frames per second, the corresponding OCT frame is frame 106.

Figure 9:
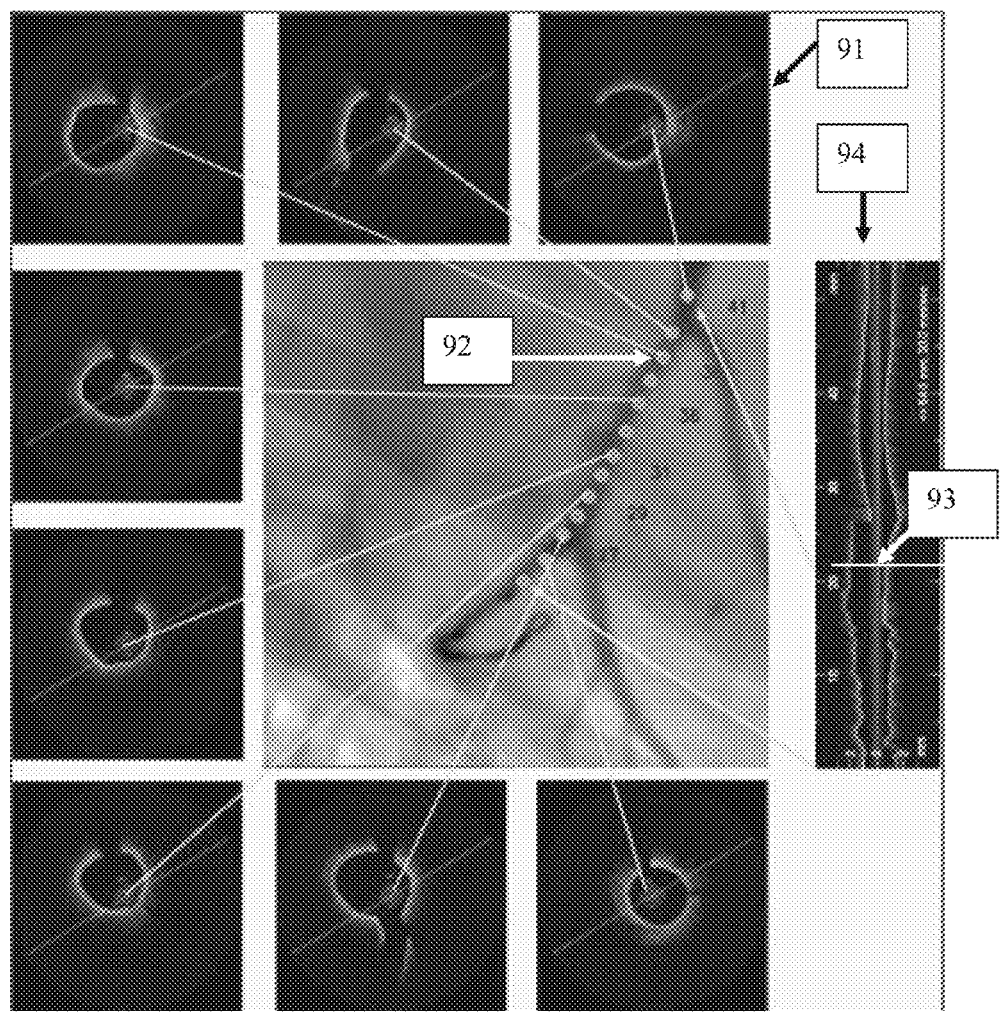
FIG. 9 shows co-display of previously-acquired endoluminal images and an extraluminal fluoroscopic image, in accordance with some applications of the present invention.

Reference is now made to FIG. 9, which shows the co-display of previously-acquired endoluminal image frames (e.g., frame 91), the endoluminal locations of the endoluminal imaging probe at the time of the acquisition of respective image frames being indicated on an extraluminal image of the lumen, the locations having been automatically indentified during pullback of the endoluminal imaging probe, in accordance with some applications of the present invention. For some applications, previously-acquired endoluminal OCT images frames (or other forms of endoluminal image frames) are connected by lines, to the corresponding endoluminal locations (such as location 92), of the OCT imaging probe at the times that the OCT image frames were acquired. For some applications, the range of the pullback is indicated with respect to an OCT image stack 94. For example, a line 93 is generated on the OCT image stack indicating where the pullback ended. For some applications, some endoluminal locations, such as location 92, are indicated as being associated with a corresponding location on the endoluminal image stack. For example, a line that is similar to line 93 may be generated on OCT image stack 94 to indicate the location on the image stack that corresponds to location 92.

For some applications, data acquired by a first endoluminal modality (e.g., IVUS) are co-registered with the fluoroscopic image stream, in accordance with the applications described hereinabove. Subsequently, data acquired by a second endoluminal modality (e.g., OCT) are co-registered with the fluoroscopic image stream, in accordance with the applications described hereinabove. Consequently, due to both data sets being co-registered with the fluoroscopic image stream, the two data sets are co-registered to one another. For some applications, the two endoluminal data sets are displayed as overlaid or otherwise merged with one another.

For some applications, generally similar steps to those described with reference to FIG. 3 are performed, except for the following differences. In phases 14, instead of a therapeutic endoluminal device (e.g., a treatment catheter) being inserted into the lumen, a second endoluminal data-acquisition device is inserted into the lumen. Typically, the first and second endoluminal data-acquisition devices acquire endoluminal images using respective imaging modalities. For example, in phase 1, an IVUS probe may be inserted into the lumen, and in phases 14 an OCT probe may be inserted into the lumen, or vice versa.

The current location of the second endoluminal data-acquisition device is determined, for example, using any of the techniques described herein (such as, by performing image processing on extraluminal images of the second endoluminal data-acquisition device inside the lumen). Endoluminal images which were previously acquired using the first data-acquisition device at the current location of the second endoluminal data-acquisition device are retrieved and displayed, typically on-line and typically automatically.

Typically, the endoluminal images which were acquired using the first data-acquisition device at the current location of the second endoluminal data-acquisition device are displayed together with endoluminal images that are being acquired in real time by the second endoluminal data-acquisition device, while the second endoluminal data-acquisition device is at the current location. For some applications, endoluminal images that are acquired in real time by the second endoluminal data-acquisition device, while the second endoluminal data-acquisition device is at the current location, are displayed together with an indication of the current location of the second endoluminal data-acquisition device with respect to an endoluminal image stack generated using endoluminal images that were previously acquired by the first endoluminal data-acquisition device. For some applications, using the above-described technique, data acquired by first and second endoluminal data acquisition devices are registered with respect to one another, and the co-registered data are displayed subsequent to termination of the acquisition of endoluminal images by both the first and the second endoluminal data-acquisition devices. For some applications, endoluminal images corresponding to the current location of the second endoluminal data-acquisition device that were acquired by the first endoluminal data acquisition device and/or by the second endoluminal data acquisition device are co-displayed with an indication of the current location of the second endoluminal data-acquisition device on an extraluminal image of the lumen, using the techniques described herein.

Figure 10:
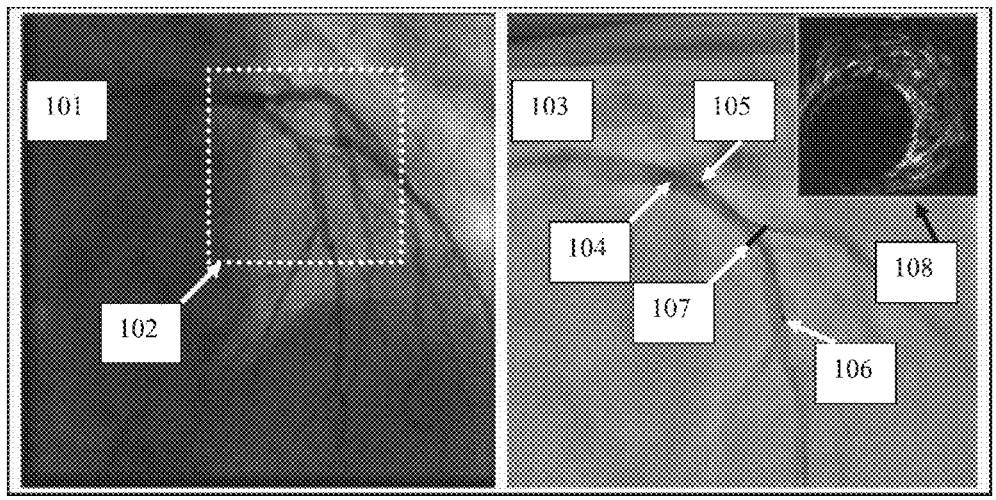
FIG. 10 shows the co-use of previously-acquired endoluminal images and a current extraluminal fluoroscopic image stream, in accordance with some applications of the present invention.

Reference is now made to FIG. 10, which shows the co-use of previously-acquired IVUS images and a current, stabilized, extraluminal fluoroscopic image stream, or with an angiogram image from the native fluoroscopic image stream, in accordance with some applications of the present invention. The native fluoroscopic image stream is displayed in left side window 101. A region of interest (ROI) 102 is marked, with a dotted white line, within left side window 101. A stabilized image stream, generally based upon ROI 102, is displayed in right side window 103. Vessel 104 is highlighted, by means of contrast agent. Radiopaque markers 105 and 106 are mounted respectively at the proximal and distal ends of a balloon carrying a stent. The balloon is being inserted through vessel 104. The balloon, as shown, is being positioned in preparation for the deployment of the stent at partial occlusion 107 which is at a narrower segment of vessel 104. An IVUS slice, acquired prior to placement of the balloon with markers 105 and 106 into vessel 104, corresponding to the current location of distal marker 106, is retrieved and displayed, typically in real time and typically automatically, at the upper right corner of right side window 103. FIG. 10 shows an illustrative IVUS slice 108 displayed in the upper right corner of right side window 103. In accordance with the applications described hereinabove, the IVUS slice that is displayed is a slice that was acquired by an IVUS probe previously, while the probe was inserted into the vessel under extraluminal fluoroscopy. IVUS slice 108 depicts a healthy vessel location. The display of slice 108 concurrently with positioning of the balloon, in preparation for stent deployment, assists in confirming that the distal end of the stent (corresponding to distal marker 106) is properly positioned at a "healthy shoulder" of occlusion 107 (i.e., the point along the arterial lumen at which the occlusion is no longer significant and/or the disease is no longer prevalent), as is typically desired. For some applications, the display of the corresponding IVUS slices is made relative to marker locations in a single angiogram frame. For some applications, the display of the corresponding IVUS slices is made relative to a three-dimensional model that was generated from two (or more) two-dimensional gated angiograms.

The cumulative effect of showing the extraluminal image stream and IVUS slice 108 is as if the stent is being positioned concurrently under both extraluminal fluoroscopic imaging and endoluminal IVUS imaging. In practice, such concurrent imaging is typically not possible because vessel 104 is too narrow to accommodate both the IVUS catheter and the stent catheter, and also because even if there were sufficient space, then the two catheters may interfere with one another.

Figure 11:
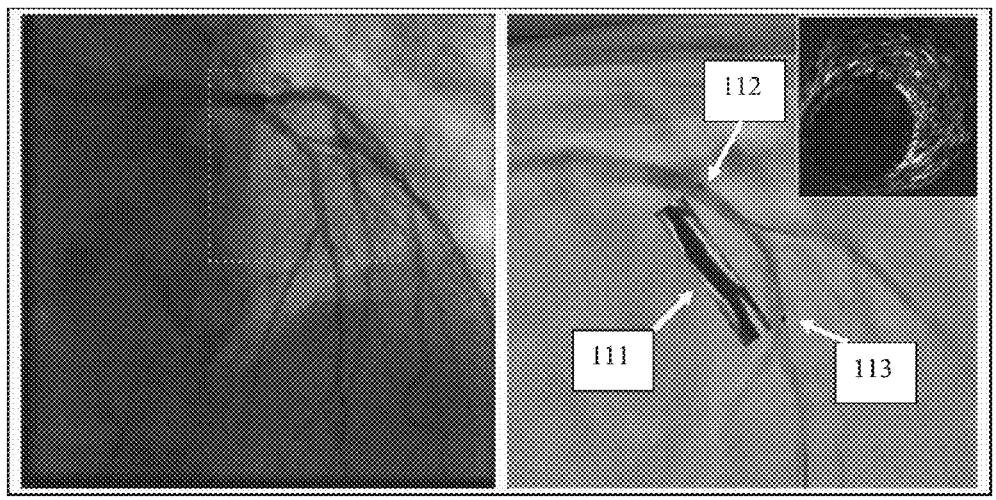
FIG. 11 shows the co-use of a stack of previously-acquired IVUS images and a current, extraluminal fluoroscopic image stream, in accordance with some applications of the present invention.

Reference is now made to FIG. 11, which shows the co-use of previously-acquired IVUS images and a current, stabilized, extraluminal fluoroscopic image stream, in accordance with some applications of the present invention. Stack 111 comprises previously-acquired IVUS slices previously acquired at locations corresponding to the current locations of balloon markers 112 and 113. For some applications, the display of the corresponding IVUS stack is made relative to marker locations in a static angiogram frame.

Figure 12:
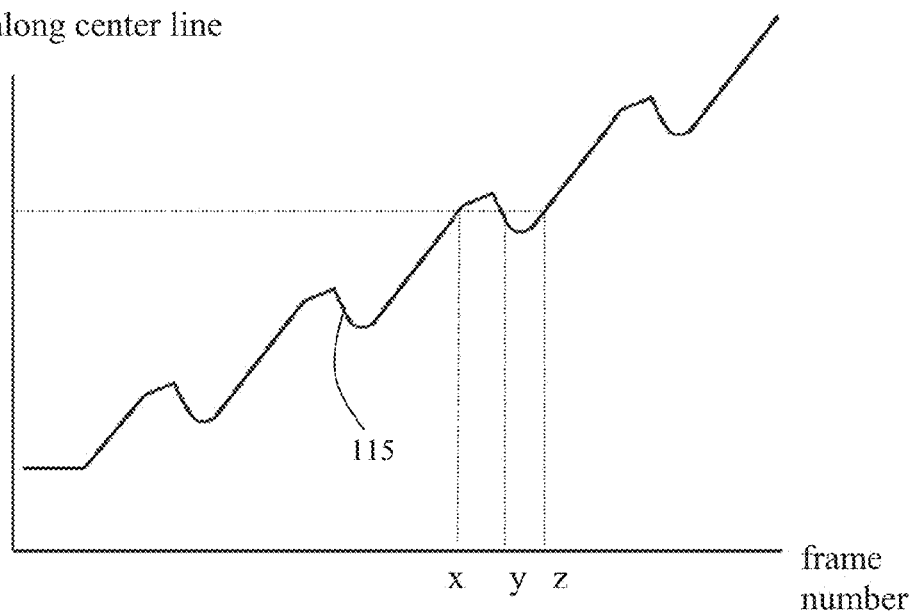
FIG. 12 is a graph indicating typical movement of an endoluminal imaging probe during pullback of the probe.

Reference is now made to FIG. 12, which is a graph showing the location along a lumen (e.g., along the center line of the lumen) of an imaging head of an endoluminal imaging probe, versus the frame numbers of the endoluminal image frames acquired by the probe, during pullback of the probe. Typically, even during automated pullback of the probe, the relative speed at which the imaging head of the probe moves with respect to the lumen, and, in some cases, the direction in which the imaging head moves with respect to the lumen, varies over the course of the cardiac cycle, due to pulsation of the lumen. As shown on portion 115 of the graph (which typically corresponds to a systolic phase of the cardiac cycle, or a portion thereof), in some cases, the imaging head of an endoluminal imaging probe moves forward (i.e., distally) with respect to the lumen during certain phases of the cardiac cycle, even during pullback (pullback generally being in a distal to proximal direction).

Still further typically, as a result of the imaging head moving forward with respect to the lumen, in some cases, two or more endoluminal image frames are acquired at a single location along the lumen. For example, as shown in FIG. 12, frames x, y, and z are acquired at a single location along the lumen. Frame x is acquired pre-systole, while the probe is moving in a distal to proximal direction with respect to the lumen, frame y is acquired during systole, while the probe is moving in a proximal to distal direction with respect to the lumen, and frame z is acquired post-systole, while the probe is moving back past the same location in a distal to proximal direction with respect to the lumen.

For some applications, manual pullback of the endoluminal imaging probe is performed by an operator. In some cases, during manual pullback, the operator pushes the probe forward at times in order to view a given region for a second time. As a result, the imaging probe typically acquires a plurality of endoluminal images of given locations within the region. For example, a first image may be acquired during the initial pullback past the location in the distal to proximal direction, a second image may be acquired when the probe is pushed forward by the operator in the proximal to distal direction, and a third image may be acquired when the probe is, subsequently, pulled back past the location in the distal to proximal direction for a second time.

For some applications, forward motion of the endoluminal imaging probe that is (a) due to pulsation of the lumen, and/or (b) due to an operator of the probe pushing the probe forward, is accounted for in order to facilitate co-registration of the endoluminal images to an extraluminal image. Typically, in order to facilitate co-registration, the system identifies redundant image frames (i.e., image frames that are not required because they are acquired at a location at which one or more additional image frames are acquired), and rejects at least some of the redundant image frames from being used for the co-registration, as described in further detail hereinbelow.

For some applications, forward motion of the imaging probe is detected by acquiring images of the imaging probe within the lumen, and performing image processing on the angiographic images in order to determine locations of the endoluminal image probe marker with respect to the lumen at the time of the acquisition of respective endoluminal image frames, e.g., in accordance with the techniques described hereinabove.

For some applications, angiographic images of the imaging probe within the lumen are acquired in the presence of contrast agent (which makes the lumen visible in the angiographic images), and the angiographic images are image processed in order to determine locations of the endoluminal image probe marker with respect to the lumen at the time of the acquisition of respective endoluminal image frames. Typically, using image processing of angiographic images of the probe within the lumen can be used to identify forward motion of the imaging probe that is (a) due to pulsation of the lumen, and (b) due to an operator of the probe pushing the probe forward. This is because, in the angiographic images, the system typically identifies a visible moving portion of the endoluminal imaging probe (e.g., a radiopaque marker on the imaging head). Using image processing, the system tracks the motion of the visible, moving portion of the endoluminal probe with respect to the lumen. Thus, motion of the visible, moving portion of the imaging probe with respect to the lumen is identifiable in the angiographic images, irrespective of the cause of the motion.

For some applications, fluoroscopic images of the imaging probe within the lumen are acquired in the absence of contrast agent, and the fluoroscopic images are image processed in order to determine locations of the endoluminal image probe marker with respect to the lumen at the time of the acquisition of respective endoluminal image frames. For some applications, as described hereinabove, the location of a moving, visible portion of the endoluminal imaging probe (e.g., a radiopaque marker on the imaging head of the endoluminal imaging probe) is determined according to its distance along a guide wire along which the imaging probe is inserted, the distance typically being measured relative to the distal tip of a guiding catheter through which the guidewire and the imaging probe were previously inserted. For some applications, the endoluminal imaging probe includes a portion that substantially does not move with respect to the lumen during pullback, such as an insertion sheath. The location of moving, visible portion of the imaging probe is determined, via image processing, with reference to the portion of the device that substantially does not move with respect to the lumen during pullback. Typically, using image processing of fluoroscopic images of the probe within the lumen can be used to identify forward motion of the imaging probe that is due to an operator of the probe pushing the probe forward. However, image processing of fluoroscopic images of the probe inside the lumen typically cannot be used to identify forward motion of the imaging probe that is due to pulsation of the artery, since all of the components of the probe (including the guidewire and the insertion sheath, for example) move with respect to the lumen due to pulsation of the lumen.

For some applications, forward motion of the endoluminal probe that is caused by an operator pushing the probe forward is determined using a longitudinal position/movement sensor coupled to apparatus through which the endoluminal probe is inserted, e.g., as described hereinabove with reference to FIG. 2.

In response to determining that two or more endoluminal image frames correspond to the same location along the lumen due to forward motion of the probe with respect to the lumen, at least one of the image frames is not used for the co-display of the endoluminal image frames with an extraluminal image of the lumen. Typically, only the first endoluminal image frame that was acquired at the location is used for the co-display of the endoluminal image frames with an extraluminal image of the lumen. For some applications, it is determined which at least one of the two or more endoluminal image frames that correspond to the same location along the lumen was acquired during forward motion of the probe, and this frame is rejected from being used in the co-display. Alternatively or additionally, another at least one of the two or more endoluminal image frames that correspond to the same location along the lumen is rejected from being used in the co-display.

For some applications, during pullback of the endoluminal imaging device, the subject's ECG signal is detected. Respective endoluminal images are identified as corresponding to the period in the subject's cardiac cycle at the time when the image was acquired, based upon the detected ECG signal (e.g., by indexing the image frames with respect to the subject's ECG signal). For some applications, based upon the identified correspondence, the system determines which of the endoluminal images were acquired in a given period of the subject's cardiac cycle, such as at least a portion of systole, and these image frames are not used for the co-display of the endoluminal image frames with an extraluminal image of the lumen. For example, frames corresponding to at least a portion of the subject's ECG signal between the S and T waves may be rejected from being used in the co-display. Typically, associating endoluminal image frames with phases of the subject's cardiac cycle (e.g., by indexing with respect to the subject's ECG signal) can be used to account for forward motion of the endoluminal imaging probe that is caused by motion of the probe with respect to the lumen due to pulsation of the lumen that is due to the subject's cardiac cycle.

For some applications, techniques described herein are used to account for the forward motion of the endoluminal imaging probe in order to facilitate the generation of an endoluminal image stack, the forward motion of the imaging probe typically being (a) due to pulsation of the lumen, and/or (b) due to an operator of the probe pushing the probe forward. Typically, in order to facilitate generation of an endoluminal image stack, the system identifies redundant image frames (i.e., image frames that are not required because they are acquired at a location at which one or more additional image frames are acquired), and rejects at least some of the redundant image frames from being used in the endoluminal image stack, as described in further detail hereinbelow. For some applications, in response to determining that some of the image frames were acquired during forward motion of the imaging probe, the system places the image frames in order within the image stack, and/or re-orders frames in an image stack that has already been generated, such that the frames within the stack are placed in the correct order. For some applications, the system indicates image frames within an image stack that were acquired during forward motion of the imaging probe, for example, by highlighting portions of the image stack that were acquired during the forward motion.

For some applications, forward motion of the imaging probe is detected by acquiring angiographic images or fluoroscopic images of the imaging probe within the lumen, and performing image processing on the angiographic images in order to determine locations of the endoluminal image probe marker with respect to the lumen at the time of the acquisition of respective endoluminal image frames, as described hereinabove. Typically, as described hereinabove, image processing of angiographic images can be used to identify forward motion of the imaging probe that is caused by (a) pulsation of the lumen, and (b) an operator of the probe pushing the probe forward. Further typically, image processing of fluoroscopic images can only be used to identify forward motion of the imaging probe that is caused by an operator of the probe pushing the probe forward. For some applications, forward motion of the endoluminal probe that is caused by an operator pushing the probe forward is determined using a longitudinal position/movement sensor coupled to apparatus through which the endoluminal probe is inserted, e.g., as described hereinabove with reference to FIG. 2.

For some applications, during pullback of the endoluminal imaging device, the subject's ECG signal is detected. Respective endoluminal images are identified as corresponding to the period in the subject's cardiac cycle at the time when the image was acquired, based upon the detected ECG signal (e.g., by indexing the image frames with respect to the subject's ECG signal). For some applications, based upon the identified correspondence, the system determines which of the endoluminal images were acquired in a given period of the subject's cardiac cycle, such as at least a portion of systole. Typically, associating endoluminal image frames with phases of the subject's cardiac cycle (e.g., by indexing with respect to the subject's ECG signal) can be used to account for forward motion of the endoluminal imaging probe that is caused by motion of the probe with respect to the lumen due to pulsation of the lumen that is due to the subject's cardiac cycle.

For some applications, in order to generate the image stack it is determined which image frames were acquired during forward motion of the endoluminal imaging probe (e.g., based upon image processing of angiographic or fluoroscopic images of the device inside the lumen, or based upon associating the frames with respective phases of the subject's cardiac cycle, such as, by indexing the frames with respect to the subject's ECG signal), and, in response thereto, those image frames are either rejected, or are appropriately placed within the stack. For some applications, in order to generate the image stack it is determined which locations along the lumen have two or more endoluminal images corresponding thereto, and, in response thereto, at least one of the image frames corresponding to the location is rejected from being used in the endoluminal image stack. Typically, only the first imaging frame to have been acquired at each location along the lumen is used in the image stack, and the other image frames acquired at the location are rejected from being used in the image stack. Further typically, it is determined which at least one of the two or more endoluminal image frames that correspond to the same location along the lumen were acquired during forward motion of the probe, and this frame is rejected from being used in the image stack. Alternatively or additionally, another at least one of the two or more endoluminal image frames that correspond to the same location along the lumen is rejected from being used in the image stack.

It is noted that some applications of the present invention have been described with respect to an endoluminal image probe that acquires image frames while moving generally in a distal to proximal direction (i.e., during pullback of the imaging probe), but that experiences some movement in a proximal to distal direction. The scope of the present invention includes applying the techniques described herein to an endoluminal image probe that acquires image frames while moving generally in a proximal to distal direction (i.e., while the probe is being pushed forward through the lumen), but that experiences some movement in a distal to proximal direction, mutatis mutandis.

For some applications, techniques described herein (e.g., techniques described with reference to FIG. 12) are performed by a system that includes at least one processor, for use with an endoluminal data-acquisition device that acquires a plurality of endoluminal data points of a lumen of a body of a subject while being moved through the lumen generally in a first direction with respect to the lumen. For some applications, the processor includes (a) duplicate-data-point-identification functionality configured to determine that, at at least one location, two or more endoluminal data points were acquired by the endoluminal data-acquisition device, (b) data-point-selection functionality configured to generate an output using a portion of the plurality of endoluminal data points of the lumen acquired using the endoluminal data-acquisition device, by using only a single data point corresponding to the location, and (c) display-driving functionality configured to drive a display to display the output.

For some applications, the processor includes (a) direction-determination functionality configured to determine that, while acquiring at least one of the endoluminal data points, the endoluminal data-acquisition device was moving in a second direction that is opposite to the first direction, (b) output-generation functionality configured, in response to the determining, to generate an output using at least some of the plurality of endoluminal data points of the lumen acquired using the endoluminal data-acquisition device, and (c) display-driving functionality configured to drive a display to display the output.

For some applications, locations of an endoluminal imaging probe associated with a first endoluminal modality (e.g., IVUS) are identified as corresponding to respective endoluminal image frames of the first imaging modality, in accordance with the techniques described hereinabove. Subsequently, locations of an endoluminal imaging probe associated with a second endoluminal modality (e.g., OCT) are identified as corresponding to respective endoluminal image frames of the second imaging modality, in accordance with the techniques described hereinabove. For example, forward motion of one or both of the endoluminal imaging probes may be accounted for in associating the locations of the endoluminal image probes with the image frames, in accordance with techniques described hereinabove. Consequently, the two data sets are co-registered to one another. For some applications, the two endoluminal data sets are displayed as overlaid or otherwise merged with one another.

For some applications, in order to determine the angular orientation of the probe with respect to the lumen at the time of the acquisition of respective endoluminal image frames, an asymmetrically shaped radiopaque marker that is visible in extraluminal images (e.g., angiographic or fluoroscopic images) of the lumen is disposed on the imaging head of the endoluminal probe. Alternatively or additionally, the marker may be disposed asymmetrically with respect to the longitudinal axis of the imaging head of the endoluminal probe. During the acquisition of endoluminal image frames by the endoluminal imaging probe, extraluminal images are acquired of the endoluminal image probe within the lumen. Image processing is applied to the fluoroscopic images in order to determine the angular orientation of the probe with respect to the lumen at the time of the acquisition of respective endoluminal image frames, typically automatically and typically on-line, in accordance with techniques described herein.

For some applications, the aforementioned techniques are applied in order to account for unintentional rotation (typically, roll) of the endoluminal imaging probe with respect to the lumen, due to pulsation of the lumen, for example. For some applications, the aforementioned techniques are applied in order to facilitate the generation of an endoluminal image stack, in which the images that comprise the stack are correctly rotationally aligned. Alternatively or additionally, the aforementioned techniques are applied to determine the orientation with respect to each other of vessels that appear in the endoluminal images.

Figure 13:
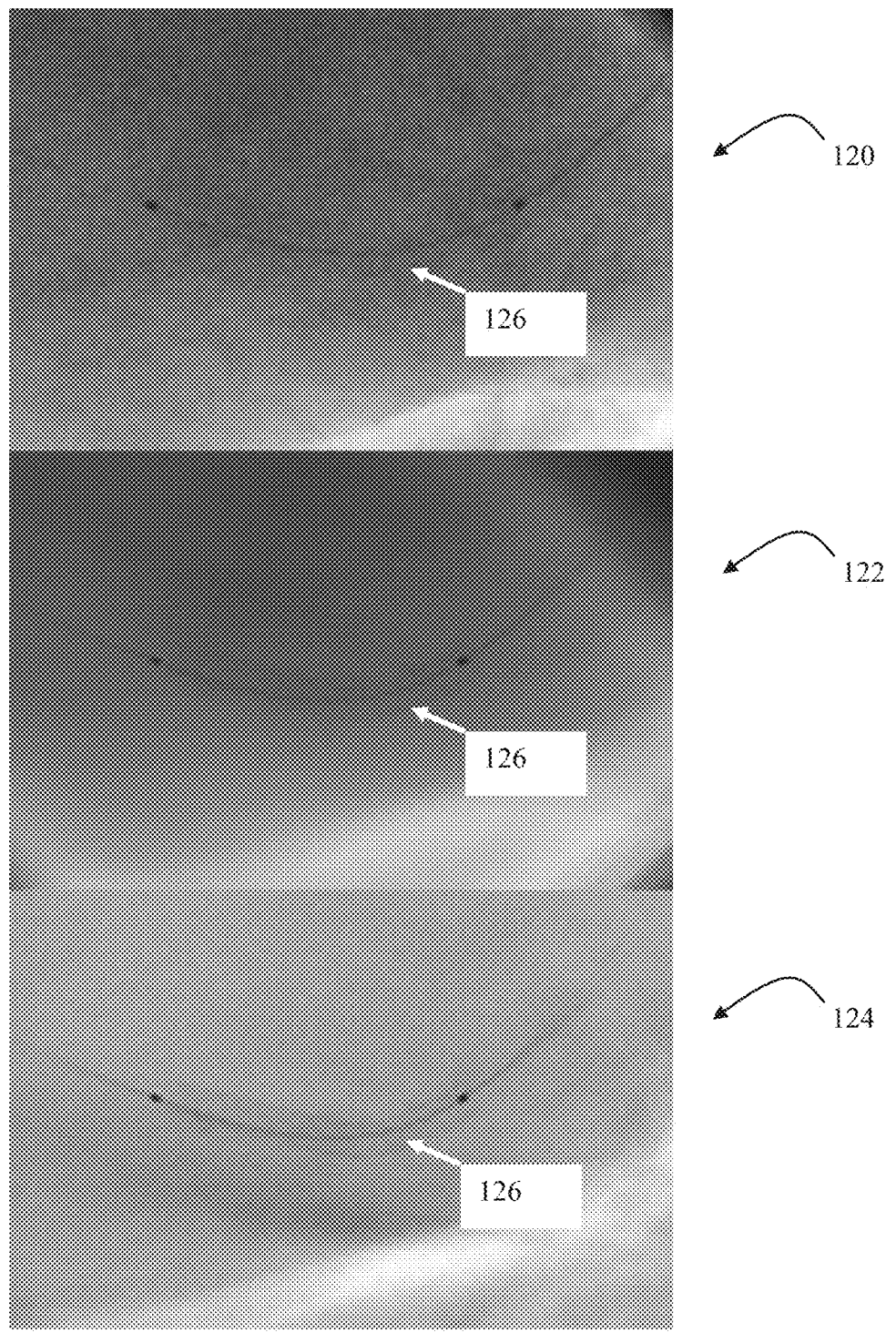
FIG. 13 shows an extraluminal image of a stent inside a blood vessel that has been enhanced, in accordance with some applications of the present invention.

Reference is now made to FIG. 13 which shows image frames 120, 122, and 124 of a stent inside a blood vessel. Frame 120 is a raw image frame of the stent inside the blood vessel.

For some applications, an enhanced extraluminal image, or image sequence, of a deployed device and/or tool (for example, a stent) is displayed. In accordance with respective applications, the enhanced image of the deployed device is co-registered to an endoluminal image (e.g., in accordance with the techniques described herein), or is displayed independently of any endoluminal images. For some applications, the enhancement is performed in accordance with techniques described in US Patent Application 2010/0172556 to Cohen et al., which is incorporated herein by reference.

For some applications, the image of the tool within the stabilized image stream is enhanced in real time or near real time. For some applications, enhancement of the image of the tool is performed in combination with the techniques described in WO 08/107905 to Iddan, which is incorporated herein by reference.

For some applications, enhancement is performed automatically upon frames that have been image-tracked such that the tool is displayed in a same or similar relative location throughout most or all frames, as described in US Patent Application 2010/0172556 to Cohen, which is incorporated herein by reference. For some applications, enhancement is performed by means of temporal filtering of the image-tracked frames. Typically, enhancement is performed in real time, or in near real time. Frame 122 of FIG. 13 is an enhanced image frame, generated in accordance with techniques described in US Patent Application 2010/0172556 to Cohen. It may be observed that stent 126 is more visible in frame 122 than in raw image frame 120.

For some applications, the temporal filtering applies a weighted averaging function to the value of each pixel, as defined by its relative locations in a series of consecutive frames, and displays the resulting image. Alternatively or additionally, the temporal filtering applies a median function to the value of each pixel, as defined by its relative locations in a series of consecutive frames, and displays the resulting image. Further alternatively or additionally, the temporal filtering applies a mode function to the value of each pixel, as defined by its relative locations in a series of consecutive frames, and displays the resulting image.

For some applications, in addition to the application of a temporal filter, a spatial filter is applied to increase the contrast in the enhanced image. For example, the spatial filter may be a leveling filter. For some applications, contrast is increased by histogram stretching, and/or by gamma correction.

In accordance with respective applications, contrast enhancement is specifically applied to the edges of a tool, such as a balloon, or to the struts of a tool, such as a stent.

For some applications, only the final image, representing the outcome of the enhancement process, is displayed. Alternatively, intermediate frames, reflecting gradual enhancement, are also displayed on-line.

For some applications, enhancement is performed upon a number of typically-consecutive gated image frames. When using gated images, the enhancement is typically applied to fewer image frames than when the enhancement is applied to non-gated image frames, which may degrade the outcome of the enhancement process. However, such gated frames are often already aligned to a substantial extent, which may improve the outcome of the enhancement process.

For some applications, alternative or additional techniques are applied to enhance the visibility of the tool in an extraluminal image or image stream, the techniques being performed typically on-line, and typically automatically. For some applications, the enhancement is performed by applying an iterative algorithm on a set of images, the algorithm operating as follows. An initial enhanced image is calculated from registered images, typically by means of techniques disclosed hereinabove, such as temporal filtering. In each iteration, the algorithm attempts to improve the already-created enhanced image, by selecting only some of the image frames to be used for creating a new enhanced image frame, and not using the remaining image frames.

Typically, device contours are identified in at least some of the image frames from which a recent enhanced image, or image stream, was generated by the system (typically automatically, and typically on-line) (a) identifying marker locations within the image frame, (b) identifying curved edge lines in the vicinity of markers, and (c) interpreting the edge lines as the device contours. From among those image frames, a subset of the image frames in which the device contours are most similar to each other is selected, and other image frames are rejected. It is noted that in accordance with this technique, some image frames are rejected from the subset of image frames, even though edge lines corresponding to the device contours appear in the rejected image frames.

For some applications, the similarity of the device contours in a set of image frames is determined based upon the similarity of the shapes of the edge lines in the image frames. Alternatively or additionally, the similarity of the device contours in a set of image frames is determined by determining an extent to which the edge lines are parallel to an imaginary line running from a first (e.g., distal) marker to a second (e.g., proximal) marker in the image frames.

Subsequent to the subset of image frames having been selected, that subset is used for creating a new enhanced image, again with the enhancement performed according to techniques disclosed hereinabove. Typically, before averaging the subset of image frames in order to create the new enhanced image frame, at least some of the image frames in the subset are translated, such that the edge lines in all of the image frames in the subset are aligned with each other.

As described hereinabove, typically, in each step of the iterative algorithm, the image frames in which the device contours are the most similar to each other are selected. Alternatively, a single image frame is selected as a baseline image frame, and image frames are selected based upon a level of similarity of device contours in the image frames to those of the baseline image frame.

Typically, the above-described algorithm is applied iteratively until no more image frames are excluded from the most recent subset. Typically, the final outcome of applying the iterative algorithm is an enhanced image frame in which at least one of the device contour, or edges, or struts, or other device elements, are more visible than they are in non-enhanced images frames, or in enhanced image frames that have not had the above iterative algorithm applied to them, ceteris paribus. Typically, applying the iterative algorithm to image frames that have been enhanced in accordance with techniques described in US 2010/0172556 to Cohen, which is incorporated herein by reference, further enhances the image frames.

For example, the iterative enhancement may be used when enhancing a stent previously deployed by a balloon carrying radiopaque markers. The deflated balloon still resides, intraluminally, within the deployed stent. Typically at this stage, due to pulsation of the lumen, the balloon and the radiopaque markers thereof shift (e.g., axially shift, and/or radially shift) with respect to the endoluminal walls. The stent is fixated to the endoluminal walls, and does not therefore shift with respect to the endoluminal walls. Consequently, generating an enhanced image of the stent from all image frames acquired along the cardiac cycle, using a technique that relies upon using the locations of the radiopaque markers (e.g., as described in US Patent Application 2010/0172556 to Cohen, which is incorporated herein by reference) might suffer from a blurring effect resulting from the different locations of the balloon markers, relative to the stent struts, in some of those frames.

The application of the iterative enhancement algorithm disclosed hereinabove, in which image frames are selected based upon the similarity of contours in the image frames to the device contours, typically reduces such a blurring effect. Thus, using the above-described iterative enhancement algorithm for generating an enhanced image frame (according to which, some image frames are rejected from being used to generate the enhanced image frame) may produce a better-enhanced image of the deployed stent than an enhanced image frame that is generated using all the image frames (or all of the gated image frames) irrespective of the similarity of contours in the image frames to the device contours.

Frame 124 of FIG. 13 is an enhanced image frame, generated in accordance with techniques described in US Patent Application 2010/0172556 to Cohen, and using the iterative algorithm, in accordance with some applications of the present invention. It may be observed that stent 126 is more visible in frame 124 than in raw image frame 120, and in image frame 122, which was generated using only techniques described in US Patent Application 2010/0172556 to Cohen.

For some applications, an enhanced image stream is displayed, by enhancing a plurality of image frames using techniques described herein (e.g., using the above-described iterative algorithm), and displaying the enhanced image frames as an image stream.

For some applications, techniques described herein (e.g., techniques described with reference to FIG. 13) are performed by a system that includes at least one processor. For some applications, the processor includes image-receiving functionality configured to receive the plurality of image frames into the processor, and marker-identifying functionality configured to automatically identify radiopaque markers in the image frames. Typically, the processor further includes edge-line-identifying functionality configured to automatically identify edge lines in a vicinity of the radiopaque markers in the image frames, and image-selection functionality configured, in response to the identifying of the edge lines, to select a subset of the image frames that are based upon the acquired image frames, based upon a level of similarity between the edge lines in the selected image frames to one another. For some applications, the processor includes image-alignment functionality configured to align the edge lines in a plurality of the selected image frames. Typically, the processor includes image-averaging functionality configured to generate an averaged image frame by averaging the plurality of aligned image frames, and display-driving functionality configured to drive a display to display the averaged image frame.

It is noted that although some techniques for co-using extraluminal images and endoluminal data are described hereinabove primarily with respect to extraluminal fluoroscopic/angiographic images and endoluminal IVUS images, the scope of the present invention includes applying the techniques described herein to other forms of extraluminal and endoluminal images and/or data, mutatis mutandis. For example, the extraluminal images may include images generated by fluoroscopy, CT, MRI, ultrasound, PET, SPECT, other extraluminal imaging techniques, or any combination thereof. Endoluminal images may include images generated by optical coherence tomography (OCT), near-infrared spectroscopy (NIRS), intravascular ultrasound (IVUS), endobronchial ultrasound (EBUS), magnetic resonance (MR), other endoluminal imaging techniques, or any combination thereof. Endoluminal data may include data related to pressure (e.g., fractional flow reserve), flow, temperature, electrical activity, or any combination thereof. Examples of the anatomical structure to which the aforementioned co-registration of extraluminal and endoluminal images may be applied include a coronary vessel, a coronary lesion, a vessel, a vascular lesion, a lumen, a luminal lesion, and/or a valve. It is noted that the scope of the present invention includes applying the techniques described herein to lumens of a subject's body other than blood vessels (for example, a lumen of the gastrointestinal or respiratory tract).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with an endoluminal data-acquisition device having a radiopaque portion coupled thereto, the method comprising:
while the endoluminal data-acquisition device is being moved through the lumen, acquiring a plurality of endoluminal data points of the lumen using the endoluminal data-acquisition device;
using an extraluminal imaging device, acquiring a first extraluminal image of the lumen, at a time associated with an acquisition of the first endoluminal data point by the endoluminal data-acquisition device, the first extraluminal image including an image of the radiopaque portion at a first location within the lumen;
using the extraluminal imaging device, acquiring a second extraluminal image of the lumen, at a time associated with an acquisition of the second endoluminal data point by the endoluminal data-acquisition device, the second extraluminal image including an image of the radiopaque portion at a second location within the lumen; and
using at least one processor:
generating a combined extraluminal image of the lumen that contains images of the radiopaque portion at the first and second locations within the lumen, by co-registering the first and second extraluminal images with each other;
identifying at least one location on the combined extraluminal image as corresponding to a location within the lumen at which a given one of the endoluminal data points was acquired, by identifying the first and second locations of the radiopaque portion within the combined extraluminal image; and
generating an output on an output device, in response thereto.

2. The method according to claim 1, wherein the endoluminal data-acquisition device includes an endoluminal imaging device, and wherein acquiring the plurality of endoluminal data points of the lumen using the endoluminal data-acquisition device comprises acquiring a plurality of endoluminal images using the endoluminal imaging device.

3. The method according to claim 1, wherein the endoluminal data-acquisition device includes an endoluminal data-acquisition device configured to acquire non-image data points, and wherein acquiring the plurality of endoluminal data points of the lumen using the endoluminal data-acquisition device comprises acquiring a plurality of non-image endoluminal data points using the endoluminal data-acquisition device.

4. The method according to claim 1, wherein identifying the at least one location on the combined extraluminal image as corresponding to the location within the lumen at which the given one of the endoluminal data points was acquired comprises identifying at least one location on the combined extraluminal image as corresponding to a location within the lumen at which a given one of the endoluminal data points was acquired between acquisitions of the first and second endoluminal data points, by interpolating between the first and second locations of the radiopaque portion on the combined extraluminal image.

5. The method according to claim 4, wherein interpolating between the first and second locations of the radiopaque portion on the combined extraluminal image comprises assuming that, between acquiring respective successive pairs of endoluminal data points between the acquisitions of the first and second endoluminal data points, the endoluminal data-acquisition device travelled equal distances.

6. The method according to claim 4, wherein interpolating between the first and second locations of the radiopaque portion on the combined extraluminal image comprises assuming that a rate of the movement of the endoluminal data-acquisition device was linear between the acquisitions of the first and second endoluminal data points.

7. The method according to claim 4, wherein interpolating between the first and second locations of the radiopaque portion on the combined extraluminal image comprises performing linear interpolation between the first and second locations of the radiopaque portion on the combined extraluminal image.

8. Apparatus comprising:
an endoluminal data-acquisition device configured to acquire a plurality of endoluminal data points of a lumen of a body of a subject at respective locations inside the lumen, while the endoluminal data-acquisition device is moved through the lumen, the endoluminal data-acquisition device having a radiopaque portion coupled thereto;
an extraluminal imaging device configured to (a) acquire a first extraluminal image of the lumen, at a time associated with an acquisition of a first endoluminal data point by the endoluminal data-acquisition device, and (b) acquire a second extraluminal image of the lumen, at a time associated with an acquisition of a second endoluminal data point by the endoluminal data-acquisition device;
a display; and
at least one processor, configured to:
generate a combined extraluminal image of the lumen that contains images of the radiopaque portion at the first and second locations within the lumen, by co-registering the first and second extraluminal images with each other;
identify at least one location on the combined extraluminal image as corresponding to a location within the lumen at which a given endoluminal data point was acquired, by identifying the first and second locations of the radiopaque portion within the combined extraluminal image;
drive the display to display an output, in response thereto.

9. The apparatus according to claim 8, wherein the endoluminal data-acquisition device comprises an endoluminal imaging device configured to acquire the plurality of endoluminal data points by acquiring a plurality of endoluminal images.

10. The apparatus according to claim 8, wherein the endoluminal data-acquisition device comprises an endoluminal data-acquisition device acquire configured to acquire the plurality of endoluminal data points by acquiring a plurality of non-image endoluminal data points.

11. The apparatus according to claim 8, wherein the processor is configured to identify at least one location on the combined extraluminal image as corresponding to a location within the lumen at which a given one of the endoluminal data points was acquired between acquisitions of the first and second endoluminal data points, by interpolating between the first and second locations of the radiopaque portion on the combined extraluminal image.

12. The apparatus according to claim 11, wherein the processor is configured to interpolate between the first and second locations of the radiopaque portion on the combined extraluminal image by assuming that, between acquiring respective successive pairs of endoluminal data points between the acquisitions of the first and second endoluminal data points, the endoluminal data-acquisition device travelled equal distances.

13. The apparatus according to claim 11, wherein the processor is configured to interpolate between the first and second locations of the radiopaque portion on the combined extraluminal image by assuming that a rate of the movement of the endoluminal data-acquisition device was linear between the acquisitions of the first and second endoluminal data points.

14. The apparatus according to claim 11, wherein the processor is configured to interpolate between the first and second locations of the radiopaque portion on the combined extraluminal image by performing linear interpolation between the first and second locations of the radiopaque portion on the combined extraluminal image.

15. A method for use with an endoluminal data-acquisition device having a radiopaque portion coupled thereto, the method comprising:
while the endoluminal data-acquisition device is being moved through the lumen, acquiring at least a first endoluminal data point of the lumen using the endoluminal data-acquisition device;
acquiring a plurality of extraluminal images of the lumen, using an extraluminal imaging device;
designating a first one of the extraluminal images of the lumen as a baseline image, the lumen having a given shape in the baseline image;
determining that a second one of the extraluminal images of the lumen was acquired at a time associated with the acquiring of the first endoluminal data point by the endoluminal data-acquisition device, the second extraluminal image including an image of the radiopaque portion at a given location within the lumen;
deforming the shape of the lumen in the second extraluminal image, such that the shape of the lumen in the second extraluminal image becomes more similar to the given shape of the lumen than when the lumen in the second extraluminal image is not deformed;
based upon the deforming of the second extraluminal image, determining a location upon the baseline image that corresponds to the location of the radiopaque portion within the second extraluminal image;
co-registering the first endoluminal data point to the baseline image, in response thereto; and
generating an output, in response to the co-registering.

16. The method according to claim 15, wherein the endoluminal data-acquisition device includes an endoluminal imaging device, and wherein acquiring the endoluminal data point of the lumen using the endoluminal data-acquisition device comprises acquiring one or more endoluminal images using the endoluminal imaging device.

17. The method according to claim 15, wherein the endoluminal data-acquisition device includes an endoluminal data-acquisition device configured to acquire non-image data points, and wherein acquiring the endoluminal data point of the lumen using the endoluminal data-acquisition device comprises acquiring one or more non-image endoluminal data points using the endoluminal data-acquisition device.

18. The method according to claim 15,
wherein acquiring at least the first endoluminal data point of the lumen using the endoluminal data-acquisition device comprises acquiring a plurality of endoluminal data points, using the endoluminal data-acquisition device, while the endoluminal data-acquisition device is moving through the lumen,
the method further comprising:
determining, with respect to the baseline image, a location of the radiopaque portion at a time at which a second endoluminal data point was acquired; and
co-registering the second endoluminal data point to the baseline image, in response thereto.

19. The method according to claim 18, further comprising determining that at least one location on the baseline image corresponds to an endoluminal data point acquired between the acquisitions of the first and second endoluminal data points, by interpolating between (a) the location of the radiopaque portion with respect to the baseline image at the time at which the first endoluminal data point was acquired, and (b)

the location of the radiopaque portion with respect to the baseline image at the time at which the second endoluminal data point was acquired.

20. The method according to claim 19, wherein the interpolating comprises assuming that, between acquiring respective successive pairs of endoluminal data points between the acquisitions of the first and second data points, the endoluminal data-acquisition device travelled equal distances.

21. The method according to claim 19, wherein the interpolating comprises assuming that a rate of the movement of the endoluminal data-acquisition device was linear between the acquisitions of the first and second data points.

22. The method according to claim 19, wherein the interpolating comprises performing linear interpolation between (a) the location of the radiopaque portion with respect to the baseline image at the time at which the first endoluminal data point was acquired, and (b) the location of the radiopaque portion with respect to the baseline image at the time at which the second endoluminal data point was acquired.

\* \* \* \* \*